US010330690B2

(12) United States Patent
Guadagno et al.

(10) Patent No.: US 10,330,690 B2
(45) Date of Patent: Jun. 25, 2019

(54) LP(A) SUBFORM SIZE IDENTIFICATION BY CAPILLARY ISOTACHOPHORESIS ELECTROPHORESIS WITH LASER-INDUCED-FLUORESCENCE

(71) Applicant: Helena Laboratories Corporation, Beaumont, TX (US)

(72) Inventors: Philip Guadagno, Vashon Island, WA (US); Erin Grace (Summers) Bellin, Sandston, VA (US)

(73) Assignee: HELENA LABORATORIES CORPORATION, Beaumont, TX (US)

( * ) Notice: Subject to any disclaimer, the term of this patent is extended or adjusted under 35 U.S.C. 154(b) by 413 days.

(21) Appl. No.: 14/924,540

(22) Filed: Oct. 27, 2015

(65) Prior Publication Data
US 2016/0116494 A1 Apr. 28, 2016

Related U.S. Application Data

(60) Provisional application No. 62/068,927, filed on Oct. 27, 2014, provisional application No. 62/147,668, filed on Apr. 15, 2015.

(51) Int. Cl.
*G01N 33/92* (2006.01)
*G01N 27/447* (2006.01)
(52) U.S. Cl.
CPC ........... *G01N 33/92* (2013.01); *G01N 27/447* (2013.01)
(58) Field of Classification Search
None
See application file for complete search history.

(56) References Cited

U.S. PATENT DOCUMENTS

| 2003/0054569 A1* | 3/2003 | Cheng ................. C12Q 1/6818 436/516 |
| 2008/0227209 A1 | 9/2008 | Deng |
| 2012/0052594 A1 | 3/2012 | Guadagno |
| 2013/0319864 A1 | 12/2013 | Guadagno |

FOREIGN PATENT DOCUMENTS

| JP | 2009 031092 | 2/2009 | |
| WO | WO 96/19500 | 6/1996 | |
| WO | WO-2005066373 A1 * | 7/2005 | ........... C12Q 1/6816 |
| WO | WO 2007/045865 | 4/2007 | |
| WO | WO 2014/137828 | 9/2014 | |
| WO | WO 2014/145678 | 9/2014 | |

OTHER PUBLICATIONS

Lamon-Fava et al., Lipoprotein(a) levels, apo(a) isoform size, and coronary heart disease risk in the Framingham Offspring Study, 52,(6), (2011), p. 1181-1187 (Year: 2011).*
Marcovina et al., Effect of the Number of Apolipoprotein(a) Kringle 4 Domains on Immunochemical Measurements of Lipoprotein(a), Clin. Chem. 41(2), (1995), p. 246-255 (Year: 1995).*
Alexandra Schlenck et al. "Characterization and quatification of serum lipoprotein subfractions by capillary isotachophoresis: relationships with lipid, apolipoprotein, and lipoprotein levels," Journal of Lipid Research. vol. 40, No. 11 (1999) pp. 2125-2133.
Alfred Bottcher et al., "Preparative free-solution isotachophoresis for separation of human plasma lipoproteins: apolipoprotein and lipid composition of HDL subfractions," Journal of Lipid Research. (2000) vol. 41, No. 6 pp. 905-915.
C Lackner et al. "Molecular basis of apolipoprotein (a) isoform size heterogeneity as revealed by pulsed-field gel electrophoresis," Journal of Clinical Investigation (1991) vol. 87, No. 6 pp. 2153-2161.

* cited by examiner

*Primary Examiner* — Ram R Shukla
*Assistant Examiner* — Ellen J Marcsisin
(74) *Attorney, Agent, or Firm* — Jerold I. Schneider

(57) ABSTRACT

The application describes methods for determining the concentration and/or particle number of a lipoprotein(a) subform in a biological sample using capillary isotachophoresis laser induced fluorescence (CE-ITP-LIF) and compositional analysis of lipoprotein(a) particles. The ability to measure the concentration and/or particle number of a lipoprotein(a) subform in a biological sample provides a useful diagnostic tool for assessing cardiovascular risk in a subject.

17 Claims, 42 Drawing Sheets

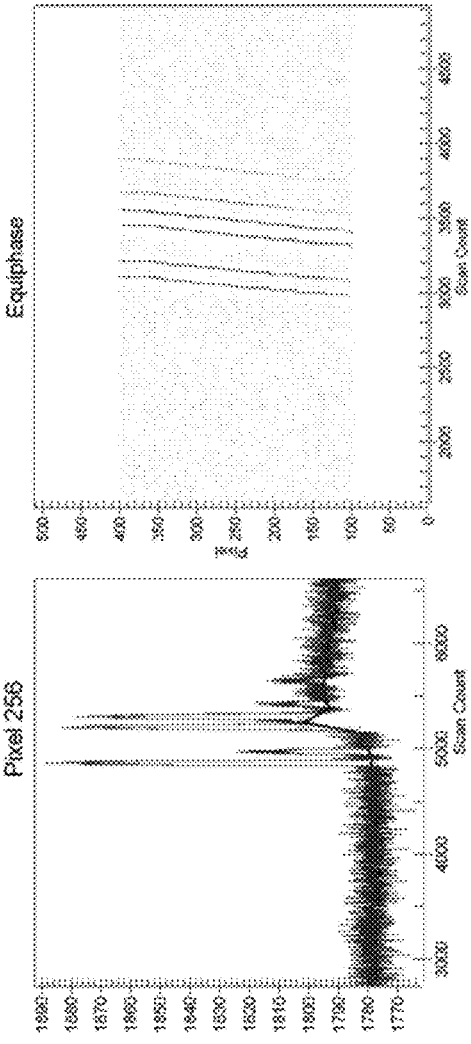
FIG. 5A
FIG. 5B
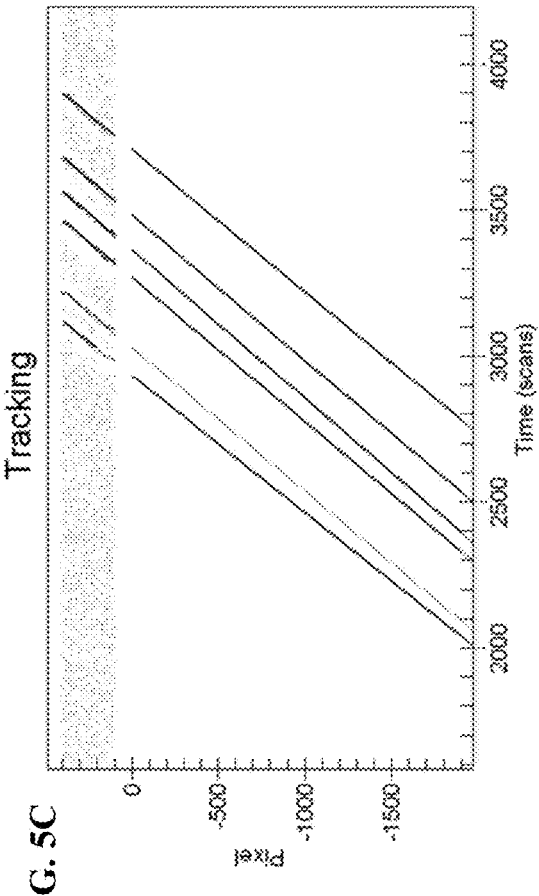
FIG. 5C
FIGS. 5A-5C

LP(A) SUBFORM SIZE IDENTIFICATION BY CAPILLARY ISOTACHOPHORESIS ELECTROPHORESIS WITH LASER-INDUCED-FLUORESCENCE

This application claims the benefit of U.S. Provisional Patent Application Ser. No. 62/068,927, filed Oct. 27, 2014 and U.S. Provisional Patent Application Ser. No. 62/147,668 filed Apr. 15, 2015, which are hereby incorporated by reference in their entirety.

FIELD OF THE INVENTION

The present invention relates to methods for determining the concentration and/or particle number of a lipoprotein(a) subform in a biological sample. The invention also teaches a method of assessing cardiovascular risk in a subject.

BACKGROUND

Advances in the understanding of the physiological nature of individual lipoprotein types and their effects on human health make it imperative to understand populations of lipoprotein particles and subforms, each of which is the result of, and participates in, specific metabolic processes. Such processes may be good or bad for a particular patient's health, having consequences for therapeutic efforts, including pharmacological therapy, lifestyle changes, diet changes, or other medical intervention.

Lipoproteins are particles in the blood comprising a lipid particle and a variety of apolipoprotein moieties. Lipoproteins span a wide variety of sizes and apolipoprotein content, each species having a unique metabolic pathway and unique relevance to patient health.

There are several methods for measuring levels of lipoproteins including lipoprotein(a) (Lp(a)) from bodily fluids. Lipoprotein particle levels can be measured by nuclear magnetic resonance (NMR) spectroscopy. This involves acquiring NMR data from the sample, processing the data to generate a chemical shift spectrum, and analyzing the spectra for subclasses of the major classes of lipoprotein to determine the concentration of each of the lipoprotein constituents and the distribution of subclasses of the constituents. Use of NMR can generate size and particle count values for HDL, VLDL, IDL and LDL particles, but not Lp(a) particles. Lp(a) particles must be measured by specialized techniques like immunofixation and acid violet staining, but this is labor intensive and not automatable. Additionally, direct quantification of lipoprotein cholesterol can be achieved by enzymatic assay of the individual lipoproteins, which can be separated by ultracentrifugation, electrophoresis, or selective precipitation. The most accurate method for isolating lipoprotein is ultracentrifugation; but, this method is very time consuming and expensive and therefore not suitable for large-scale population studies. Furthermore, none of these or any other reliable techniques exists for the assessment of Lp(a) subforms, in the experimental lab or for an automated laboratory.

Lp(a) levels in a patient are known to correlate strongly with cardiovascular and metabolic health in a patient. It is a goal of existing Lp(a) assays to determine concentration of Lp(a), described as particle number (PN) and generally expressed in nmol/L from a patient's bodily fluid sample, particularly from blood, serum or plasma. The levels of Lp(a) are generally stratified into risk classifications to determine a patient's health status, trends in health status, whether treatment is necessary, and to monitor treatment.

Additionally, the determination of apolipoprotein content in a patient is known to be useful in determining overall health and for guiding treatment. For example, apolipoprotein B (apo(b)) is known to be a risk factor of atherosclerosis independent of the lipoproteins to which it is linked. Apolipoprotein A (apo(a)) is another such protein with individual characteristics having significance for cardiovascular disease. Apo(a) partly comprises the Lp(a) particle and has a variety of subforms. Apo(a) subforms are derived specifically from the different possible repeated domains. It is composed of five domains called kringles (kringle I-V). Kringle IV is a repeating structure with from 3 to >50 subunit repeats on a single Apo(a) molecule. The number of repeats thought to exist is variable in literature. However, kringle IV is itself comprises 10 different sequence/structures that can be recognized. Kringle IV type 2 is the one that repeats. The number of kringle IV type 2 ($KIV_2$) repeats gives a molar mass of the total protein anywhere from 200 kDa to 800 kDa. The weight of the apo(a) protein translates to variation in the Lp(a) lipoprotein, which is composed of the lipid particle, one apo(b) protein and one apo(a) protein.

Although there have been recent improvements in quantifying particle numbers of the various lipoprotein particles, particularly Lp(a) (see, e.g., Marcovina et al., "Effect on the Number of Apolipoprotein(a) Kringle 4 Domains on Immunochemical Measurements of Lipoprotein(a)," *Clin. Chem.* 41(2): 246-255 (1995)), particle numbers are only one factor in the health effects of Lp(a). It has been determined that the Lp(a) mass is also a factor.

Markovina established the effect of the number of apo(a) Kringle 4 domains on immunochemical measurements of Lp(a), and that a larger apo(a) from more Kringle 4 repeats contributed to an overcounting of the Lp(a) particles (see Marcovina et al., "Effect on the Number of Apolipoprotein (a) Kringle 4 Domains on Immunochemical Measurements of Lipoprotein(a)," *Clin. Chem.* 41(2): 246-255 (1995)).

Existing assays such as the Denka Seiken Lp(a)-latex assay, based on the Markovina work have been designed to measure the Lp(a) concentration (particle number) via immunological detection to minimize the kringle repeat size problem. This method, however, may still be subject to interference by the variable number of apo(a) kringle 4 type 2 repeats, as it uses one antibody directed to the variable size kringle 4 type 2 domain. Furthermore, the method fails to characterize Lp(a) masses and mass distribution.

Improvements are needed to permit efficient and cost-effective identification of Lp(a) subforms. Existing immunological methods such as Denka Seiken are drawn only to the measurement of particle number and have no consideration of the Lp(a) mass. A full characterization would involve at least two assays to generate a complete measurement of Lp(a) measurement: first an apo(a) protein mass assay and second a molecular weight determination of the subform by amino acid analyzer or gradient gel electrophoresis.

A solution to this problem described herein relies on application of electrophoresis. Electrophoresis is the separation of charged molecular species based on the size and/or ionic charge of the molecules in an electric field. This involves the migration of charged species through an electrophoretic matrix in some cases or a buffer solution in a capillary in others, under an electric field generated by activated electrodes. Biological molecules, including proteins, amino acids, and nucleic acids, possess ionizable groups that cause the molecules to migrate as charged particles in an electric field. Various forms of electrophoresis are known, including gel electrophoresis, free zone electrophoresis, isoelectric focusing, and isotachophoresis (CE-ITP). Separation of lipoproteins by capillary electrophoresis is an effective technique for accurately detecting the lipid particles and relative subfractions. However, this method is limited by a lack of effective and scalable methods to calculate lipid particle concentrations.

CE-ITP is an electrophoretic technique wherein the sample ions are separated under an electric field across a length of tubing or capillary containing the unknown sample and a buffer solution. The electric field causes the sample ions to be separated based on net electrical charges of the molecules. Similar substances react to the electrical attraction in the same way, and become focused into distinct groups or zones as they progress along the capillary. The liquid plug of sample to be separated is bounded by a leading buffer on one end and a trailing buffer on the other end. The leading and trailing buffers maintain the sample between them, enhancing the separations resolution. During migration through the capillary, the sample focuses into bands based on electrophoretic mobility. The bands can be distinguished by various techniques including UV light absorption, native fluorescence directly in the capillary or after elution from the capillary by subsequent gel or immunological detection.

CE-ITP has been used to separate plasma lipoproteins in preparation for subsequent analysis on a gradient gel (see Bottcher et al., "Automated Free-Solution Isotachophoresis: Instrumentation and Fractionation of Human Serum Proteins," *Electrophoresis*. 19(7): 1110-6 (1998) and Bottcher et al., "Preparative Free-Solution Isotachophoresis for Separation of Human Plasma Lipoproteins: Apolipoprotein and Lipid Composition of HDL Subfractions," *J Lipid Res*. 41(6): 905-15 (2000)). In particular, Bottcher describes that sample components were separated from one another using spacers. Analysis required use of a transfer gel, gradient gel electrophoresis and western blotting for detection. However, this and other current capillary isotachophoresis methods do not permit the quantification of molar quantities of the lipoproteins, which is a more accurate predictor of the levels of lipoprotein subparticles, and the risk of developing a disease.

No study has been able to incorporate particle separation and detection on a single instrument in an automated format. Nor does any study or technique exist to characterize the Lp(a) subforms in a patient sample. Additional substrates, transfer steps, and detection modes in an assay severely limit possible attempts. Furthermore, limitations on the detectable analytes fail to offer sufficient information for health assessment. Resolution in the existing methods fails to offer insight in lipid particle subclass or variant characterization.

This present invention is directed to an efficient single assay that can be used to determine Lp(a) mass, mass distribution, distinction between Lp(a) subforms, and particle number, curing deficiencies in the art.

SUMMARY

Use of a capillary electrophoresis isotachophoresis laser induced fluorescence (CE-ITP-LIF) system for Lp(a) analysis can produce superior apo(a) variable subform Lp(a) particle identification than has been demonstrated on previous systems, including zonal gels, a precursor electrophoretic technique described in US Patent Application Publication No. 20140243431, incorporated herein by reference in its entirety. The ability to separate HDL and LDL subset particles by CE-ITP demonstrates the charge/mass separating power of this platform and apo(a) subform identification is practicable and superior to zonal separations.

One aspect of the invention relates to a method for determining the concentration of a lipoprotein(a) subform in a biological sample. The method involves contacting a biological sample with a signal-producing moiety under conditions suitable for a signal-producing moiety to bind to a lipoprotein(a) subform in the biological sample to form a moiety-bound sample. The method also involves depositing a fraction of the moiety-bound sample in a capillary electrophoresis system; separating components of the fraction via capillary isotachophoresis; and detecting signals produced by the signal-producing moiety. The method further involves quantifying, based on said detecting, the concentration of the lipoprotein(a) subform in the sample, wherein the detected signals are proportional to the molar concentration of the lipoprotein(a) subform in the fraction.

A second aspect of the invention relates to a method for determining the particle number of a lipoprotein(a) subform in a biological sample. The method involves contacting a biological sample with a signal-producing moiety under conditions suitable for a signal-producing moiety to bind to lipoprotein(a) subforms in the biological sample to form a moiety-bound sample. The method also involves depositing a fraction of the moiety-bound sample in a capillary electrophoresis system; separating components of the fraction via capillary isotachophoresis; and detecting signals produced by the signal-producing moiety. The method further involves quantifying, based on said detecting, the particle number of the lipoprotein(a) subform in the sample, where the detected signals are proportional to the particle number of the lipoprotein(a) subform in the fraction.

A third aspect of the invention relates to a method of assessing cardiovascular risk in a subject. The method comprises (i) determining particle number and/or molar mass of a lipoprotein(a) subform in a biological sample from a subject and (ii) assessing the cardiovascular risk of the subject based on the particle number and/or molar mass of the lipoprotein(a) subform. Determining the particle number and/or molar mass of the lipoprotein(a) subform involves (a) contacting the biological sample with a signal-producing moiety under conditions suitable for the signal-producing moiety to bind to the lipoprotein(a) subform to form a moiety-bound sample; (b) depositing a fraction of the moiety-bound sample in a capillary electrophoresis system; (c) separating components of the fraction via capillary isotachophoresis; (d) detecting signals produced by the signal-producing moiety; and (e) quantifying, based on said detecting, the particle number and/or molar mass of the lipoprotein (a) subform in the sample, where the detected signals are proportional to the particle number of the lipoprotein(a) subform in the fraction.

BRIEF DESCRIPTION OF THE DRAWINGS

FIGS. 5A-5C show the analysis of collected pixel data. FIG. 5A is a typical electropherogram from a single pixel of the PDA used to build up the Equiphase map shown in FIG. 5B. Each point of the Equiphase map represents a detected peak in space (pixel) and time (scan count). Tracking is performed to group sets of peaks into signal tracks, which travel in a straight line across the Equiphase map. FIG. 5C shows the fitting of such tracks with linear functions to give their velocities. Each black line in FIG. 5C represents a signal track; the gradient of the lines gives the velocity.

FIG. 6A shows an electropherogram of a control sample comprising CF in the absence of a biological sample. FIG. 6B shows the lipoprotein profile of several replicate biological samples prepared from patient 8 and spiked with CF. FIG. 6C shows that the lipid profile detected remains constant even after CF has degraded.

FIG. 7A shows an electropherogram of a native sample of patient 8 incubated with an HDL spike. FIG. 7B shows an electropherogram of a native sample of patient 8 incubated with an LDL spike. FIG. 7C shows an electropherogram of a HDL/VDL/LDL mixture from patient 8 incubated with a VLDL spike. The arrow indicated the possible location of the VDL peak.

FIG. 8A shows an alignment of electropherograms from samples prepared from LDL Patient 6 (top) and LDL Patient 4 (bottom). Gel images (not shown) indicate that the LDL 6 sample contains Lp(a) and that the LDL 4 sample does not. FIG. 8B shows the alignment of electropherograms from samples prepared from patients 1-6. Samples from Patients 1, 2, and 6 should contain Lp(a). Arrows indicate possible extra peaks which could indicate the presence of Lp(a). FIG. 8C shows 3 replicate electropherograms of the HDL sample from patient 6. FIG. 8D shows the alignment and normalization of electropherograms from HDL samples of patients 1-6. Electropherograms were normalized around the CF peak (arrow). FIG. 8E shows the alignment and reproducibility triplicate electropherograms from native samples.

FIGS. 9A-9F show electropherograms of biological samples from patients 1-6, respectively. FIG. 9G shows an alignment of the electropherograms collected for biological samples from patients 1-6, normalized around the CF peak. Corrected peak areas are shown in the figure. Arrows indicate peaks corresponding to CF and LDL peaks.

In FIG. 11A, a series of samples have been run on a gel in parallel. The cathode and anode ends of the gel are labeled and solid lines represent the position of Lp(a) particles after separation where apo(a) mass is about 600-650 kD, that distinguishes large (anodal) from small (cathodal) particles. Four samples have been highlighted (sample numbers 10, 73, 24, and 44). These samples show distinct Lp(a) subform size difference due to the migration rates of smaller subforms (samples 10 and 73) and larger subforms (samples 24 and 44). FIGS. 11B and 11C show additional examples of the Lp(a) particle migration differentials using gel electrophoresis. Zonal gels run in parallel show variation among patient samples in a high-throughput experiment (FIGS. 11B,C). High-throughput involves the parallel analysis of a multiplicity of samples on automated instrumentation. Anodal particles of more than about 350 kD and cathodal particles of less than about 600 kD are identified. Anodal samples include sample numbers 1147, 1200, 0481, 1621, 2420, 2495, and 2618. Cathodal samples include sample numbers 1101 and 2611.

In FIG. 13, samples 24, 73, 44, and 10 are further analyzed in a western blot analysis after apo(a) removal from the Lp(a) particles. Western blot analysis was carried out using standard protocols with apo(a) Isoform Analysis (AAISO), using the Novex WesternBreeze Chromogenic Western Blot Immunodetection Kit (Invitrogen Life Technologies). Multiple reference standards intersperse the variable lanes. Sample 24, which is an anodal (or larger) Lp(a) particle, exhibits a larger separated apo(a)

in the western blot, appearing at around 700 kD and greater than 700 kD. Sample 73, which is a cathodal, (or a smaller particle in the zonal gel) corresponds to a smaller apo(a) protein around 600 kD in the western blot. Samples 44 and 10 repeat the pattern with an anodal Lp(a) similarly having larger apo(a) bands at 700 kD and a cathodal Lp(a) having a smaller apo(a) band at less than 450 kD on the western blot. "DBL" indicates the presence of two apo(a) isoforms in a lane.

Figure 13:
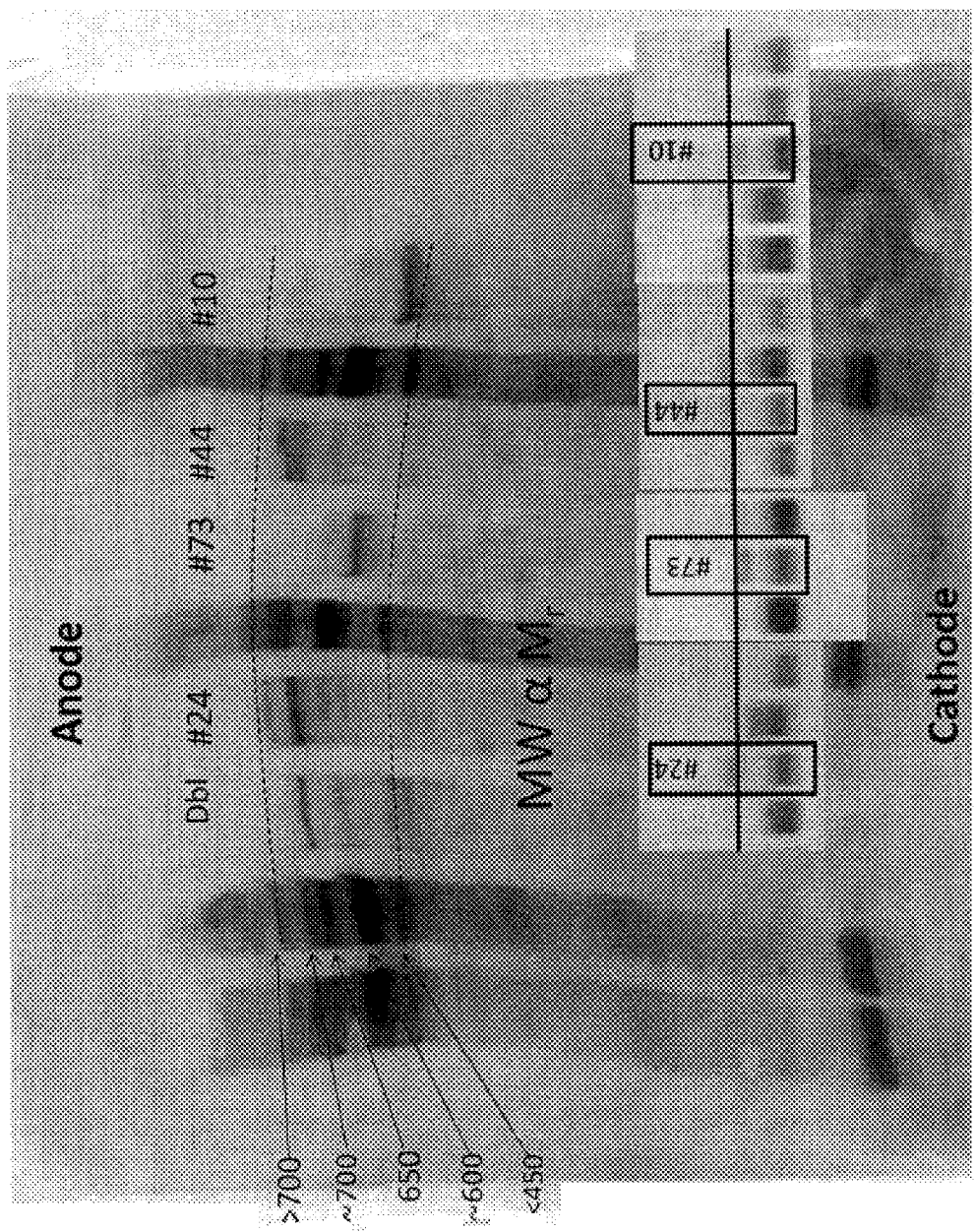
FIG. 13 compares the zonal gel shown in FIG. 11A to the same samples in a western blot.
Figure 14A:
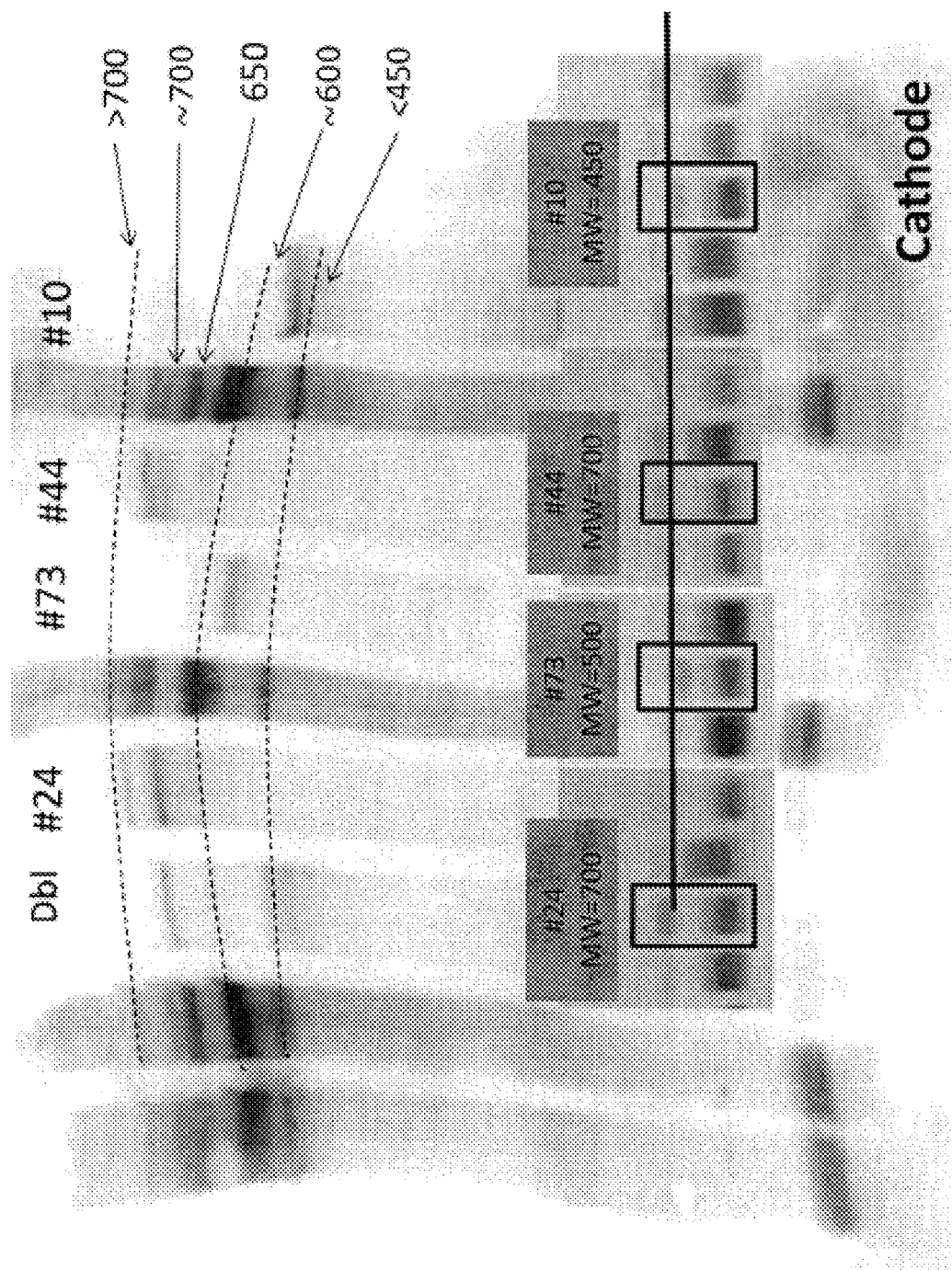
Figure 14B:
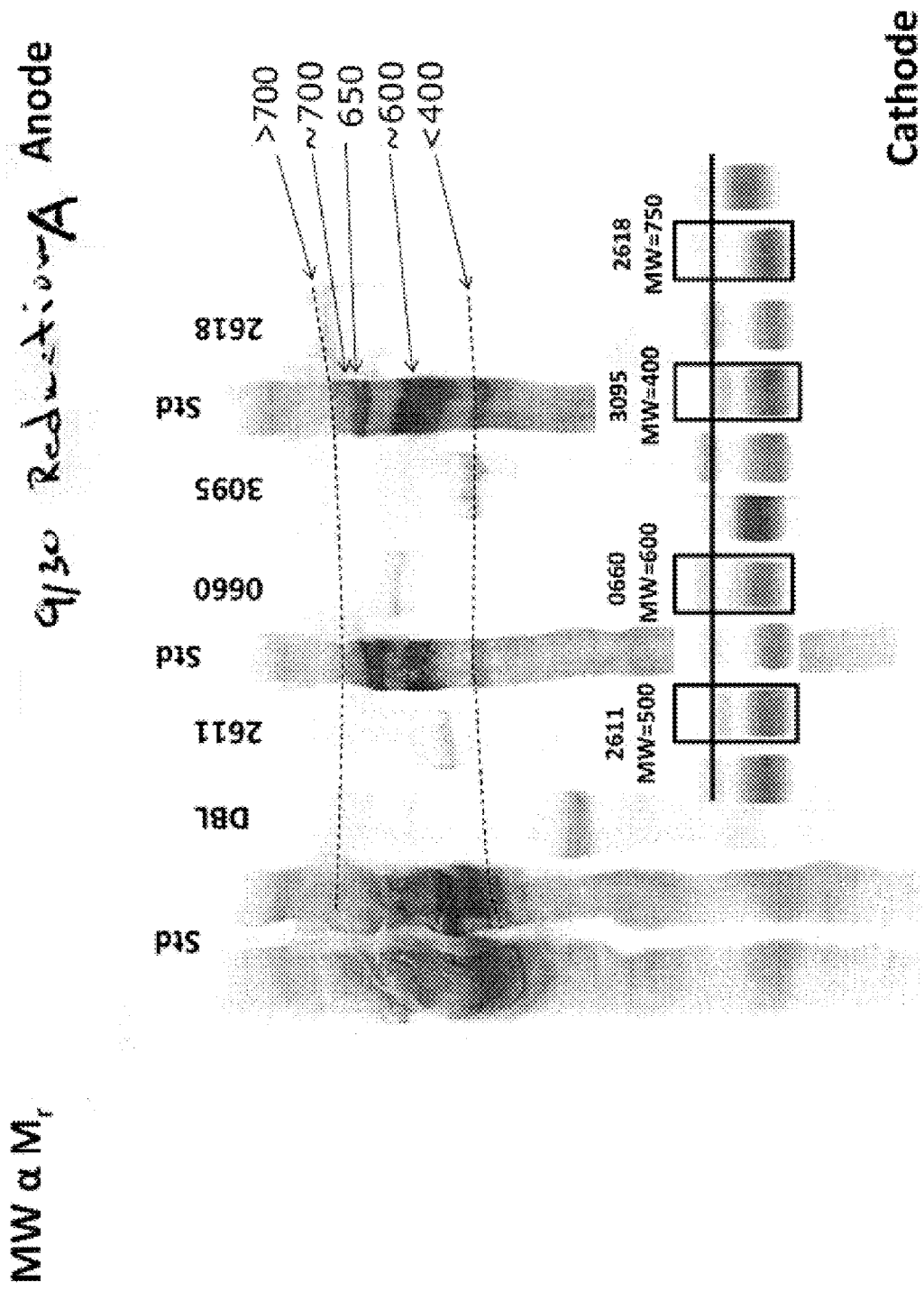
Figure 14C:
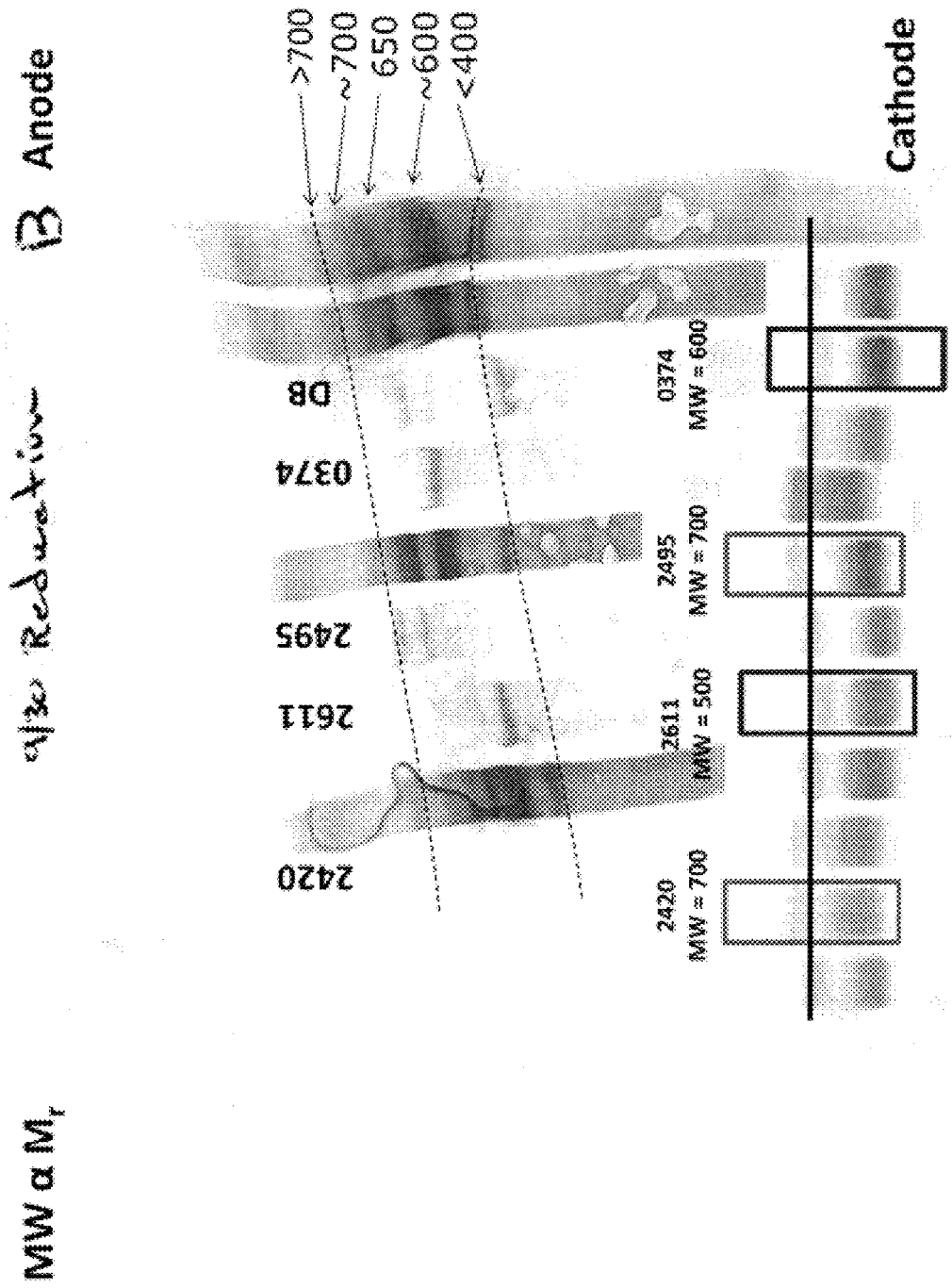
Figure 14D:
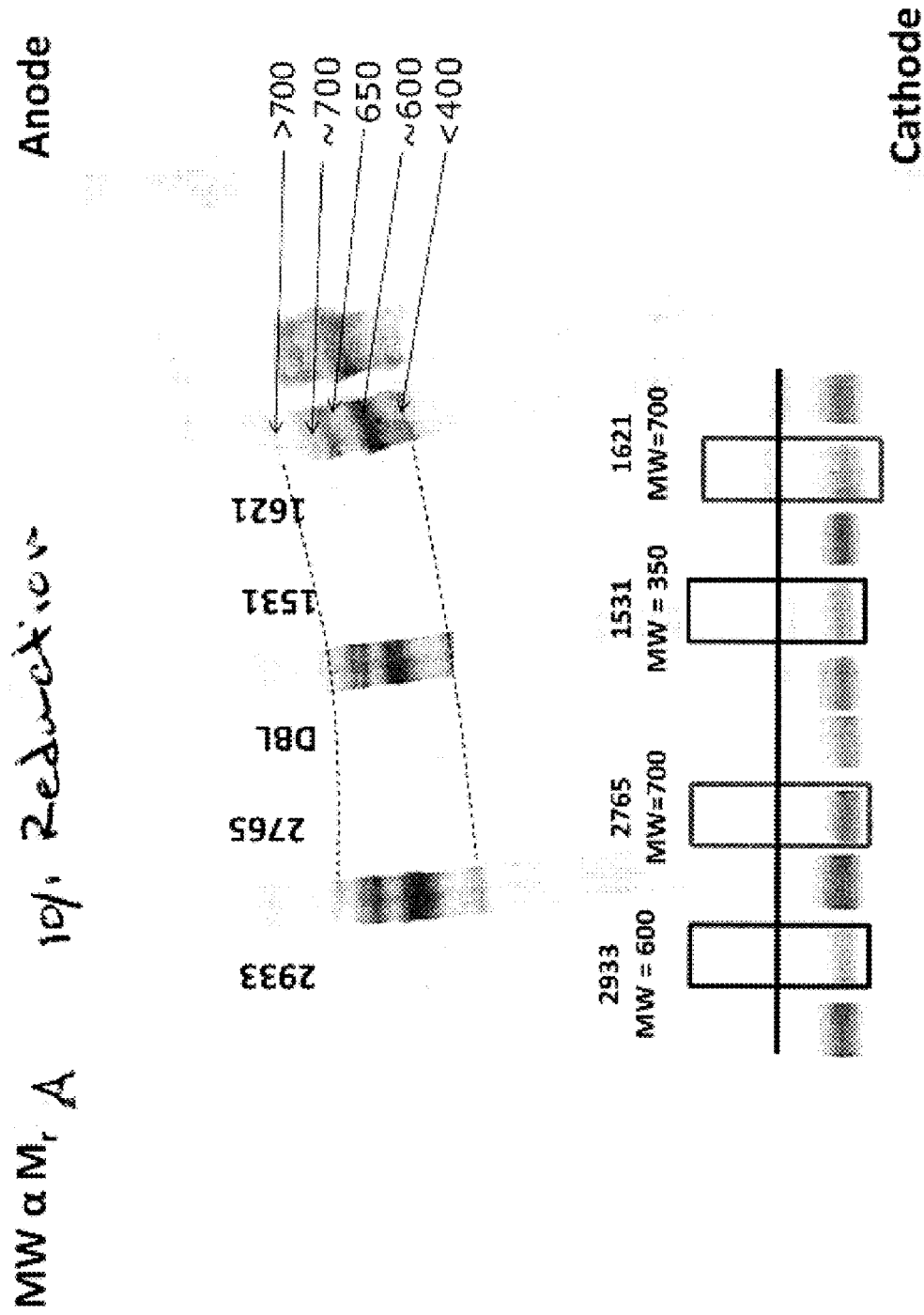
Figure 14E:
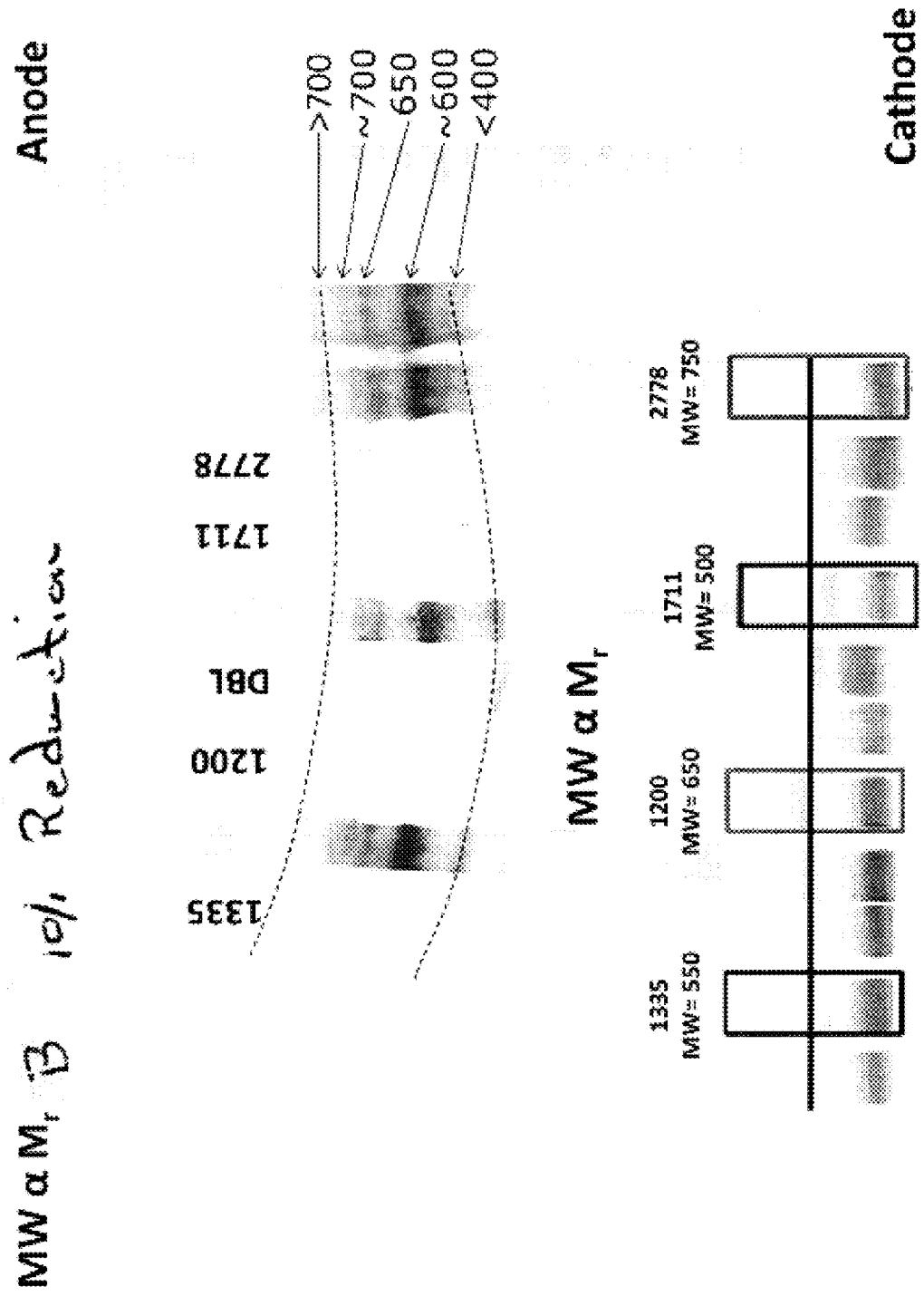
Figure 14F:
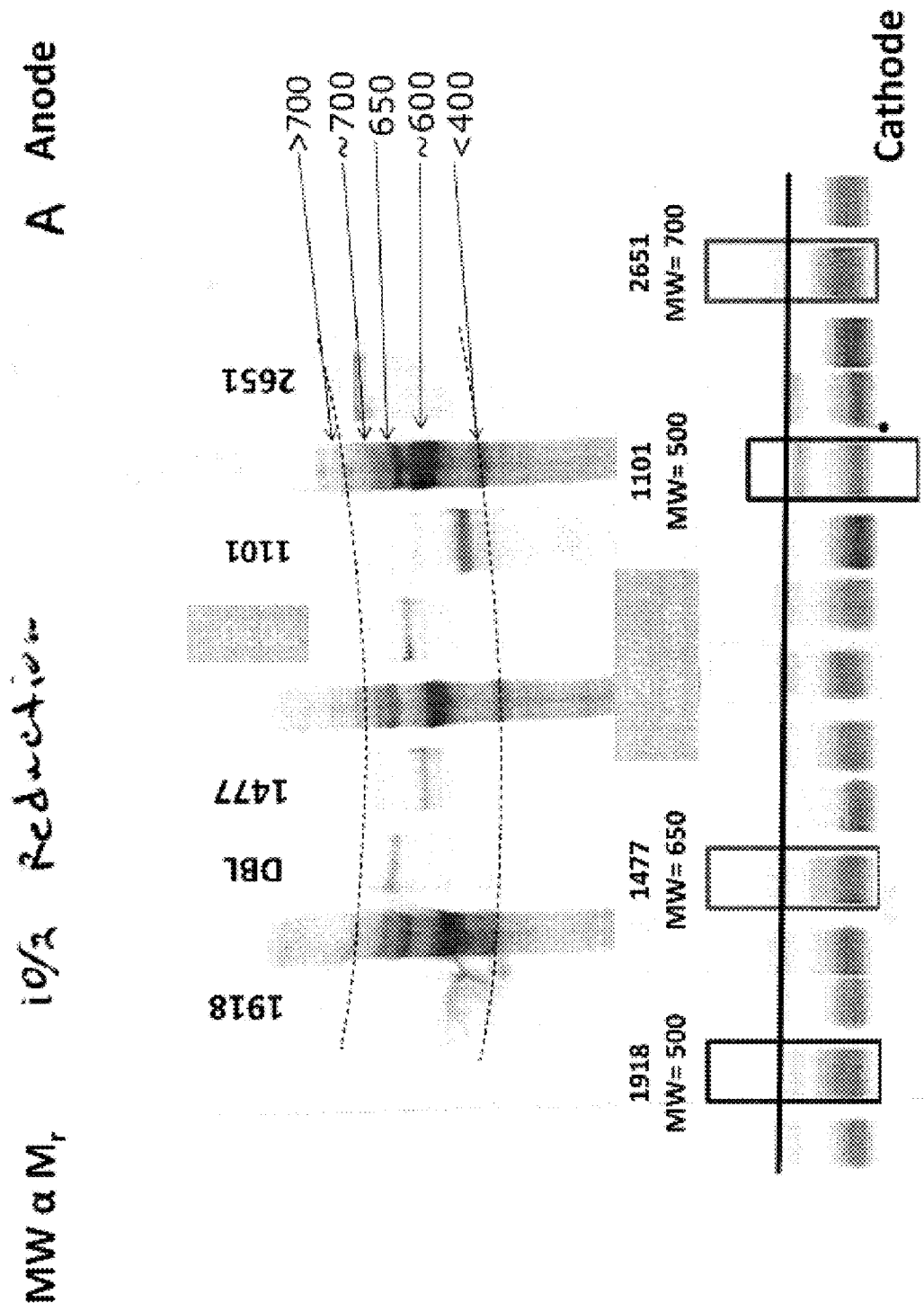
Figure 14G:
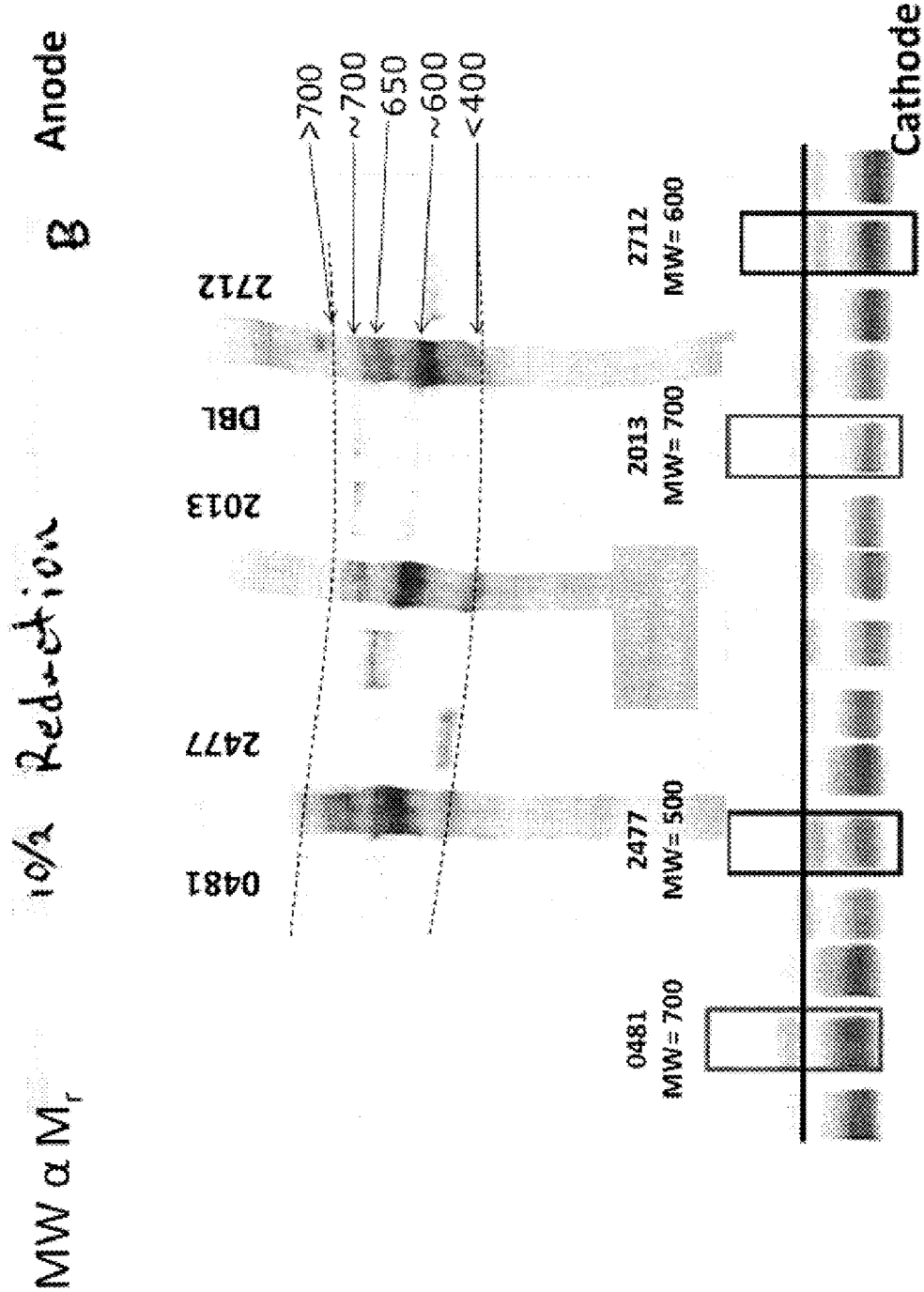
Figure 14H:
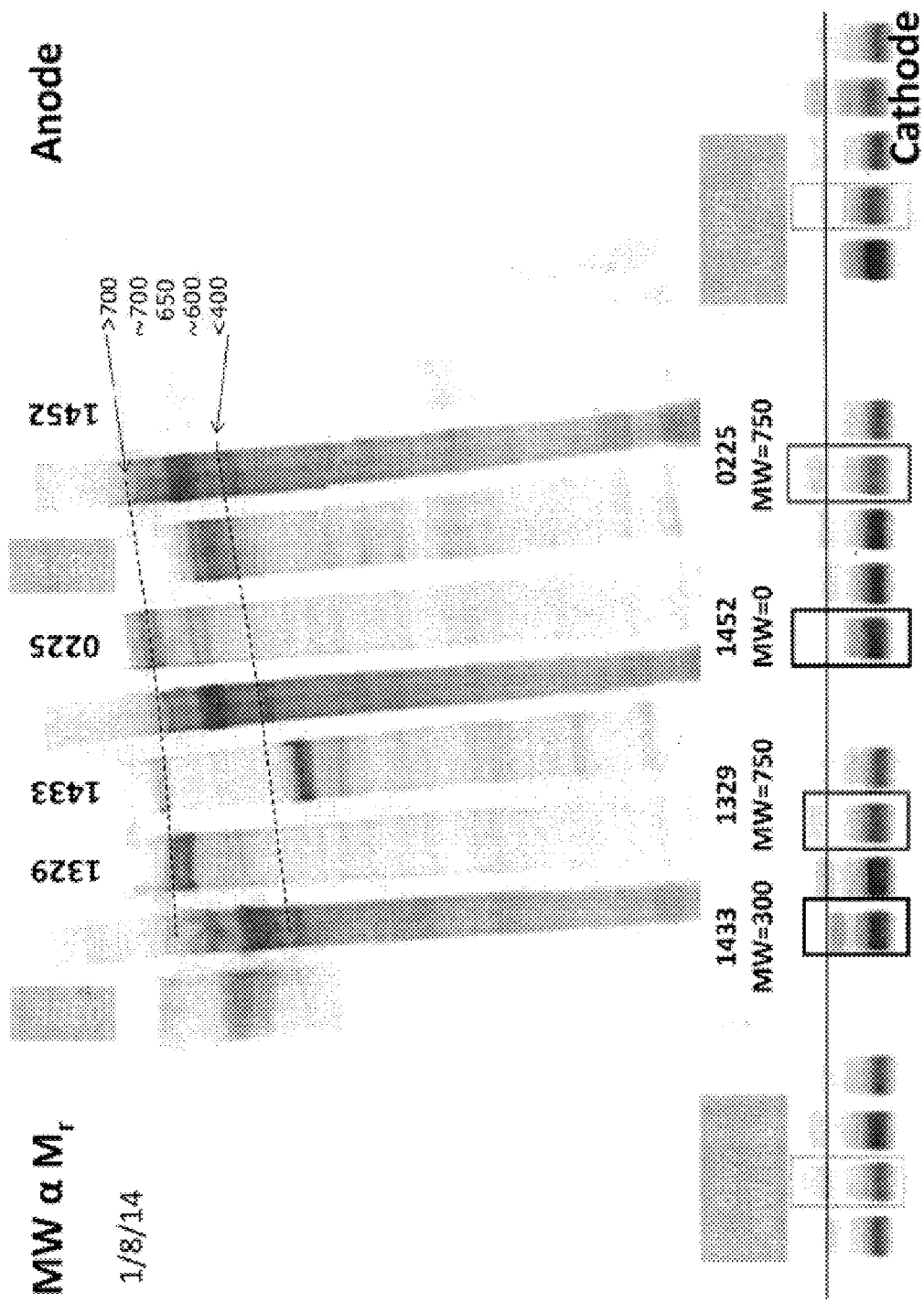
Figure 14I:
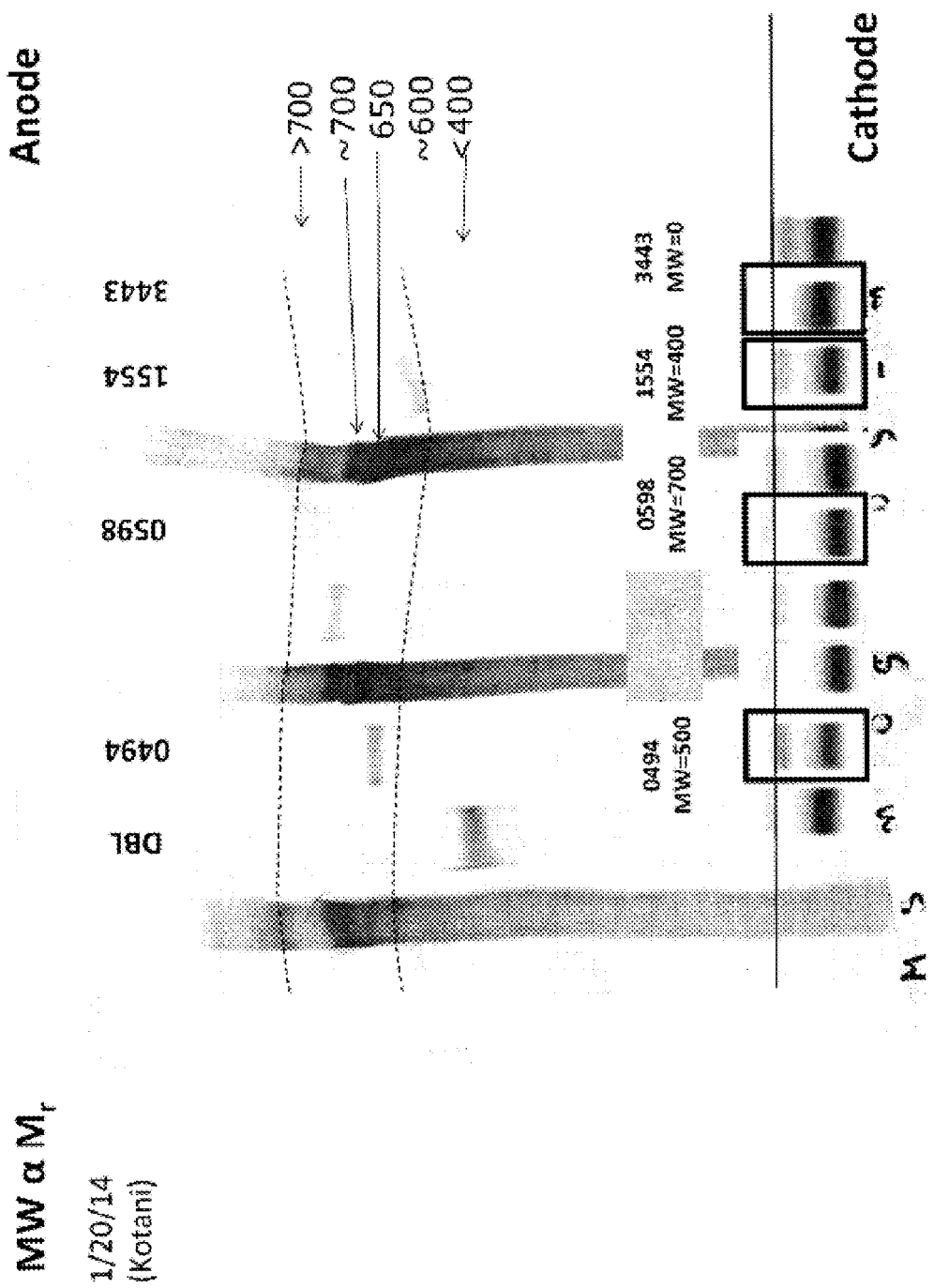
Figure 14J:
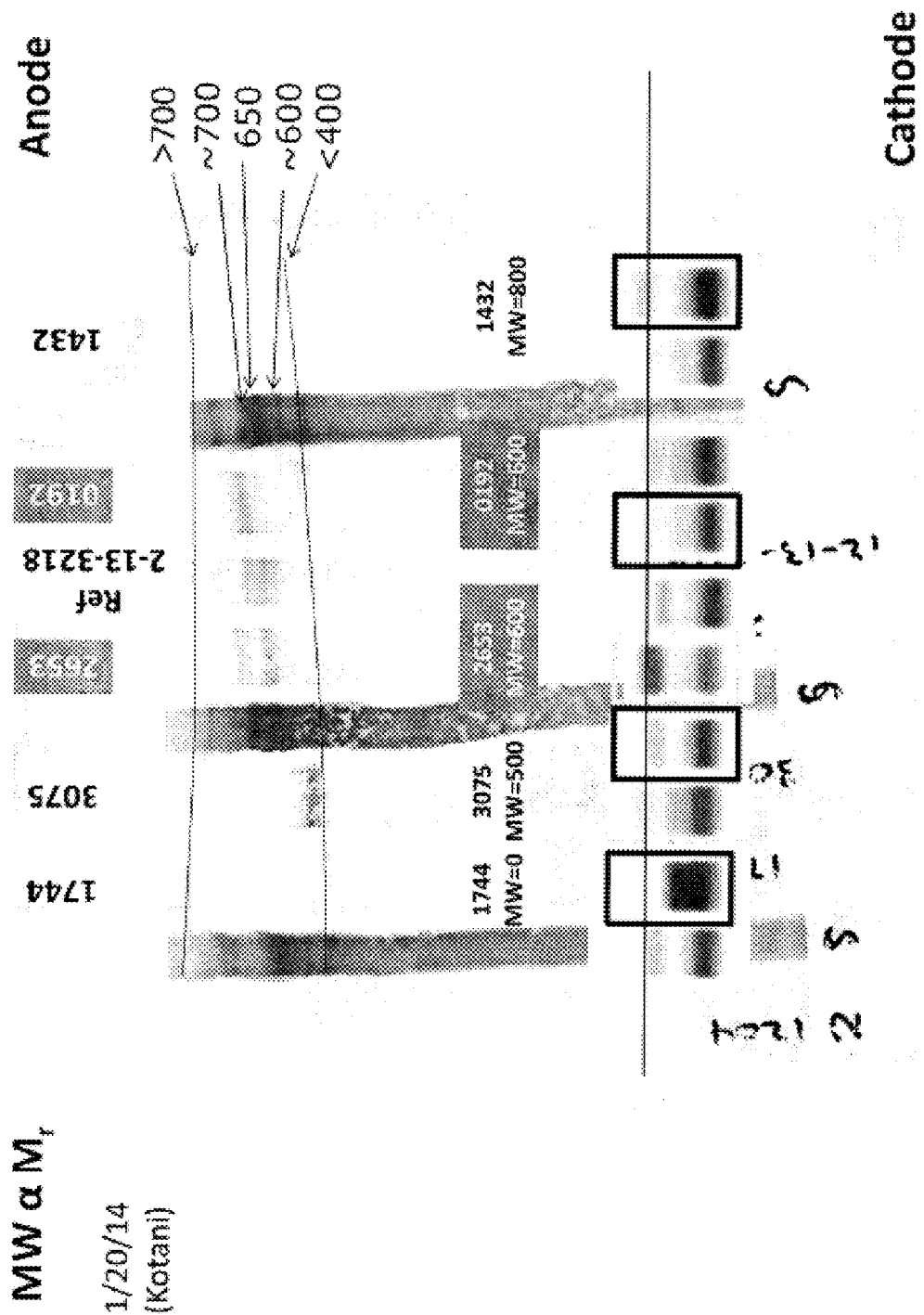
Figure 14K:
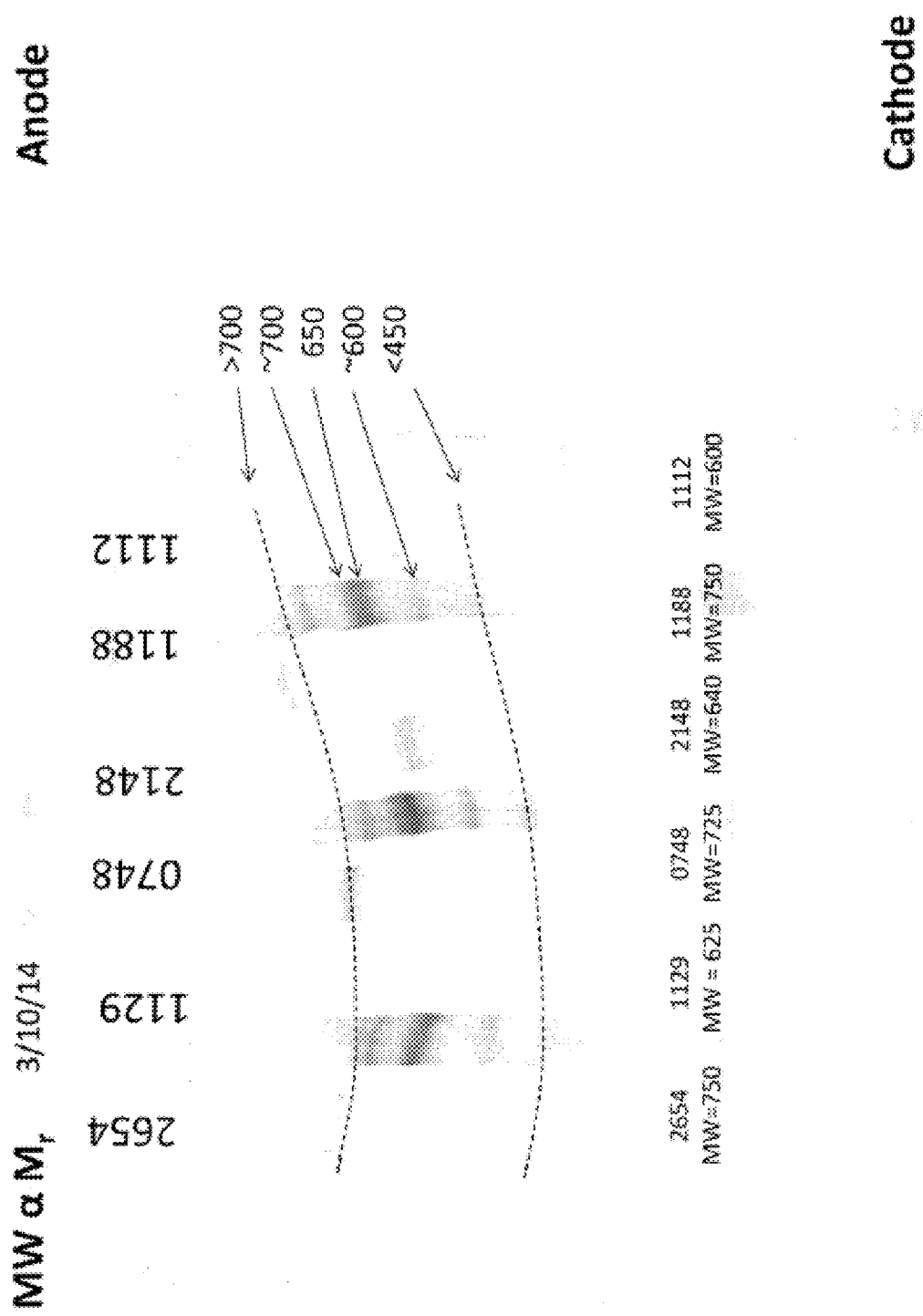
Figure 14L:
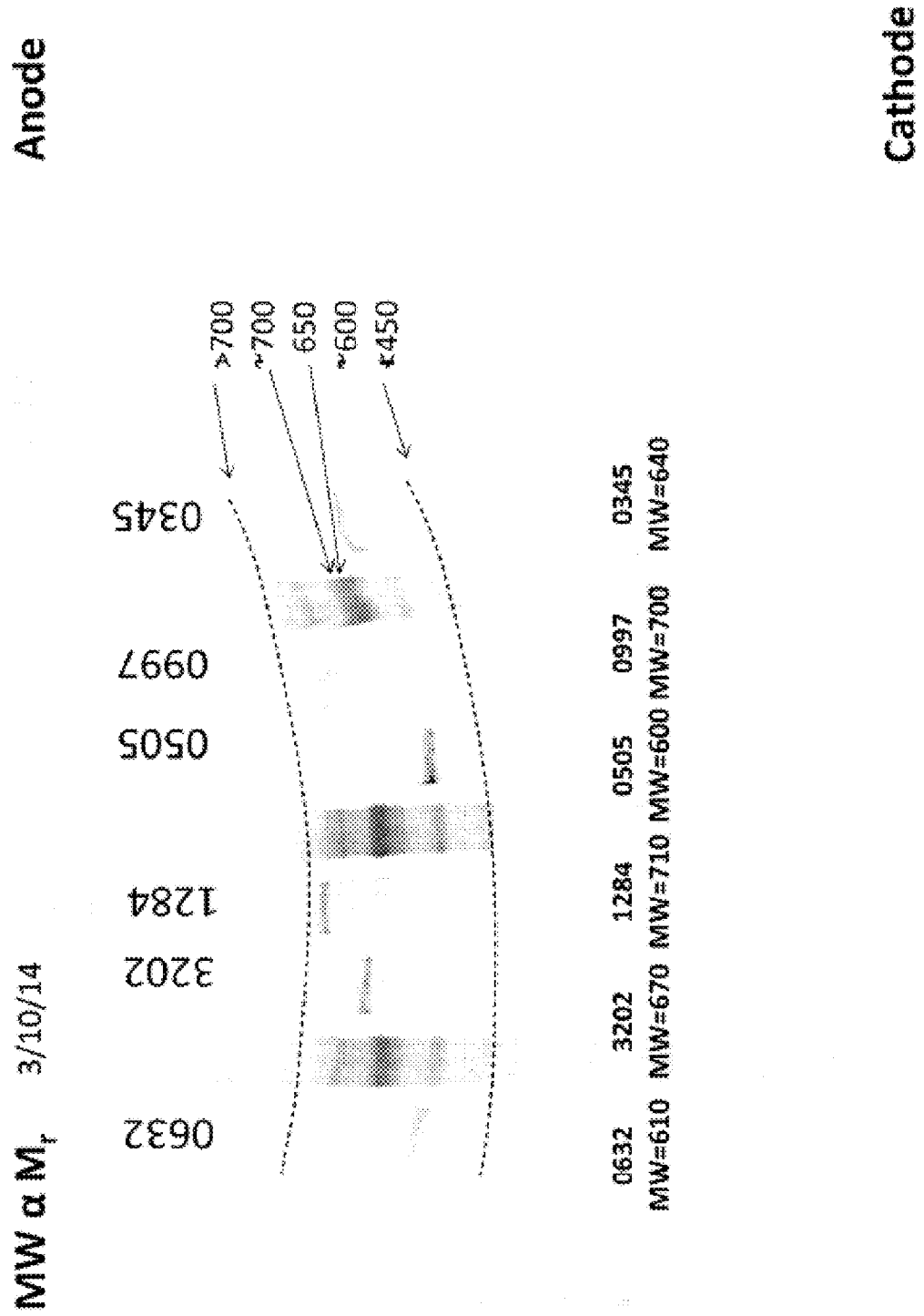
Figure 14M:
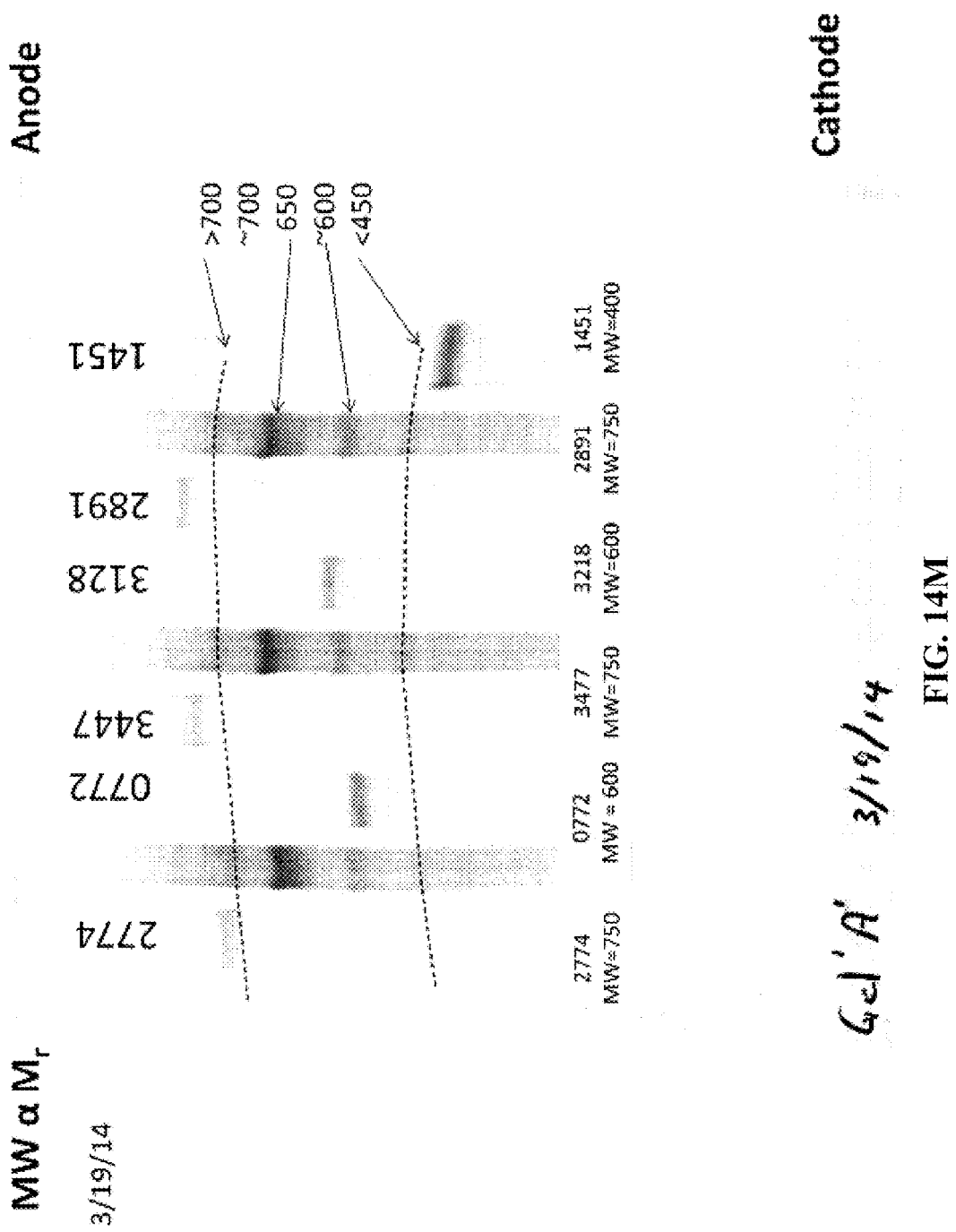
Figure 14N:
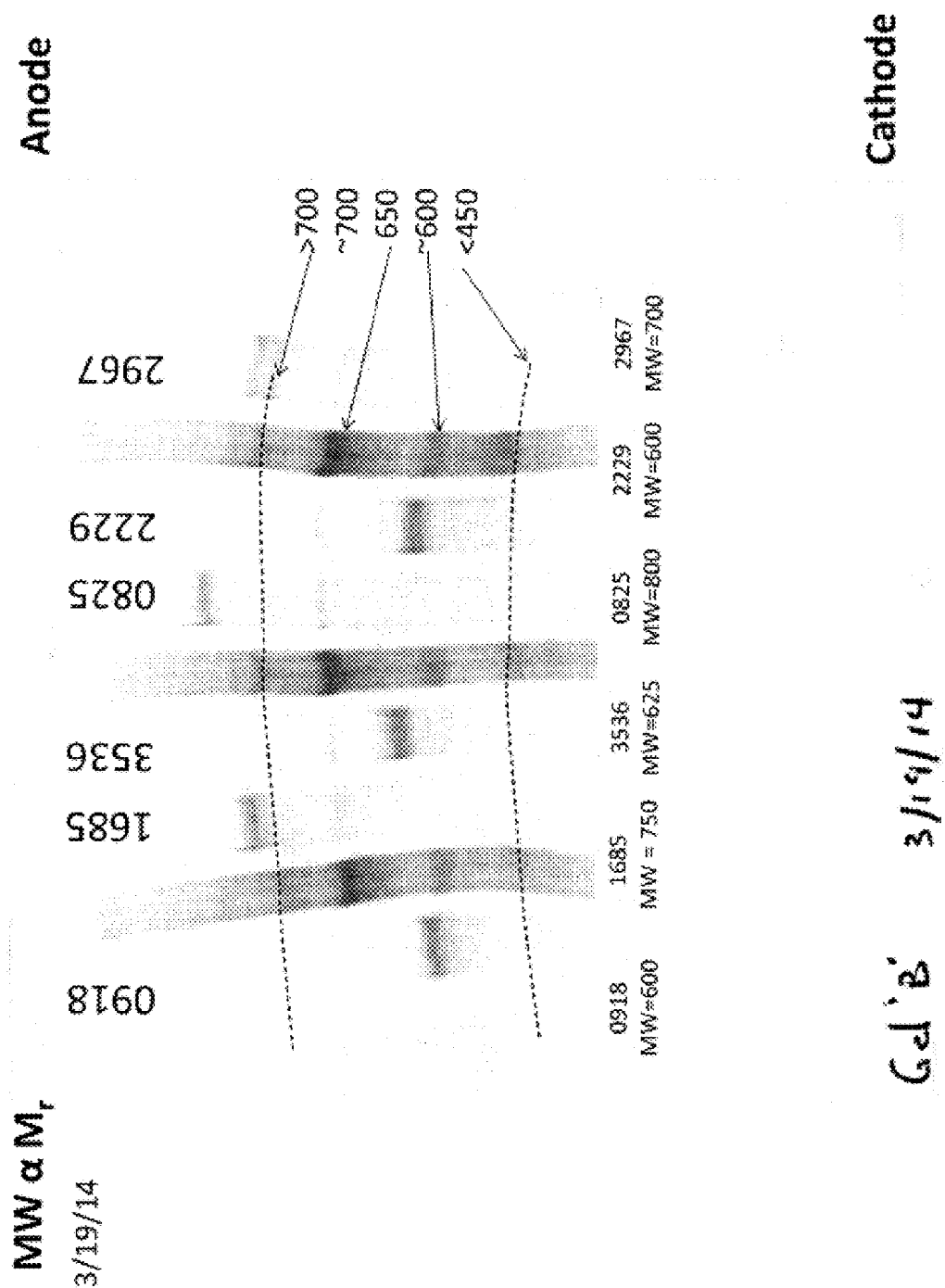
Figure 14O:
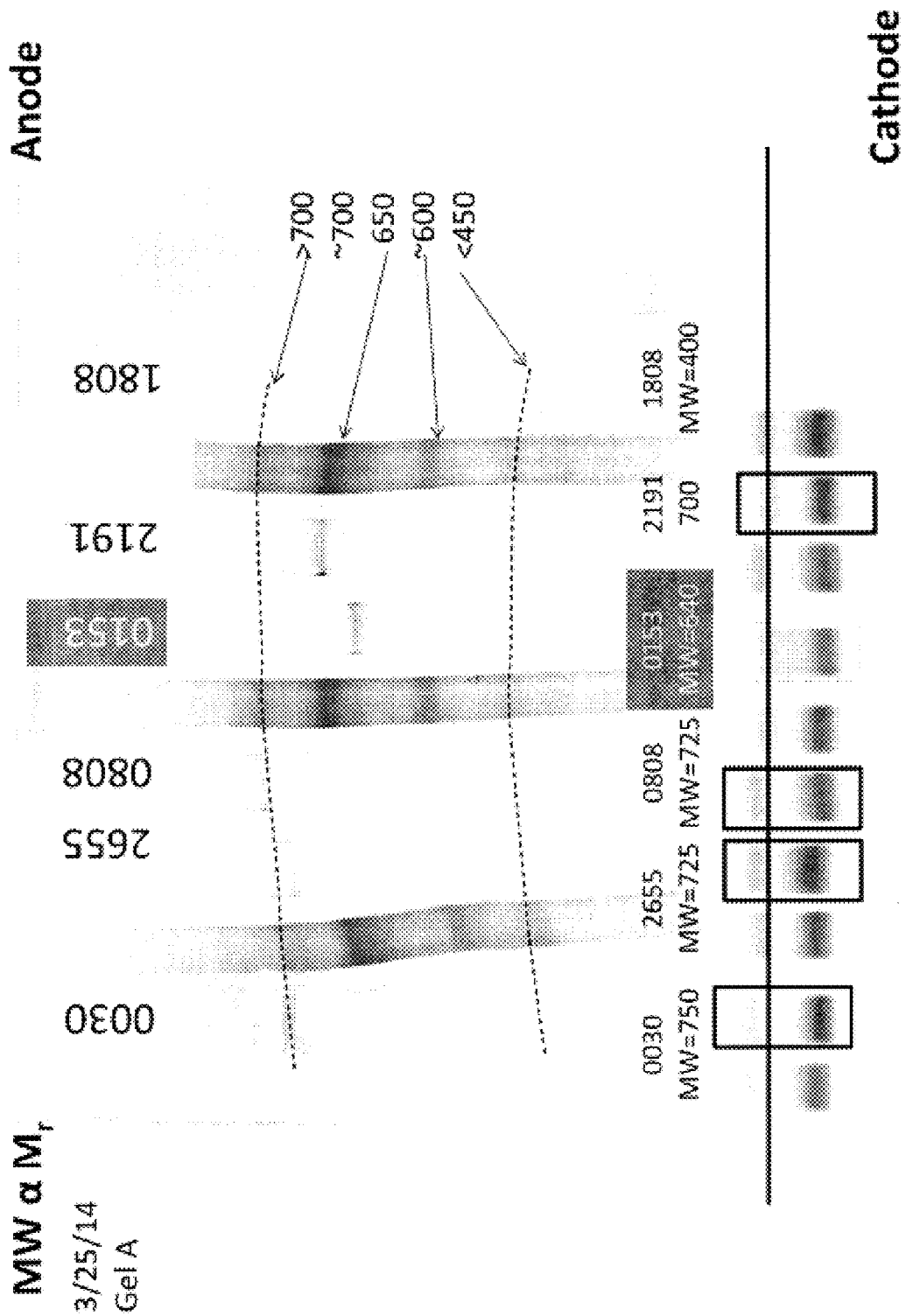
Figure 14P:
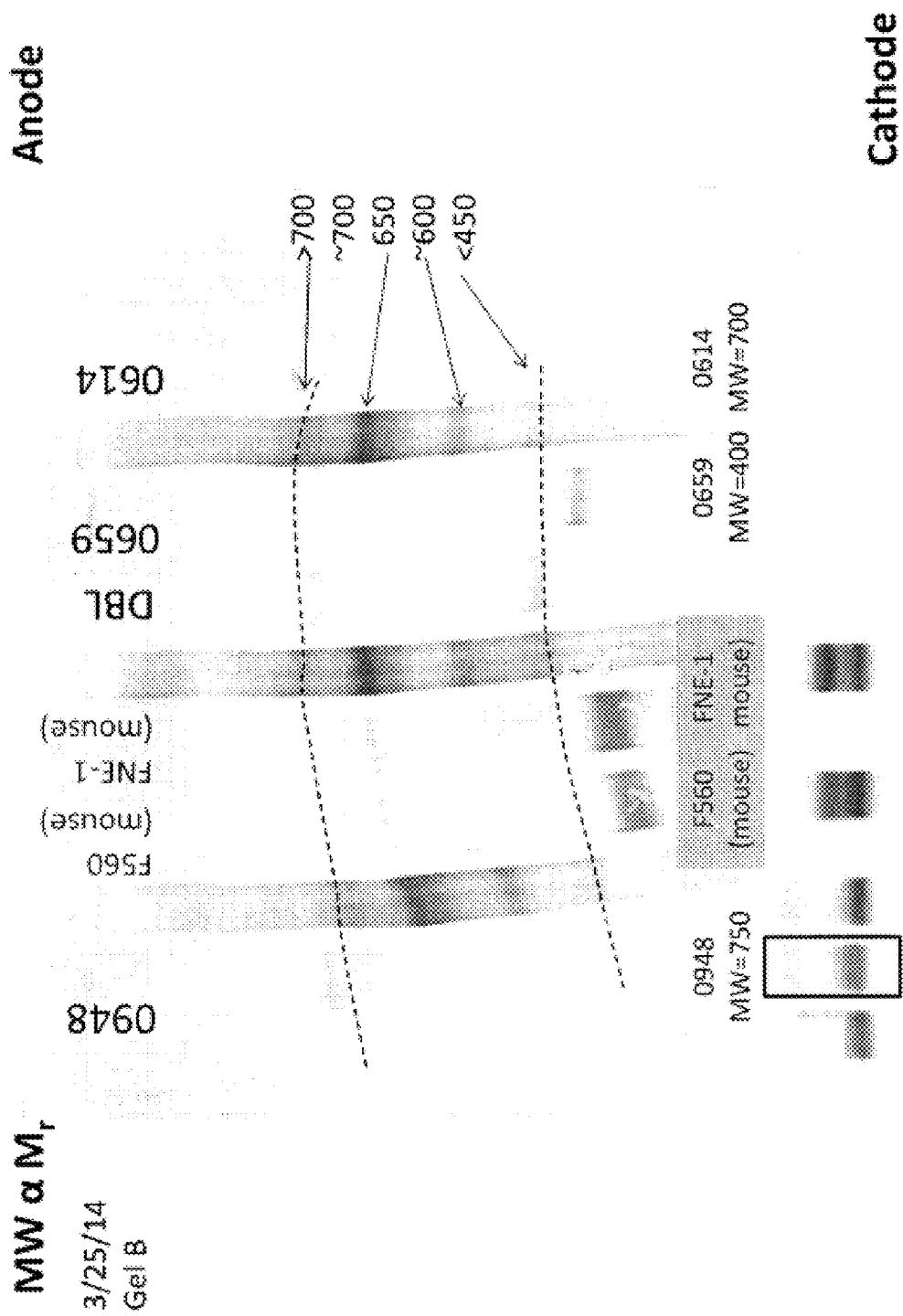
Figure 14Q:
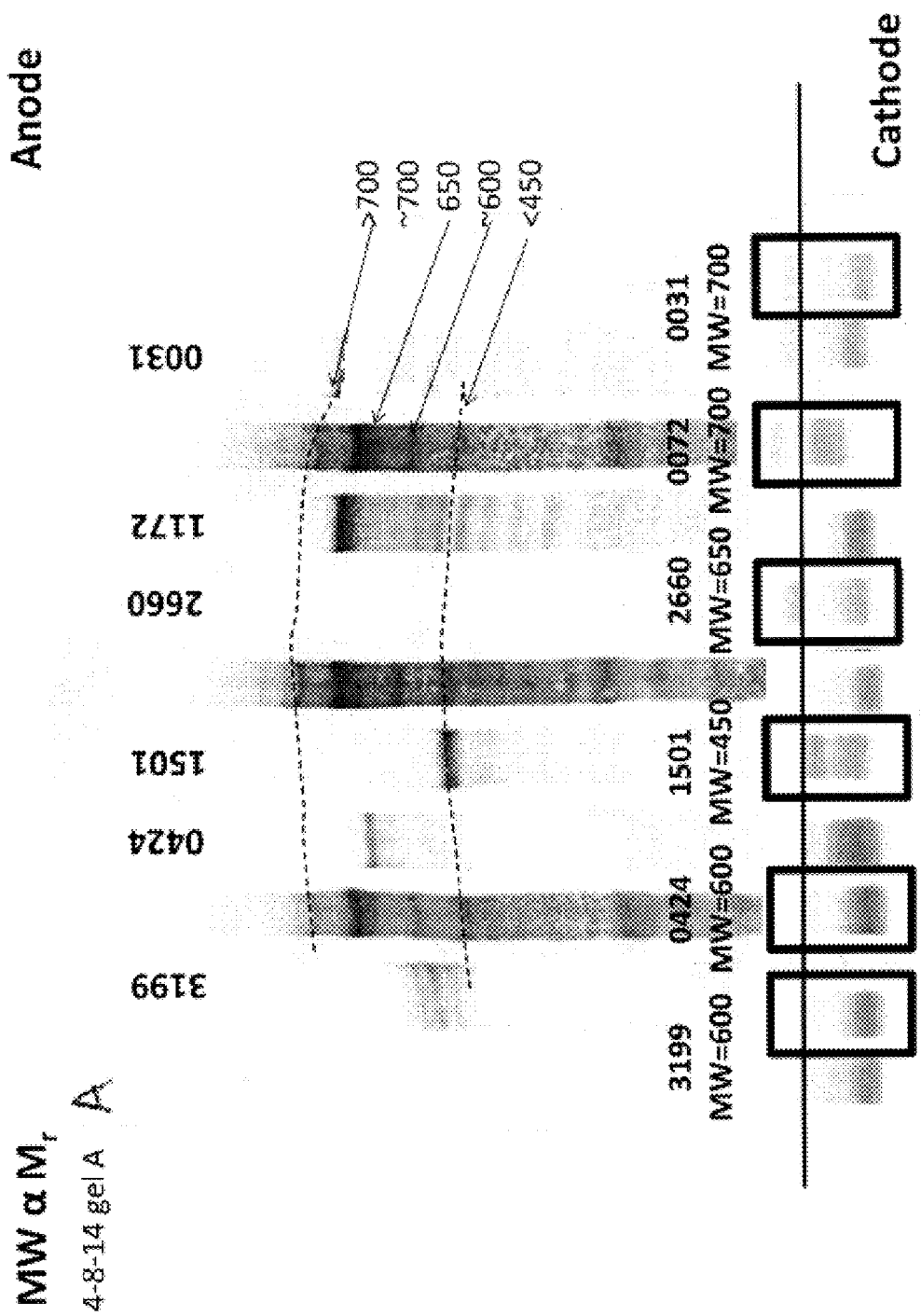
Figure 14R:
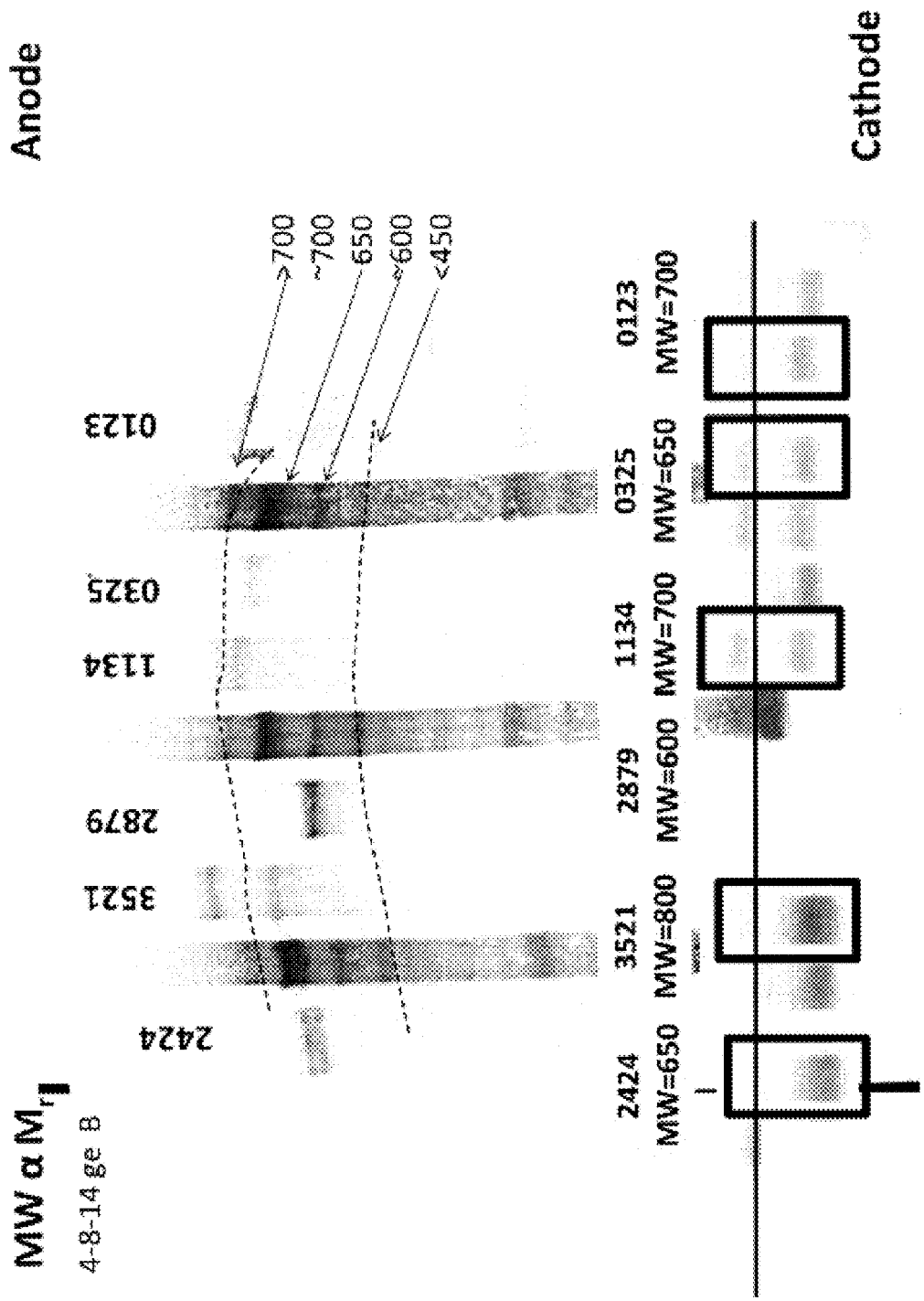
Figure 14S:
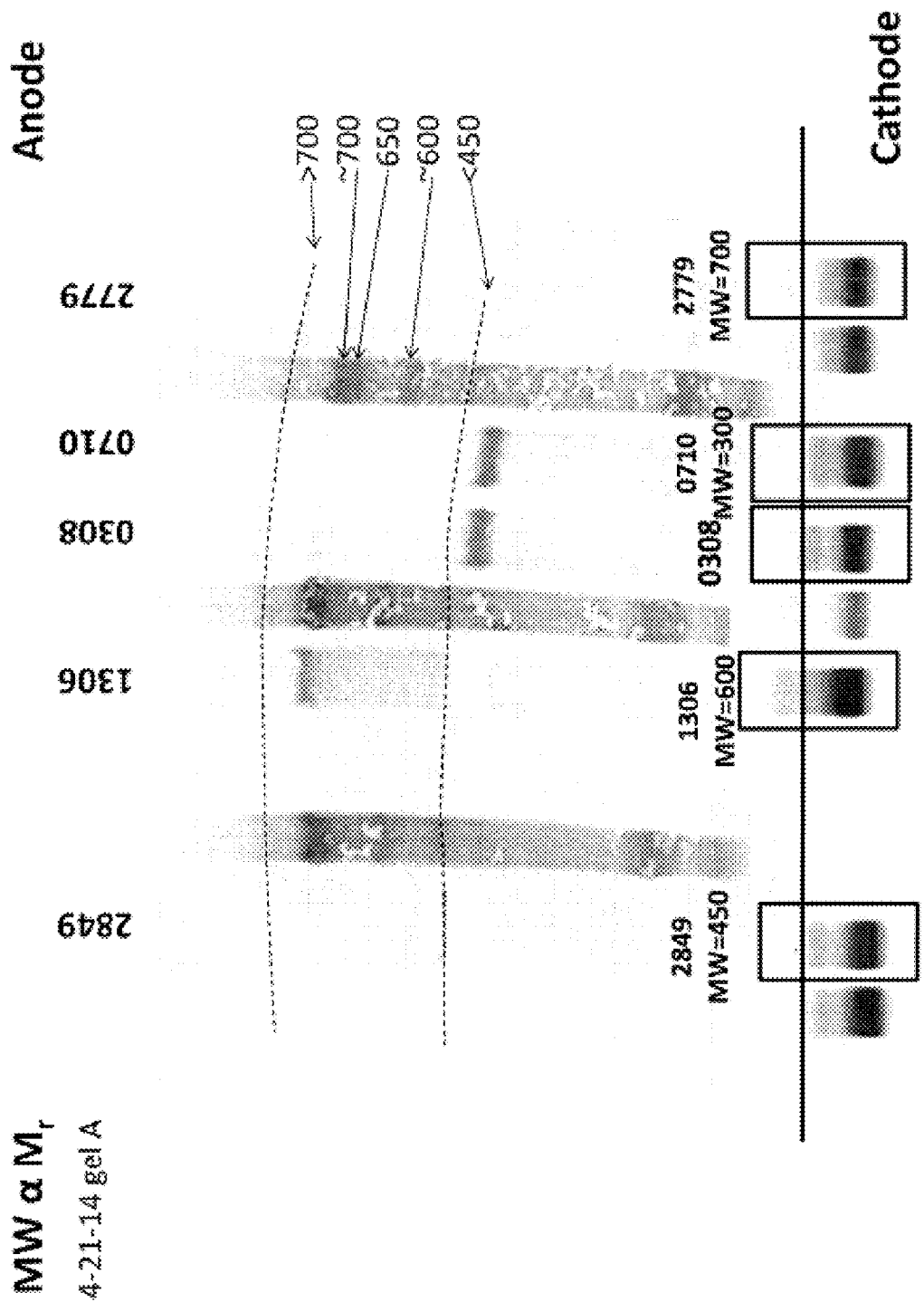
Figure 14T:
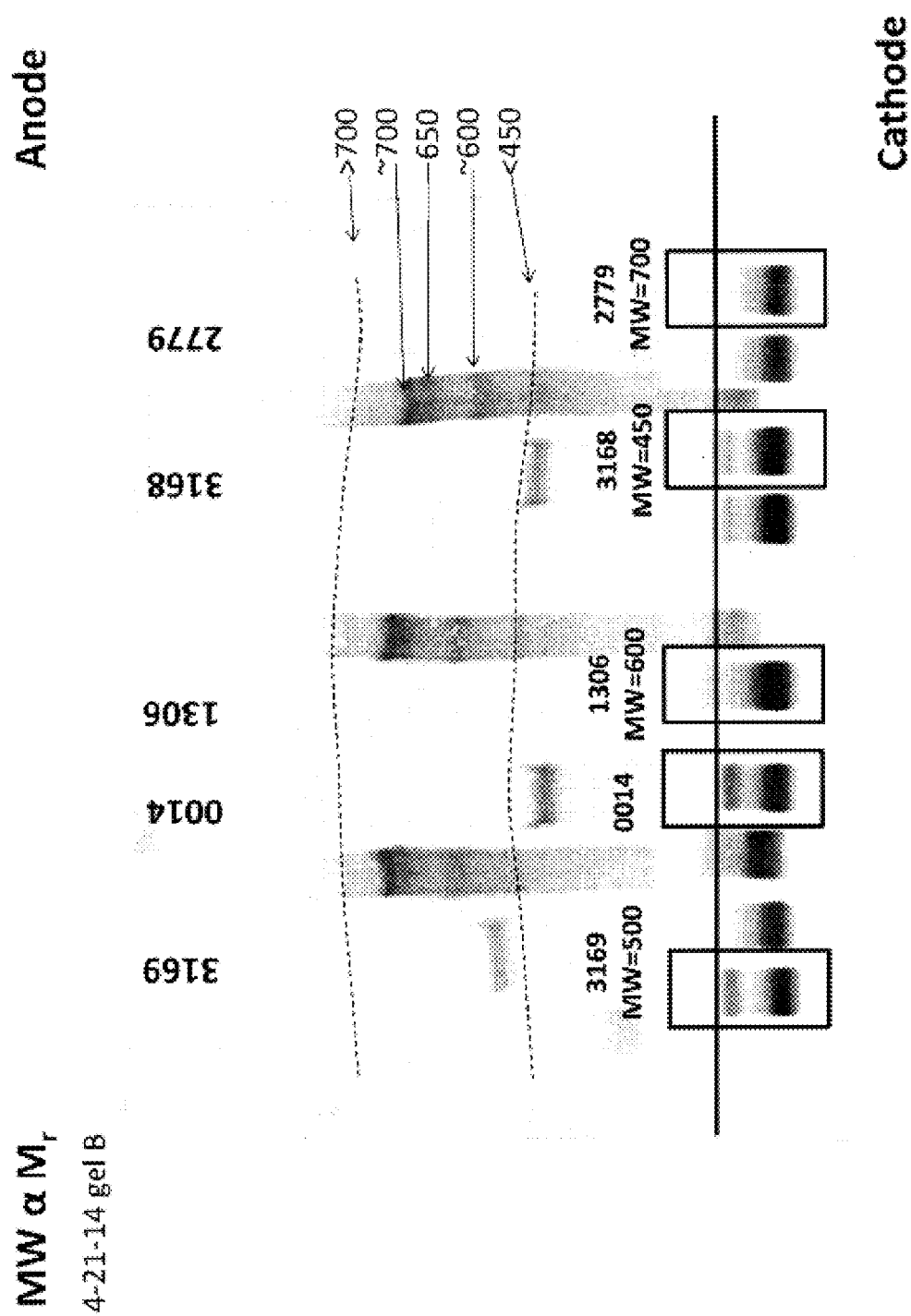
Figure 14U:
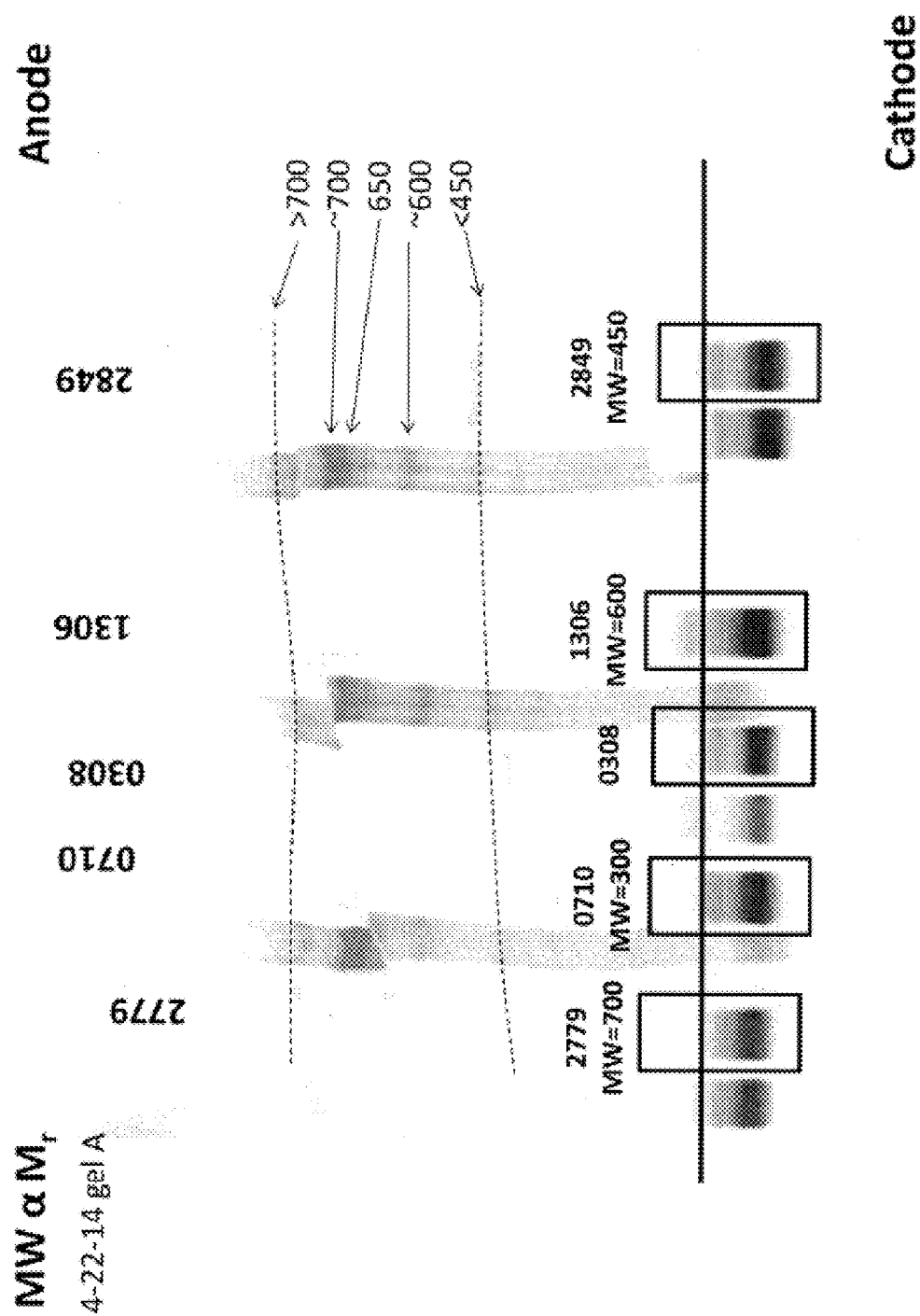
Figure 14V:
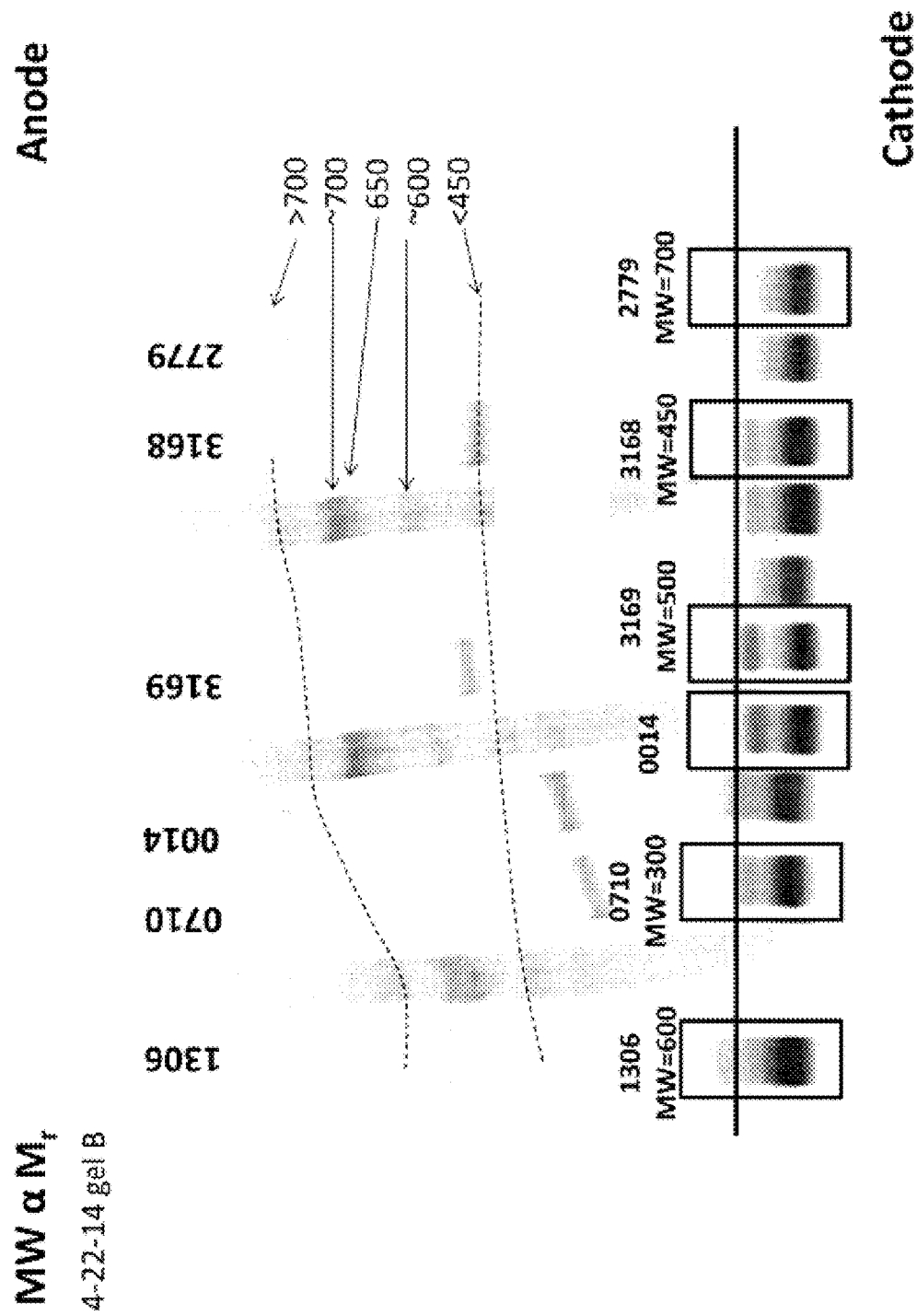

FIGS. 14A-14V present data comparing Lp(a) particle zonal migration velocities (inset, from FIGS. 11A-11C) associated with increasing MW of apo(a), measured by western blot. In FIGS. 14A-14V, more than 100 samples with Lp(a) zonal migration biases were compared to apo(a) isoform size analysis by western blot analysis, as described above. The results from the experiments reflecting the same setup and analysis as shown in FIG. 13 are presented. The results show consistent agreement of the zonal gel method for analyzing Lp(a) particle subform size with the more intensive analysis of separated apo(a) moieties from the same particles. "DBL" indicates the presence of two apo(a) isoforms in a lane.

DETAILED DESCRIPTION

The methods described herein significantly improve upon the existing lipoprotein detection methods available for quantifying particle numbers and population mass of Lp(a) particles. The disclosed methods also provide for the efficient and cost-effective measurement of specific Lp(a) particles in a rapid, low-cost format.

The terms "lipoprotein particle," "lipid protein particle," "lipid particle," and the like as used herein refers to a particle that contains both protein and lipid. Examples of lipoprotein particles are described in more detail below.

The term "lipoprotein particle number", "particle number", and the like as used herein refers to the molar concentration, nmol/L, of lipoprotein particles present in the bodily fluid.

The term "molecular weight" may refer to molar mass.

The term "particle size" may further refer to the detected average molecular mass of population. Given the atherogenic differences associated with large and small Lp(a), an algorithm could be established for CVD risk relative to Lp(a) particle number mitigated by subform size.

The term "apolipoprotein" as used herein refers to a protein that combines with lipids to form a lipoprotein particle. Examples of apolipoprotein types are described in more detail below. The unique nature of the apolipoprotein is their stoichiometric relationship to lipoprotein particles, providing an estimate of the lipoprotein particle number, which is described in more detail below.

As used herein, the term "antibody" is meant to include intact immunoglobulins derived from natural sources or from recombinant sources, as well as immunoreactive portions (i.e. antigen binding portions) of intact immunoglobulins. The antibodies of the invention may exist in a variety of forms including, for example, polyclonal antibodies, monoclonal antibodies, intracellular antibodies, antibody fragments (e.g. Fv, Fab and F(ab)2), as well as single chain antibodies (scFv), chimeric antibodies and humanized antibodies (Ed Harlow and David Lane, Using Antibodies: A Laboratory Manual (Cold Spring Harbor Laboratory Press, 1999); Houston et al., "Protein Engineering of Antibody Binding Sites: Recovery of Specific Activity in an Anti-Digoxin Single-Chain Fv Analogue Produced in *Escherichia coli*," Proc Natl Acad Sci USA 85:5879-5883 (1988); Bird et al, "Single-Chain Antigen-Binding Proteins," Science 242:423-426 (1988), which are hereby incorporated by reference in their entirety).

The term "Mab" refers to a monoclonal antibody, and the term "PAb" refers to a polyclonal antibody.

The term "reference range" and like terms refer to concentrations of components of biological samples known in the art to reflect typical normal observed ranges in a population of individuals.

A first aspect of the invention relates to a method for determining the concentration of a lipoprotein(a) subform in a biological sample. The method involves contacting a biological sample with a signal-producing moiety under conditions suitable for a signal-producing moiety to bind to a lipoprotein(a) subform in the biological sample to form a moiety-bound sample. The method also involves depositing a fraction of the moiety-bound sample in a capillary electrophoresis system; separating components of the fraction via capillary isotachophoresis; and detecting signals produced by the signal-producing moiety. The method further involves quantifying, based on said detecting, the concentration of the lipoprotein(a) subform in the sample, where the detected signals are proportional to the molar concentration of the lipoprotein(a) subform in the fraction.

As described above, an Lp(a) particle comprises a single apo(a) protein and a single apo(b) protein. Apo(a) may comprise a range of sizes due to the repeats of a particular sequence of amino acids in the protein, a region described as having kringle repeats (see Lackner et al., "Molecular Basis of Apolipoprotein(a) Subform Size Heterogeneity as Revealed by Pulsed-Field Gel Electrophoresis," J Clin Invest 87:2153-61 (1991); Lackner et al., "Molecular Definition of The Extreme Size Polymorphism in Apolipoprotein (a)," Hum Mol Genet 2:933-940 (1993), each of which is hereby incorporated by reference in their entirety).

The methods of the present invention can distinguish Lp(a) particles with apo(a) proteins of molecular weights, for example, greater than 700 kD, less than 600 kD, and between 600 and 700 kD. In one embodiment, the molar mass of an apo(a) protein of an individual Lp(a) subform is greater than 600 kD. In another embodiment, the molar mass of apo(a) protein of the individual Lp(a) subforms is determined to be greater than 700 kD. In an alternate embodiment, the molar mass of apo(a) protein of the individual Lp(a) subforms is between 600 and 700 kD. In a select embodiment, the molar mass of apo(a) protein of the individual Lp(a) subforms is less than 600 kD.

Determining the molar mass of the population of Lp(a) subforms according to aspects illustrated herein may involve assigning the Lp(a) subform size to one of a low, mid, or high molar mass category. For instance, the Lp(a) subform size having a molar mass less than about 600 kD may be assigned to the low molar mass category; individual Lp(a) subform size having a molar mass of between about 600 kD and 700 kD may be assigned to the mid molar mass category; and individual Lp(a) subform size having a molar mass of greater than about 700 kD are assigned to a high molar mass category.

Suitable biological samples or biosamples according to the invention include human biological matrices, plasma, serum, and human lipoprotein fractions. For example, the sample may be fresh blood or stored blood or blood fractions. The sample may be a blood sample expressly obtained for the assays of this invention or a blood sample obtained for another purpose which can be subsampled for use in accordance with the methods known in the art. For instance, the biological sample may be whole blood. Whole blood may be obtained from the subject using standard clinical procedures. The biological sample may also be plasma. Plasma may be obtained from whole blood samples by centrifugation of anti-coagulated blood. The biological sample may also be serum. The sample may be pretreated as necessary by dilution in an appropriate buffer solution, concentrated if desired, or fractionated by any number of methods including but not limited to ultracentrifugation, fractionation by fast performance liquid chromatography (FPLC), or precipitation. Any of a number of standard aqueous buffer solutions, employing one of a variety of buffers, such as phosphate, Tris, or the like, at physiological to alkaline pH can be used.

Additional exemplary biological samples include, without limitation, urine, plasma, blood components, synovial fluid, ascitic fluid, and human lipoprotein fractions. The lipid fraction may be substantially pure such that it comprises a single lipoprotein class or subclass. An exemplary lipoprotein fraction is an Lp(a) lipoprotein fraction. Alternatively, the lipid fraction may be unpurified and comprise one or more lipoprotein particle classes or subclasses.

According to this aspect of the invention, the biological sample is contacted with a signal-producing moiety. In one embodiment, the signal-producing moiety is an antibody or an antibody fragment.

Methods for monoclonal antibody production may be carried out using techniques well-known in the art (Monoclonal Antibodies-Production, Engineering and Clinical Applications (Mary A. Ritter and Heather M. Ladyman eds., 1995), which is hereby incorporated by reference in its entirety). In one embodiment, the signal-producing moiety is a kringle 4 type 2 ($KIV_2$) domain anti-apo(a) antibody or an antibody fragment thereof.

Procedures for raising polyclonal antibodies are also well known (Ed Harlow and David Lane, Using Antibodies: A Laboratory Manual (Cold Spring Harbor Laboratory Press, 1988), which is hereby incorporated by reference in its entirety). For example, polyclonal antibodies may be produced by injecting a suitable animal host, such as a rabbit, with the lipoprotein of interest and an adjuvant. Approximately 0.02 milliliters may be injected, with reinjection occurring every 21 days until peak antibody titer is achieved. Antibody titer may be tested by, for example, an ear bleed. Antibodies to Apo B-100 or other apolipoprotein may be produced in this manner. Alternatively, antibodies to Apo B-100 or other apolipoprotein may be purchased commercially.

The antibody fragment may comprise binding portions of such antibodies. Such binding portions include the monovalent Fab fragments, Fv fragments (e.g., single-chain antibody, scFv), single variable VH and VL domains, and the bivalent F(ab')2 fragments, Bis-scFv, diabodies, triabodies, minibodies, etc. These antibody fragments can be made by conventional procedures, such as proteolytic fragmentation procedures, as described in James Goding, Monoclonal Antibodies: Principles and Practice 98-118 (Academic Press, 1983) and Ed Harlow and David Lane, Antibodies: A Laboratory Manual (Cold Spring Harbor Laboratory, 1988), which are hereby incorporated by reference in their entirety, or other methods known in the art.

The signal-producing moiety may comprise a signal-producing component. Suitable signal producing components include molecules that are capable of producing or causing production of a detectable signal and are known to those of skill in the art.

Examples of signal producing molecules that are capable of producing or causing production of a detectable signal include, but are not limited to, various enzymes, prosthetic groups, fluorescent materials, luminescent materials, bioluminescent materials, radioactive materials, positron emitting metals, and nonradioactive paramagnetic metal ions. The signal producing molecules may be coupled or conjugated either directly to the antibody or indirectly, through an intermediate (such as, for example, a linker known in the art) using techniques known in the art. See, for example, U.S. Pat. No. 4,741,900 for metal ions which can be conjugated to antibodies for use as diagnostics according to the invention.

In one embodiment, the signal-producing moiety comprises a signal-producing component comprising a radiolabel, an enzyme, a luminophore, or a fluorophore. Examples of enzymes include, but are not limited to, horseradish peroxidase, alkaline phosphatase, beta-galactosidase, or acetylcholinesterase; prosthetic group complexes such as, but not limited to, streptavidin/biotin and avidin/biotin. In accordance with this embodiment, the signal-producing component is an enzyme and the enzyme is peroxidase, alkaline phosphatase, or β-galactosidase.

Many suitable fluorophores are known in the art (see, e.g., "The Handbook-A Guide to Fluorescent Probes and Labeling Technologies," Molecular Probes, Inc., Eugene, Oreg., (2004), which is hereby incorporated by reference in its entirety) and may be chosen from the group including, but not limited to, Alexa Fluor® 350, Alexa Fluor® 405, Alexa Fluor® 488, Alexa Fluor® 532, Alexa Fluor® 546, Alexa Fluor® 555, Alexa Fluor® 568, Alexa Fluor® 594, Alexa Fluor® 647, Alexa Fluor® 680, Alexa Fluor® 750, Cy®3, Cy®5, Fluorescein (FITC), Oregon Green®, Pacific Blue™, Pacific Green™, Pacific Orange™, Tetramethylrhodamine (TRITC), Texas Red®, and Texas Red®.

Additional examples of fluorescent materials include, but are not limited to, umbelliferone, fluorescein, fluorescein isothiocyanate, rhodamine, dichlorotriazinylamine fluorescein, dansyl chloride or phycoerythrin.

Examples of luminescent material include, but are not limited to, luminol.

Examples of bioluminescent materials include, but not limited to, luciferase, luciferin, and aequorin.

Examples of radioactive material include, but are not limited to, bismuth (213Bi), carbon (14C), chromium (51Cr), (153Gd, 159Gd)5 gallium (68Ga, 67Ga), germanium (68Ge), holmium (166Ho), indium (115In, 113In, 112In, 111In), iodine (131I, 125I, 123I, 121I), lanthanium (140La), lutetium (177Lu), manganese (54Mn), molybdenum (99Mo), palladium (103Pd), phosphorous (32P), praseodymium (142Pr), promethium (149Pm), rhenium (186Re, 188Re), rhodium (105Rh), ruthemium (97Ru), samarium (153Sm), scandium (47Sc), selenium (75Se), strontium (85Sr), sulfur (35S), technetium (99Tc), thallium (201Ti), tin (113Sn, 117Sn), tritium (3H), xenon (133Xe), ytterbium (169Yb, 175Yb), yttrium (90Y), zinc (65Zn). Further examples include positron emitting metals using various positron emission tomographies, and nonradioactive paramagnetic metal ions.

In one embodiment, the signals produced by the signal-producing moiety are detectable by radiometric, colorimetric, luminometric, of fluorometric means. Detection of an antibody-signal producing molecule complex in accordance with the invention may also be achieved by addition of a reagent capable of interacting with the signal producing molecule, where the signal producing molecule produces a detectable signal upon contact with the reagent. For example, light is emitted when luciferase acts on the appropriate luciferin substrate.

A secondary antibody that is coupled to a detectable signal or moiety, such as for example, an enzyme (e.g., luciferase), fluorophore, or chromophore may also be used.

As noted above, each detectable signal of the at least two lipoprotein-binding complexes is distinguishable from the other detectable signal. This permits cocktailing at least two lipoprotein-binding complexes where each of the complexes detects a different epitope of the Lp(a) particle, each complex also producing or capable of producing a different detectable signal.

In one embodiment, the antibody cocktail comprise a first signal-producing moiety targeting a first lipoprotein(a) epitope and a second signal-producing moiety targeting a second lipoprotein(a) epitope, where the signals produced by the first signal-producing moiety are distinguishable from the signals produced by the second signal-producing moiety. Likewise, when the antibody cocktail comprises three, four, five, six, seven, eight, or nine different antibodies directed to different lipoprotein(a) epitopes, the signals produced by the signal-producing moiety of each different antibody are distinguishable from each other.

In accordance with this embodiment, a biological sample is contacted with an antibody cocktail, where the antibody cocktail comprises a first fluorophore-labeled antibody targeting a first lipoprotein(a) epitope and a second fluorophore-labeled antibody targeting a second lipoprotein(a) epitope. Accordingly, the fluorescent emission spectrum of the first fluorophore-labeled antibody does not significantly overlap with the fluorescent emission spectrum of the second fluorophore-labeled antibody. Likewise, when a fluorophore-labeled antibody cocktail comprises three, four, five, six, seven, eight, or nine fluorophore-labeled antibodies directed to different lipoprotein(a) epitopes, the fluorescent emission spectra of each fluorophore-labeled antibody do not significantly overlap with each other. Antibody cocktails and fluorescent detection are described in more detail in U.S. Patent Application Publication No. 201/0243431, which is hereby incorporated by reference in its entirety.

In an example, a first lipoprotein-binding complex may include fluorescein isothiocyanate (FITC)-labeled antibody which binds a kringle IV repeats on the apo(a) for all Lp(a) components in a sample. A second non-kringle IV-binding complex may include rhodamine-labeled antibody which binds a second portion of apo(a). The first and second complexes may be mixed or cocktailed together. This permits probing of multiple antigenic portions of apolipoproteins in an ELISA assay. The ratios of intensities from the kringle IV repeats to non-kringle IV components of apo(a) will facilitate a more accurate measurement of Lp(a) subform size, when compared to a known kringle IV/non-kringle IV standard.

The methods of the present invention may be used with any suitable capillary electrophoresis instrument and/or system. As described herein, capillary isotachophoresis separates analytes into bands or regions within a sample plug. In this mode of separation each analyte moves at the same speed, unlike in more convention Capillary Gel Electrophoresis (CGE) and Capillary Zone Electrophoresis (CZE) where each analyte travels through the capillary with its own unique constant velocity under the influence of the applied electric field.

In accordance with this aspect of the invention, a fraction of the moiety-bound sample is deposited in a capillary electrophoresis instrument. In one embodiment, the fraction is separated along a common capillary of a capillary isotachophoresis system such that the components of the fraction are separated from one another along the common capillary.

In another embodiment, the capillary isotachophoresis system is a multiplex capillary isotachophoresis (MPCE-ITP) system. Such systems allow the simultaneous evaluation of multiple samples and include a parallel array of capillaries for high-throughput applications.

In some embodiments, the system may include a light source with a broad optical bandwidth such as a light bulb or a laser; optical filters to select the light of the desired wavelength to excite a fluorophore; optical filters to filter the light emitted from the excited fluorophore; optical lenses to focus the emitted signal, and a detector to detect the signal produced from the signal-producing moiety. In this manner, only light of the desired wavelength is detected.

The system and methods may also include a detector for detecting the signal produced by a signal-producing moiety, where the detecting indicates the level of the specific Lp(a) particles or particle components in the biological sample. Exemplary detectors include a photomultiplier tube, a photoconductive cell, a semiconductor optical detector, or a photodiode array.

The system may also comprise a processor to process the detected signal. An exemplary detector is a deltaDOT's multipixel detector, which allows the tracking of a signal peak as it moves across a capillary viewing region.

The processor may also comprise a software algorithm to calculate concentrations of a labeled-lipoprotein(a) subform relative to concentrations of a labeled-lipoprotein(a) calibrator lipoprotein(a) subform. Likewise, the processor may calculate both Lp(a) particle and apo(a) subform size. Exemplary programs in the art include optical density calculation programs.

In an example, the processor is programmed with signal processing algorithms to process the signal by (i) reading the signal in a time dependent manner from a detector; (ii) interpreting the read signal with algorithms to filter noise, compute a single intensity value from the input signal, (iii) performing a quality assessment of the computed values; and (iv) producing an output value for further analysis. Signal processing may be accomplished using various technologies known in the art. The further analysis may comprise human interpretation or additional computational processing.

The presence of the detected particle or a portion thereof in reaction vessel may then be quantified by measurement of the detectable signal or moiety. The particle number may then be calculated according to known stoichiometric relationships such as the known 1:1 stoichiometry of apo(b) to Lp(a) or apo(a) to Lp(a).

In many cases, the output is an electropherogram showing the detected signals as peaks for identification and analysis. As described herein, an electropherogram is a plot of results recording the separated components of a biological sample produced by capillary electrophoresis (see FIG. 5 and Examples 2-5). The electropherogram may comprise several peaks, each corresponding to the relative molar concentration and/or particle number of a signal-producing moiety labeled sample component (see Examples 2-5).

Some dimension or representation of a signal's peak may be proportional to the molar concentration of a detected sample component. The particle number of a particular Lp(a) subform may be quantified by comparison with a separate analysis that characterizes the total Lp(a) particle concentration in the sample. Such separate analysis may be ultracentrifugation, NMR, electrophoresis, or any other analysis method that can characterize a concentration or total particle number for particles in the sample.

The system may further comprise a storage module for the output value thus obtained. Further, the system comprises a module for generating a report based on output value for the user.

A second aspect of the invention relates to a method for determining the particle number of a lipoprotein(a) subform in a biological sample. The method involves contacting a biological sample with a signal-producing moiety under conditions suitable for a signal-producing moiety to bind to lipoprotein(a) subforms in the biological sample to form a moiety-bound sample. The method also involves depositing a fraction of the moiety-bound sample in a capillary electrophoresis system; separating components of the fraction via capillary isotachophoresis; and detecting signals produced by the signal-producing moiety. The method further involves quantifying, based on said detecting, the particle number of the lipoprotein(a) subform in the sample, where the detected signals are proportional to the particle number of the lipoprotein(a) subform in the fraction.

The contacting, depositing, separating, detecting, and quantifying steps of this aspect of the invention may be performed according to any of the preceding embodiments of the first aspect of the invention.

Suitable biological samples are described in detail above. In accordance with this aspect of the invention, biological samples are contacted with a signal-producing moiety.

In one embodiment, the signal-producing moiety comprises a signal-producing component comprising a radiolabel, an enzyme, a luminophore or a fluorophore. Exemplary signal-producing moieties are described in detail above. In accordance with this embodiment, the enzyme is peroxidase, alkaline phosphatase or β-galactosidase.

The signals produced by the signal-producing moiety are detectable by radiometric, colorimetric, luminometric, or fluorometric means.

In one embodiment, the fraction is separated along a common capillary of a capillary isotachophoresis system such that the components of the fraction are separated from one another along the common capillary.

In another embodiment, the capillary isotachophoresis system is a multiplex capillary isotachophoresis (MPCE-ITP) system. Such systems allow the simultaneous evaluation of multiple samples and include a parallel array of capillaries for high-throughput applications.

The system may comprise a laser induced fluorescence (LIF) system. LIF systems are known in the art. In one embodiment, the capillary isotachophoresis system is a multiplex capillary isotachophoresis laser induced fluorescence (MPCE-ITP-LIF) system.

In a standard use of the system, the particles are separated on the CE-ITP system with high resolution such that Lp(a) subforms are separated from each other by their size. Lp(a) subforms are distinguished by the number of apo(a) kringle IV type 2 repeats in the attached apo(a) molecule. Increases and decreases of the numbers of type 2 repeats affects the electrophoretic mobility by a multiple of a single type 2 subunit. The minor changes can be identified with an instrument possessing high resolution separation and detection abilities such as an MPCE-ITP-LIF system. Lipoproteins in the sample incubated with a non-specific dye such as carboxyfluorescein or NDB-ceramide dye-anchor system are detectable by the optical system. ITP separation according to the methods described herein facilitate separation of the Lp(a) subforms.

A standard/calibrator with known Lp(a)-P and subform size may be included as reference for all unknown samples for which Lp(a)-P and apo(a) subform analysis is to be performed. The calibrator has a known concentration and apo(a) size.

In one embodiment, standards for Lp(a) subform types may be run containing known masses of Lp(a). The positions of separated Lp(a) subforms are recorded to identify expected positions of Lp(a) subforms separated from unknowns.

In some embodiments, the signal-producing moiety comprises an antibody, an antibody fragment, and/or a non-specific lipid dye. As described above, the antibodies may be monoclonal or polyclonal. Moreover, antibody fragments encompass binding portions of such antibodies. Such binding portions include the monovalent Fab fragments, Fv fragments (e.g., single-chain antibody, scFv), single variable VH and VL domains, and the bivalent F(ab')2 fragments, Bis-scFv, diabodies, triabodies, and minibodies.

The non-specific dye may be a lipophilic dye. Exemplary lipophilic dyes may include fluorescently-tagged lipid anchors like fluorescently-labeled fatty acid analogs. Such optically-active components may be broadly termed lipophilic dyes, with or without the lipid anchor. An example of labeled fatty acid analog is NDB-ceramide. The NDB moiety is a useful label in the hydrophobic environment of a lipid membrane, as it has drastically different optical properties than its properties in an aqueous environment outside the lipid particle and lipid membrane. Other possible fluorescent label-linked fatty acids include ADIFAB fatty acid indicators, phospholipids with BODIPY dye-labeled acyl chains such as BODIPY glycerophospholipids, phospholipid with DPH-labeled acyl chain, phospholipids with NBD-labeled acyl chains, phospholipids with pyrene-labeled acyl chains, phospholipids with a fluorescent or biotinylated head group, LipidTOX phospholipid and neutral lipid stains. Many such options are provided by Life Technologies™ for research and production laboratory assays.

A variety of lipophilic dyes may be used with or without a lipid anchor may be used such as carboxyfluorescein, BODIPY dyes, or the Alexa Fluor™ series. Such dyes are known by those skilled in the art and may be chosen from a group including, but not limited to lipophilic versions of fluorescent dyes including Alexa Fluor® 350, Alexa Fluor® 405, Alexa Fluor® 488, Alexa Fluor® 532, Alexa Fluor® 546, Alexa Fluor® 555, Alexa Fluor® 568, Alexa Fluor® 594, Alexa Fluor® 647, Alexa Fluor® 680, Alexa Fluor® 750, BODIPY® FL, Coumarin, Cy®3, Cy®5, Fluorescein (FITC), Oregon Green®, Pacific Blue™, Pacific Green™, Pacific Orange™, Tetramethylrhodamine (TRITC), Texas Red®, DNA stains, DAPI, Propidium Iodide, SYTO® 9, SYTOX® Green, TO-PRO®-3, Qdot® probes, Qdot® 525, Qdot® 565, Qdot® 605, Qdot® 655, Qdot® 705, Qdot® 800, other lipophilic fluorescein derivatives such as carboxyfluorescein, carbocyanine derivatives such as iD (DiIC18[5]), DiI (or DiIC18[3]), DiI in vegetable oil, Dilinoleyl DiI, Dilinoleyl DiO, DiO (or DiOC18[3]), DiOC14 (3), hydroxyethanesulfonate, DiOC16(3), DiR (DiIC18[7]), DiSC2(5), DODC (DiOC2(5)), Neuro-DiI, Neuro-DiI in vegetable oil, Neuro-DiO, Neuro-DiO in vegetable oil.

When using a lipid anchor, a variety of options may be chosen from the group including, but not limited to fatty acids, phospholipids, acyl chains such as glycerophospholipids, and neutral lipids.

Incubation with the lipophilic dyes and unknown lipid particles is done to saturation of the lipid membrane. In addition to time, mixing and heating and cooling steps may facilitate rapid saturation of the label in the membrane.

The saturation ratios of lipophilic dyes to particle phospholipid composition are consistent from particle to particle when carried to saturation. In an example, NDB-ceramide to phospholipid fraction is the same in HDL, LDL, VLDL, IDL, and Lp(a) particles in an unknown sample.

When an antibody or antibody fragment and a non-specific dye are used, the emission spectra of the antibody or antibody fragment and non-specific dye are distinguishable and do not significantly overlap. In accordance with this embodiment, the intensity of the signals detected correspond to the amount of lipoprotein(a) particles in the sample.

In some embodiments, samples are contacted with an antibody cocktail, where at least two labeled antibodies are mixed with a sample prior to loading on the MPCE-ITP-LIF instrument targeting distinct antigenic components of the sample. In accordance with this embodiment, a first antibody may target the apo(b) apolipoprotein found on LDL, VLDL, and Lp(a) particles and a second antibody may target apo(a) apolipoproteins found on Lp(a) particles. Likewise, the emission spectra of the first and second antibodies are distinguishable and do not significantly overlap. Antibody cocktails and fluorescent detection are described further in US Patent Application Publication No. 20140243431, incorporated herein by reference.

In each of the preceding embodiments, the biological sample may be contacted with an first signal-producing moiety comprising an antibody or antibody fragment directed to an apo(a) kringle IV type 2 subunit and a second signal-producing moiety comprising an antibody or antibody fragment directed to an apo(b) protein or a non-subunit specific apo(a) antibody. For example, the biological sample may be contacted with an apo(a) kringle IV type 2 subunit antibody and an apo(b) specific antibody. Alternatively, the biological sample may be contacted with an apo(a) kringle IV type 2 subunit antibody and a non-subunit specific apo(a) antibody.

Alternatively, the biological sample may be contacted with an first signal-producing moiety comprising an antibody or antibody fragment directed to an apo(a) kringle IV type 2 subunit and a non-specific lipophilic dye to facilitate accurate calculation of Lp(a) concentrations by techniques known in the art.

In each of the preceding embodiments, the individually measured fluorescence signals may be compared to fluorescence signals produced by the signal-producing calibrator Lp(a) particle, normalized to the calibrator Lp(a) particle molar concentration, and mathematically translated to both Lp(a) Particle Number (PN) and apo(a) subform size.

For example, when the molecular weights of the calibrator and unknown Lp(a) subforms are equal, the concentration of an unknown Lp(a) particle (Lp(a)–P) can be determined based on the following formula:

$$[\text{Unknown } Lp(a) - P] = [\text{Calibrator } Lp(a) - P] \times \frac{\text{Unknown Signal Intensity}}{\text{Calibrator Signal Intensity}},$$

where [Unknown Lp(a)–P] is equivalent to the unknown lipoprotein(a) particle concentration and [Calibrator Lp(a)–P] is equivalent to the calibrator lipoprotein(a) particle concentration.

When the relationship between the number of $KIV_2$ repeats in an apo(a) protein of a particular Lp(a) subform is known, the total molar amount of a $KIV_2$ can be determined using the following formula:

$$\text{total mols } KIV2 = \frac{X \text{ mol } KIV2}{\text{mol } apo(a)} \times \text{total mol } apo(a)$$

Similarly, when the relationship between the number of $KIV_2$ repeats in an apo(a) protein of a calibrator Lp(a) subform is known, the total molar amount of a $KIV_2$ can be determined using the following formula:

$$\text{total mols calibrator } KIV2 = \frac{X \text{ mol calibrator } KIV2}{\text{mol calibrator } apo(a)} \times \text{total mol calibrator } apo(a)$$

As described in more detail herein, the molecular weight of an unknown or target apo(a) protein can be determined using the following formula:

$$\text{MW of unknown } apo(a) = \left(\frac{F^{unknown}}{F^{calibrator}}\right)\left(\frac{\text{total mol calibrator } KIV2}{\text{mol } apo(a) \text{ in unknown from } Mab''}\right)(\text{MW of } KIV2) + \text{MW of non-}KIV2 \, apo(a)$$

where: $F^{unknown}$ is equivalent to the detected fluorescence of an unknown Lp(a) sample contacted with a monoclonal antibody directed to KIV type 2 repeats; $F^{calibrator}$ is equivalent to the detected fluorescence of a calibrator Lp(a) sample contacted with monoclonal antibody directed to KIV type 2 repeats; mol apo(a) in unknown from Mab" indicates that an unknown sample was contacted with a non-kringle subunit specific apo(a) antibody; MW of $KIV_2$ indicates the molecular weight of a single KIV type 2 subunit in g/mol; and MW of non-$KIV_2$ apo(a) indicates the molecular weight of apo(a) not due to KIV type 2 subunit repeats in grams/mol.

In accordance with any of the preceding embodiments, the fraction of the moiety-bound sample further comprises a known concentration of a signal-producing calibrator lipoprotein(a) subform comprising a known molar mass and/or a known number of kringle $KIV_2$ domains and/or a known concentration of apolipoprotein A (apo(a)) and/or a known concentration of apolipoprotein B (apo(b)).

In accordance with this embodiment of the invention, the signal produced by the signal-producing calibrator lipoprotein(a) is measured and compared with the signal produced from the signal-producing moiety and the molar mass of the lipoprotein(a) subform is determined based on the following formula:

$$[LP(a) - P] = [Cal \, LP(a) - P] \times \frac{(LP(a) - P \text{ signal})}{(Cal \, LP(a) - P \text{ signal})},$$

where: [LP(a)–P] is the molar mass of the target lipoprotein(a) subform, [Cal LP(a)–P] is the molar mass of the calibrator lipoprotein(a) subform, (LP(a)–P signal) is the signal intensity of the lipoprotein(a) subform (LP(a)–P), and (Cal LP(a)–P signal) is the signal intensity of the calibrator lipoprotein(a) subform (Cal LP(a)–P).

In one embodiment, the concentration of the Lp(a) and the Cal(a) particles are equal or normalized based on the known concentration of both. As known to one skilled in the art, the concentration of the target can be determined through the use of an apo(b) antibody or a non-kringle apo(a) antibody because each Lp(a) particle has a single apo(a) and a single apo(b) protein.

In another embodiment, the particle number of the lipoprotein(a) subform is determined as molar concentration in nmol/L, wherein the particle number of the lipoprotein(a) subform is quantified based on apo(b) concentration of the lipoprotein(a) subform.

Results from the methods of the present invention include Lp(a) particle number, Lp(a) subform population size, Lp(a) subform mass, and Lp(a) population subform mass distribution.

A third aspect of the invention relates to a method of assessing cardiovascular risk in a subject. The method comprises (i) determining particle number and/or molar mass of a lipoprotein(a) subform in a biological sample from a subject and (ii) assessing the cardiovascular risk of the subject based on the particle number and/or molar mass of the lipoprotein(a) subform. Determining the particle number and/or molar mass of the lipoprotein(a) subform involves (a) contacting the biological sample with a signal-producing moiety under conditions suitable for the signal-producing moiety to bind to the lipoprotein(a) subform to form a moiety-bound sample; (b) depositing a fraction of the moiety-bound sample in a capillary electrophoresis system; (c) separating components of the fraction via capillary isotachophoresis; (d) detecting signals produced by the signal-producing moiety; and (e) quantifying, based on said detecting, the particle number and/or molar mass of the lipoprotein(a) subform in the sample, where the detected signals are proportional to the particle number of the lipoprotein(a) subform in the fraction.

The contacting, depositing, separating, detecting, and quantifying steps of this aspect of the invention may be performed according to any of the preceding embodiments of the invention.

It is well-established that the lipoprotein subclass distribution profile of an individual may be indicative of a health risk. In particular, cardiovascular and metabolic disorders are correlated strongly with specific patterns of subclass quantity and size (see U.S. Pat. No. 6,518,069).

Various disease states, including but not limited to cardiovascular disease, liver disease, and diabetes mellitus, are associated with the levels of apolipoproteins and/or lipoprotein particles (see, e.g., U.S. Pat. No. 6,518,064). For example, increased levels of Lp(a), which comprise an LDL-like particle with apo(a) bound to apo(b) by a disulfide bond, is associated with an increased risk of early atherosclerosis independent of other cardiac risk factors. Thus, the risk of developing a cardiovascular disease can be assessed by quantifying the levels of Lp(a) lipoproteins.

As noted above, apo(a) is one such protein that partly comprises the Lp(a) particle. Apo(a) may comprise a range of sizes due to the repeats of a particular sequence of amino acids in the protein, a region described as having kringle repeats. The number of kringle repeats in apo(a) may range from under 10 to greater than 50 repeats. The various sizes of apo(a) due to kringle repeats are called apo(a) subforms. Lp(a) is known to be a risk factor for cardiovascular disease and an increase in the number of kringle repeats is inversely correlated with Lp(a) concentration. Correspondingly, the size of Lp(a) particles in the blood may have significant importance for cardiovascular health. See Rifai et al., "Apolipoprotein(a) Size and Lipoprotein(a) Concentration and Future Risk of Angina Pectoris with Evidence of Severe Coronary Atherosclerosis in Men: The Physicians' Health Study," Clinical Chem. 58(8):1364-1371 (2004); Erqou et al., "Apolipoprotein(a) Isoforms and the Risk of Vascular Disease," J. Am. Coll. Cardiology 55(19): 2160-7 (2010); and Thomas Dayspring "Lipoprotein(a)," available at lipidcenter.com/pdf/Entire_Lpa_Complexities (2010), each of which is hereby incorporated by reference in its entirety. Accordingly, determining cardiovascular risk according to aspects described herein may involve assigning the subject to one of a low, moderate, or high cardiovascular risk category.

There are well established recommendations for cut-off values for biochemical markers for determining risk (see Rifai et al., "Apolipoprotein(a) Size and Lipoprotein(a) Concentration and Future Risk of Angina Pectoris with Evidence of Severe Coronary Atherosclerosis in Men: The Physicians' Health Study," Clinical Chem. 58(8):1364-1371 (2004); Erqou et al., "Apolipoprotein(a) Isoforms and the Risk of Vascular Disease," J. Am. Coll. Cardiology 55(19): 2160-7 (2010); and Thomas Dayspring "Lipoprotein(a)," available at lipidcenter.com/pdf/Entire_Lpa_Complexities (2010); Braunwald's Heart Disease: A Textbook of Cardiovascular Medicine 9th ed. (Bonow et al. eds. 2011); "Executive Summary of The Third Report of The National Cholesterol Education Program (NCEP) Expert Panel on Detection, Evaluation, And Treatment of High Blood Cholesterol In Adults (Adult Treatment Panel III)," JAMA 285:2486-2497 (2001); "Adult Treatment Panel III (ATP III) of the National Cholesterol Education Program. Implications of Recent Clinical Trials for the National Cholesterol Education Program Adult Treatment Panel III Guidelines," Circulation 110(2):227-39 (2004); and MedlinePlus, A service of the U.S. National Library of Medicine and National Institutes of Health available at nlm.nih.gov/medlineplus, each of which is hereby incorporated by reference in its entirety.)

As described above, suitable biological samples or biosamples according to the invention include human biological matrices, plasma, serum, and human lipoprotein fractions.

Suitable subjects may be selected from the group including, but not limited to, a human, a non-human primate, a rodent, a canine, a feline, and a bovied.

In one embodiment, the subject is a human.

The subject may be healthy. Alternatively, the subject may be known to suffer from a cardiovascular or metabolic disorder and/or at risk of suffering from a cardiovascular or metabolic disorder. The subject may be a patient suspected of suffering from a lipoprotein-associated disorder including, but not limited to, cardiovascular disorders and obesity. Additional lipoprotein disorders include hyperlipidemia (i.e., the abnormal elevation of lipids or lipoproteins in the blood), arteriovascular disease, atherosclerosis, pancreatitis, and liver disorders. Elevated or unbalanced lipid and lipoprotein levels are reflective of a subject's development of or progression of diabetic conditions and metabolic disorders.

As described above, suitable biological samples according to the invention include, without limitation, fresh blood, stored blood, or blood fractions.

In one embodiment, the fraction is separated along a common capillary of a capillary isotachophoresis system such that components of the fraction are separated from one another along the common capillary.

In another embodiment, the capillary isotachophoresis system is a multiplex capillary isotachophoresis (MPCE-ITP) system. Such systems allow the simultaneous evaluation of multiple samples and include a parallel array of capillaries for high-throughput applications.

The system may comprise a laser induced fluorescence (LIF) system. LIF systems are known in the art. In one embodiment, the capillary isotachophoresis system is a multiplex capillary isotachophoresis laser induced fluorescence (MPCE-ITP-LIF) system.

As described above, the isotachophoresis system may include a device or use of a device for detecting the detectable signal. The system may also comprise a processor connected to the detector to process the detected signal into an output value for interpretation by another processor or a human. The system may further comprise a storage module for the output value thus obtained. Further, the system comprises a module for generating a report based on the output value for the user.

In another embodiment, the loading fraction further comprises a known concentration of a signal-producing calibrator lipoprotein(a) comprising a known molar mass and/or a known number of kringle $KIV_2$ domains and/or a known concentration of apolipoprotein A (apo(a)) and/or a known concentration of apolipoprotein B (apo(b)). In accordance with this embodiment, the method further comprises quantifying, based on said detecting, concentration of apo(b) in the lipoprotein(a) subform. In accordance with this embodiment of the invention, the particle number of the lipoprotein (a) subform is determined based on the concentration of apo(b) in the lipoprotein(a) subform.

In another embodiment, the signal produced by the signal-producing calibrator lipoprotein(a) is measured and compared with the signal produced from the signal-producing moiety and the molar mass of the lipoprotein(a) subform is determined based on the following formula:

$$[LP(a)-P] = [Cal\ LP(a)-P] \times \frac{(LP(a)-P\ \text{signal})}{(Cal\ LP(a)-P\ \text{signal})}$$

wherein: [LP(a)–P] is the molar mass of the target lipoprotein(a) subform, [Cal LP(a)–P] is the molar mass of the calibrator lipoprotein(a) subform, (LP(a)–P signal) is the signal intensity of the lipoprotein(a) subform (LP(a)–P), and (Cal LP(a)–P signal) is the signal intensity of the calibrator lipoprotein(a) subform (Cal LP(a)–P).

In one embodiment, the concentration of the Lp(a) and the Cal(a) particles are equal or normalized based on the known concentration of both. As known to one skilled in the art, the concentration of the target can be determined through the use of an apo(b) antibody or a non-kringle apo(a) antibody because each Lp(a) particle has a single apo(a) and a single apo(b) protein.

In accordance with this embodiment, the lipoprotein(a) subform having a molar mass less than about 600 kD are assigned to the low molar mass category, the lipoprotein(a) subform having a molar mass of between about 600 kD and 700 kD are assigned to the mid molar mass category, and the lipoprotein(a) subform having a molar mass of greater than about 700 kD are assigned to a high molar mass category.

In another embodiment, the therapeutic regimen for the subject is selected, or an existing therapeutic regimen for the subject is modified or changed based on the particle number and/or molar mass of the lipoprotein(a) subform.

In some embodiments, the subject is assigned to one of a low, moderate, or high cardiovascular risk categories based on the particle number and/or molar mass of the lipoprotein (a) subform.

In one embodiment, the selected therapeutic regimen comprises administering a drug and/or a supplement or the existing therapeutic regimen comprises administering a modified dose of a drug and/or a supplement. In accordance with this embodiment of the invention, the drug is selected from the group consisting of niacin, an anti-inflammatory agent, an antithrombotic agent, an anti-platelet agent, a fibrinolytic agent, a lipid reducing agent, a direct thrombin inhibitor, a glycoprotein IIb/IIIa receptor inhibitor, an agent that binds to cellular adhesion molecules and inhibits the ability of white blood cells to attach to such molecules, a calcium channel blocker, a beta-adrenergic receptor blocker, an angiotensin system inhibitor, and combinations thereof.

In another embodiment, the drug is selected from the group consisting of niacin, fenofibrate, estrogen, raloxifene and any combinations thereof.

In other embodiments, the drug is selected from the group consisting of niacin, statin, ezetimibe and any combinations thereof.

In some embodiments, the selected therapeutic regimen involves giving recommendations on making or maintaining lifestyle choices based on the results of said cardiovascular risk determination. In accordance with this embodiment of the invention, the lifestyle choices involve changes in diet, changes in exercise, reducing or eliminating smoking, or a combination thereof.

In any of the preceding embodiment, the biological sample is selected from the group consisting of blood, plasma, urine and saliva.

As described above, the isotachophoresis system may include a module for generating a report based on the output value for the user. A report may also be generated that includes, among other things, a description of the selected treatment regimen. In some embodiments, the results of lipoprotein analyses are reported in such a report. A report refers in the context of lipoprotein and other lipid analyses to a report provided, for example to a patient, a clinician, other health care provider, epidemiologist, and the like, which includes the results of analysis of a biological specimen, for example a plasma specimen, from an individual. Reports can be presented in printed or electronic form, or in any form convenient for analysis, review and/or archiving of the data therein, as known in the art.

A report may include identifying information about the individual subject of the report, including without limitation name, address, gender, identification information (e.g., social security number, insurance numbers), and the like. A report may include biochemical characterization of the lipids in the sample in addition to Lp(a), for example without limitation triglycerides, total cholesterol, LDL cholesterol, and/or HDL cholesterol, and the like. A report may further include characterization of lipoproteins, and reference ranges therefore, conducted on samples prepared by the methods provided herein.

Exemplary characterization of lipoproteins in an analysis report may include the concentration and reference range for VLDL, IDL, Lp(a), LDL and HDL, and subclasses thereof. A report may further include lipoprotein size distribution trends.

EXAMPLES

The following examples are provided to illustrate embodiments of the present invention but they are by no means intended to limit its scope.

Example 1—Optical Apparatus for Use in CE-ITP-LIF Systems

Figure 1:
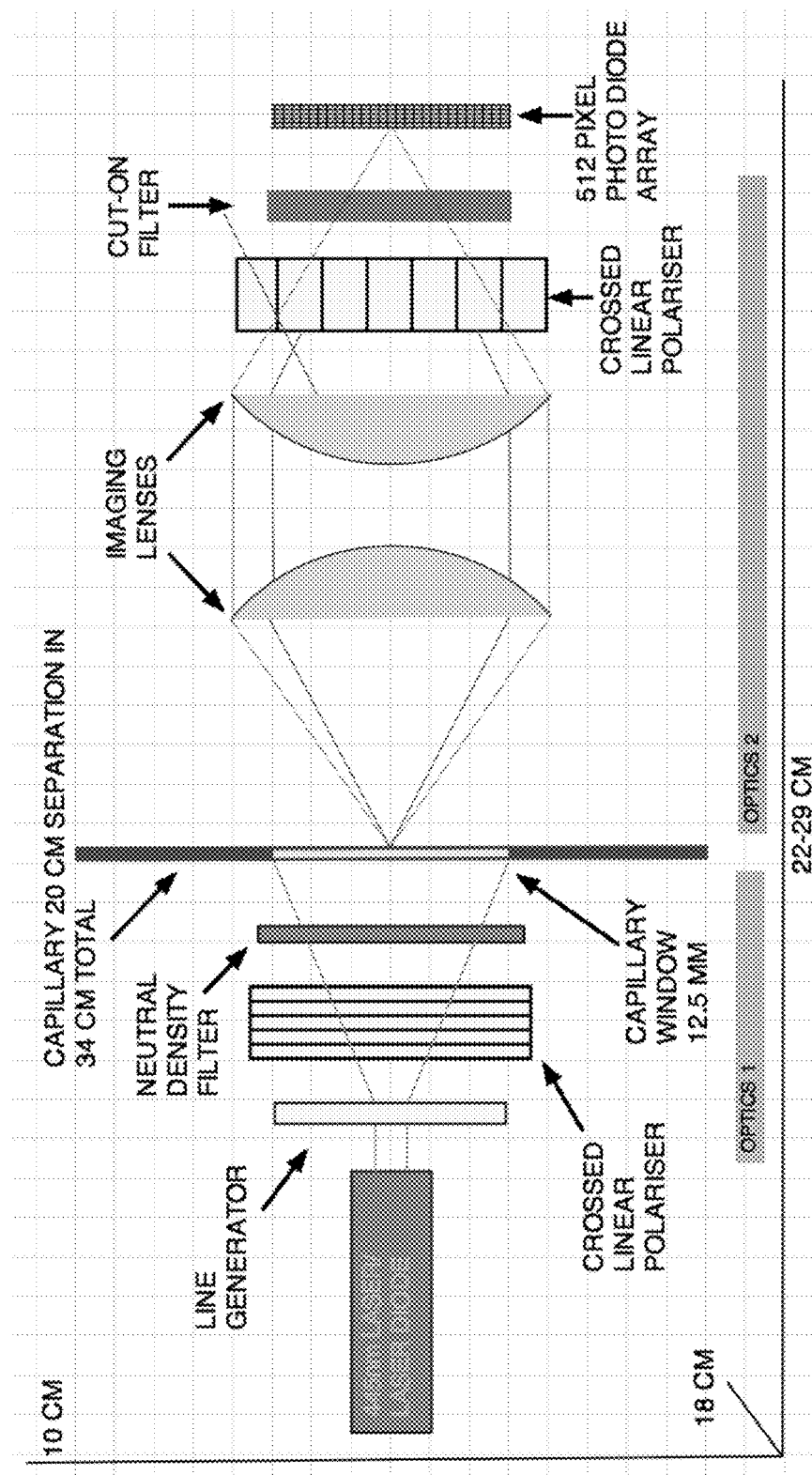
FIG. 1 is a schematic drawing of a system comprising two optics zones. Optics zone 1 comprises an optical rail on which are arranged a 445 nm or other specific wavelength laser or laser diode. Light form these sources is focused through a series of optical components comprising, but not limited to, a line generator, a crossed linear polarizer, and a neutral density filter. Light from Optics zone 1 is focused onto a 12.5 mm area of a 100 µM internal diameter fused silica capillary (~365 µM o.d.) in which a 20 mm viewing window has been created by the thermal removal of the polyamide sheath. The light then passes through the sample that is being separated by ITP and excites the fluorescent label attached to each analyte molecule. Emitted light energy, at a wavelength specific to the fluorescent label is then focused to a 512 pixel photo diode array ("PDA") through another series of optical component called Optics zone 2. Optics zone 2 comprises a set of imaging lenses (e.g., convex lenses), and an orthogonal crossed linear polarizer. After passing through a cut-on filter that transmits above a certain wavelength, the light energy reaches the detector where the data is acquired on the PDA and the signal is processed by proprietary signal processing algorithms.

A schematic of an optical apparatus comprising two optical zones for use in a CE-ITP-LIF system is shown in FIG. 1. Optics zone 1 comprises an optical rail on which are arranged a 445 nm or other specific wavelength laser or laser diode. Light from these sources is focused through a series of optical components comprising, but not limited to, a line generator, a crossed linear polarizer, and a neutral density filter. Light from optics zone 1 is focused onto a 12.5 mm area of a 100 μM internal diameter fused silica capillary (~365 μM o.d.) in which a 20 mm viewing window has been created by thermal removal of the polyamide sheath. The light then passes through the sample that is being separated by ITP and excites the fluorescent label attached to each analyte molecule (e.g., a lipoprotein and/or lipid particle). Emitted light energy, at a wavelength specific to the fluorescent label is then focused onto a 512 pixel photo diode array ("PDA") through another series of optical components in optics zone 2. Optics zone 2 comprises a set of imaging lenses (e.g., convex lenses), and an orthogonal crossed linear polarizer. After passing through a cut-on filter that transmits above a certain wavelength, the light energy reaches the detector where the data is acquired on the PDA and the signal is processed by signal processing algorithms.

Figure 2:
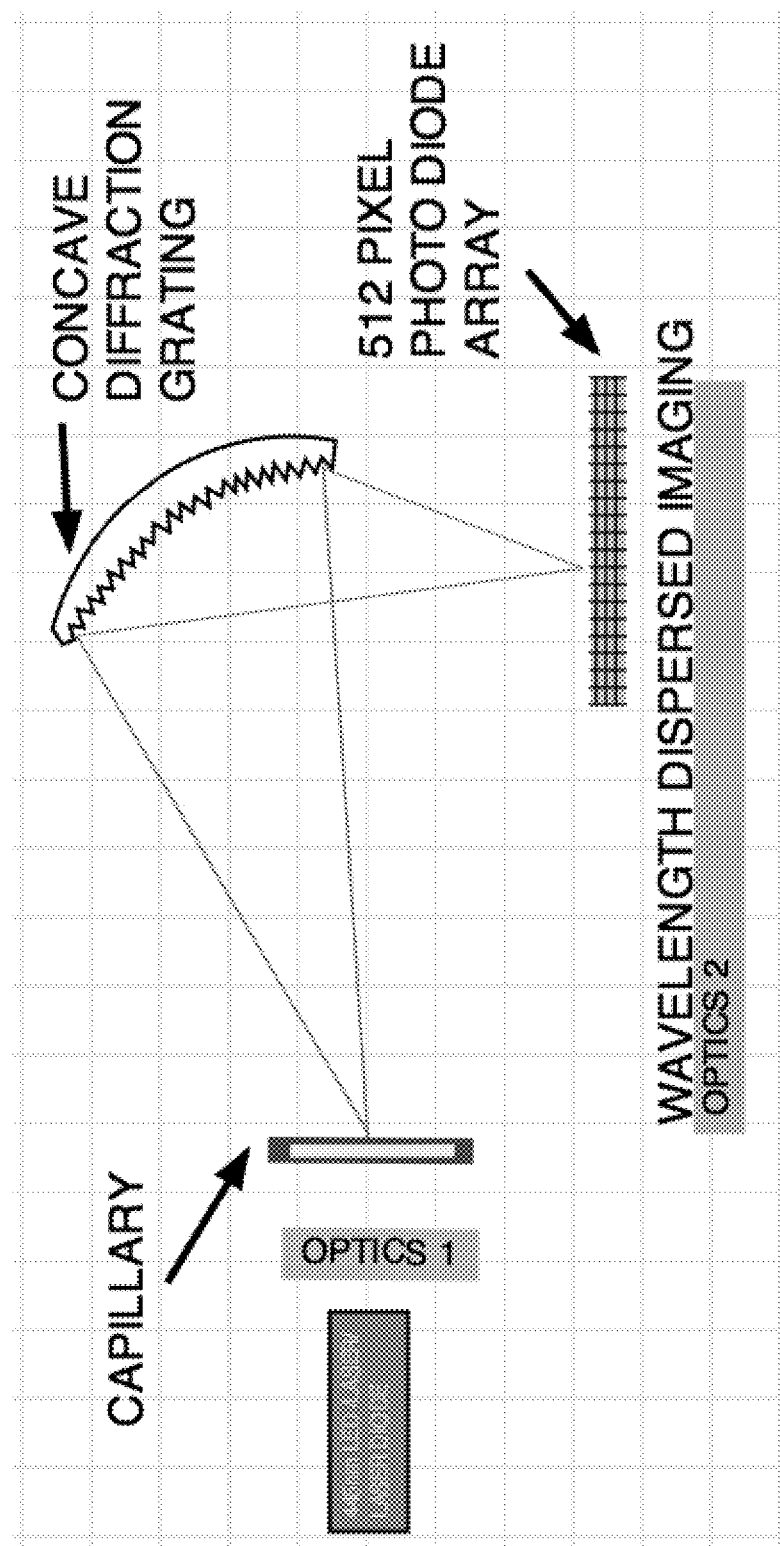
FIG. 2 is a schematic drawing of a system comprising two optics zones. Optics zone 1 comprises a 445 nm LED/Laser/Laser Diode. Optics zone 2 comprises an off axis concave diffusion grating that focuses wavelength dispersed achromatic light of a wavelength specific to the fluorescent label onto the 512 pixel photo diode array. By rotating the diffraction grating, the light energy reaches the detector where the data is acquired on the PDA and the signal is processed by proprietary signal processing algorithms. An additional cut-on filter or crossed polarizer may be added.
Figure 3:
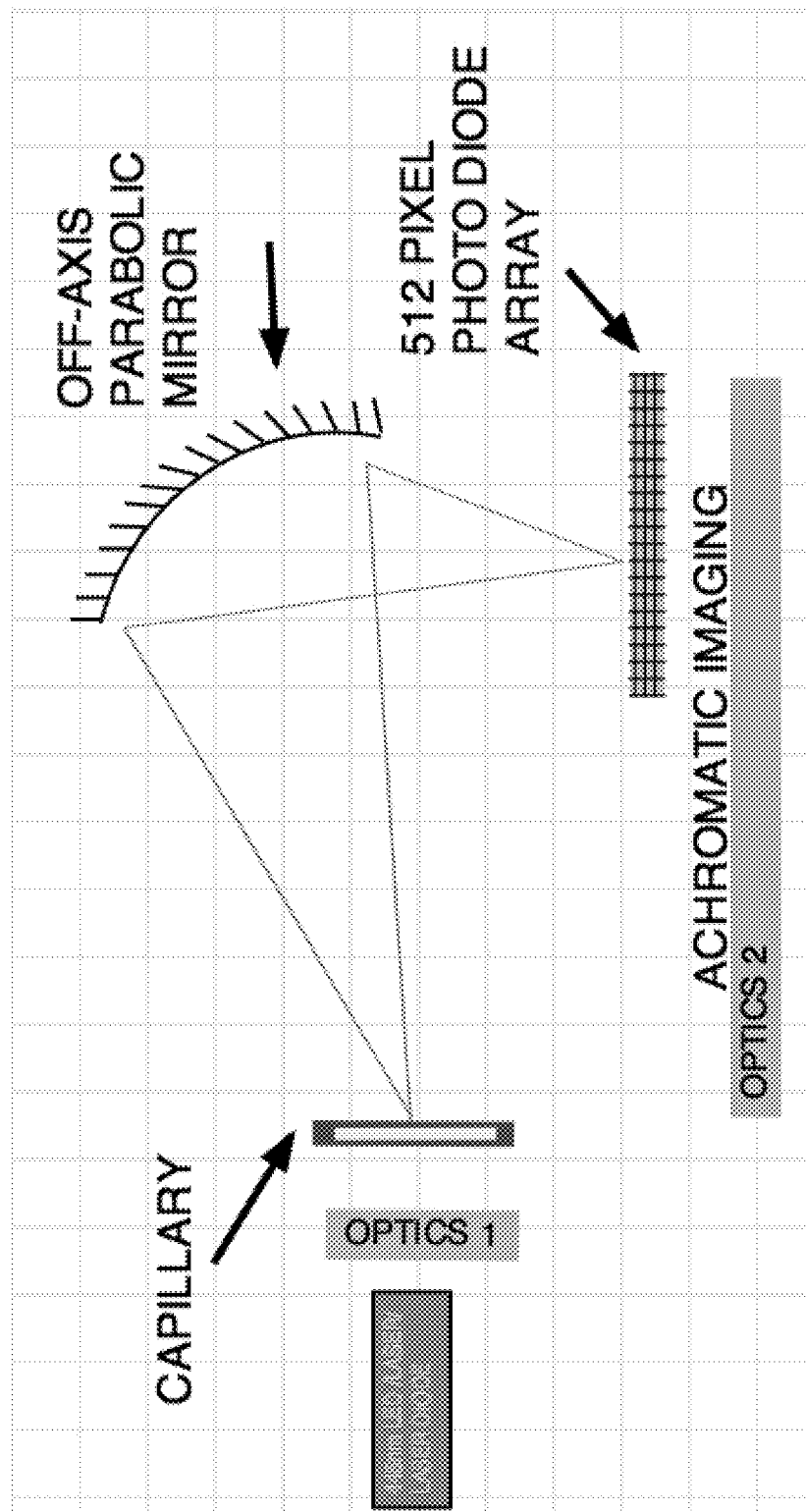
FIG. 3 is a schematic drawing of a system comprising a simple off axis translucent parabolic mirror.

FIG. 2 shows an optical apparatus with a 445 nm LED/Laser/Laser Diode in optics zone 1 and an off axis concave diffusion grating in optics zone 2. The diffusion grating focusses wavelength dispersed achromatic light of a wavelength specific to the fluorescent label onto the 512 pixel photo diode array. By rotating the diffusion grating, the light energy reaches the detector where the data is acquired on the PDA and the signal is processed by proprietary signal processing algorithms. An additional cut-on filter or crossed polarizer may be added. A simple off axis parabolic mirror may replace the diffusion grating (FIG. 3).

Figure 4:
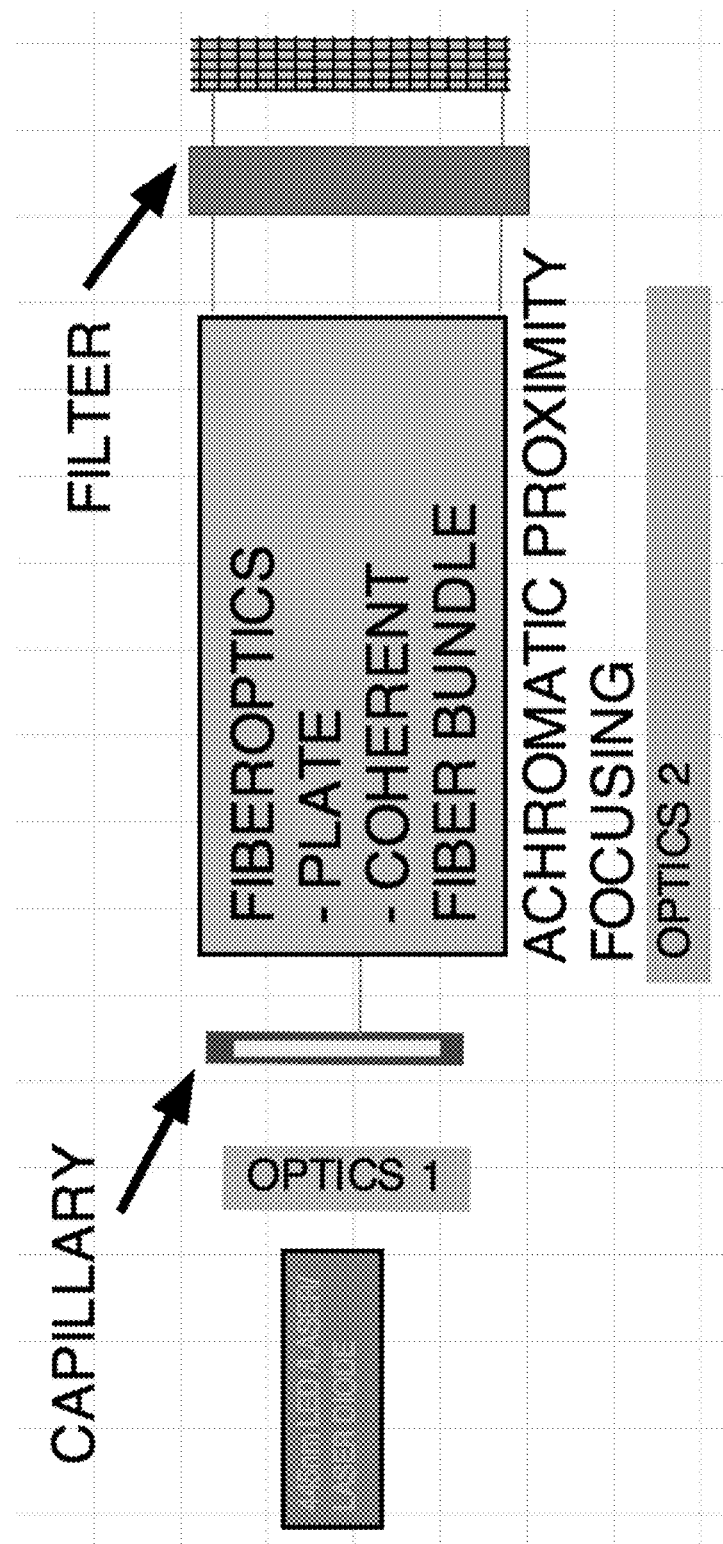
FIG. 4 is a schematic drawing of a system comprising two optics zones. Optics zone 2 comprises a fibre-optic plate ("FOP") or coherent fibre bundle allowing proximity focusing via a cut-on filter without needing the PDA to touch the capillary.

FIG. 4 is a schematic of an optical system comprising a fibre-optic plate ("FOP") or coherent fibre bundle in optics zone 2. This configuration allows for proximity focusing via a cut-on filter without needing the PDA to touch the capillary (FIG. 4).

Materials and Methods for Examples 2-5

Leading and Terminating Electrolytes.

The leading electrolyte consists of 10 mm HCL, 0.3% w/v hydroxypropylmethylcellulose ("HPMC"), and 17 mM 2-amino-2-methyl-1,3-propanediol ("Ammediol"). The terminating electrolyte contained 20 mM alanine, 17 mM Ammediol, and was adjusted to pH 10.6 with saturated barium hydroxide solution.

Preparation of Spacer Solutions.

Spacer solutions were prepared to a concentration of 0.32 mg/ml in deionized water and stored at 4° C. Various spacers were made from stock solutions of the following compounds: N-2-acetamido-2-aminoethanesulfonic acid ("ACES"), D-glucuronic acid, octane-sulfonic acid, 2-[(2-Hydroxy-1,1-bis(hydroxymethyl)ethyl)amino]ethanesulfonic acid, 3-[[1,3-dihydroxy-2-(hydroxymethyl)propan-2-yl]amino]propane-1-sulfonic acid, serine, glutamine; methionine, and glycine.

Preparation of the Internal Standard.

1 mg/ml and 2.8 mg·ml carboxyfluorescein ("CF") solution was prepared in deionized water ("DI") water and isolated from light.

Biological Samples.

Biological samples were prepared from patients identified as 1, 2, 3, 4, 5, 6, 7, and 8. Patient samples 1, 2, and 6 were previously identified as Lp(a) positive. Patient sample 4 was previously identified as negative for Lp(a).

Biological Sample Preparation.

Biological samples comprising lipoproteins were stained with the fluorescent lipophilic dye 7-nitro-benz-2-oxa-1,3-diazole ("NBD") ceramide. Briefly, 5 μl of a biological sample were diluted in 37.5 μl deionized water. The diluted sample was incubated for 1 minute with 20 μl NBD-ceramide solution (0.5 mg/ml in ethylene glycol:DMSO, 9:1 (v/v)), mixed with 100 μl of spacer solution (0.32 mg/ml), and spiked with 2.5 μl of the carboxyfluorescein internal standard. In some instances, NBD-ceramide was omitted and replaced with 20 μl of DI water. For biological samples evaluated in the presence of a lipoprotein spike, 2.5 μl of the biological sample was combined with 2.5 μl of the lipoprotein spike prior to dilution in deionized water.

Sample Loading and Data Acquisition.

Samples were injected into a 20 cm Rxi capillary (100 μm) using pressurized injection for 9 seconds at 1 psi. Separation was performed at constant 8 kV. The separated zones were monitored with laser-induced fluorescence detection (excitation 445 nm; emission 550 nm).

Data Analysis and Signal Processing.

Data analysis consists of three stages. First, peak searching is performed on each individual pixel electropherogram (FIG. 5A). Each detected peak is quantified in terms of migration time and peak area (or peak height). Peak area correlates to the particle number of a detected analyte. Next, an algorithm sorts through all of the detected peaks and assigns them to tracks, which represent the path of the analytes across the capillary window (FIG. 5B). Once a set of peaks has been assigned to a track, a linear fit is used to determine the velocity of the analyte averaged across all of the pixels (FIG. 5C), which is needed for signal averaging between pixels.

Example 2—Replicate Lipoprotein Profiles of a Single Biological Sample

Figure 6A:
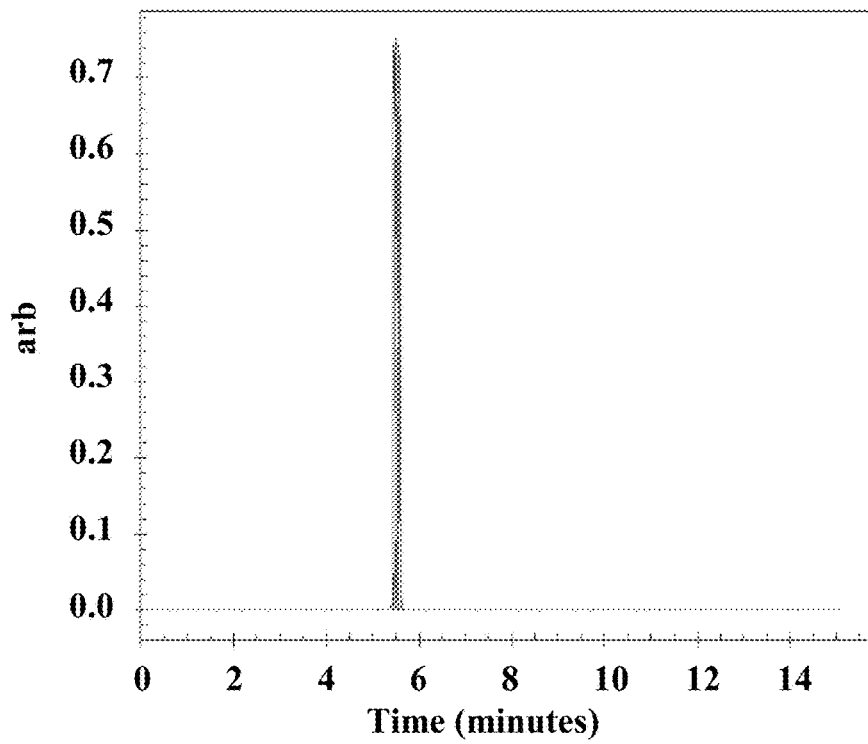
FIGS. 6A-6C are electropherograms of multiple samples showing the detection of individual fractions by CE-ITP-ILF.
Figure 6B:
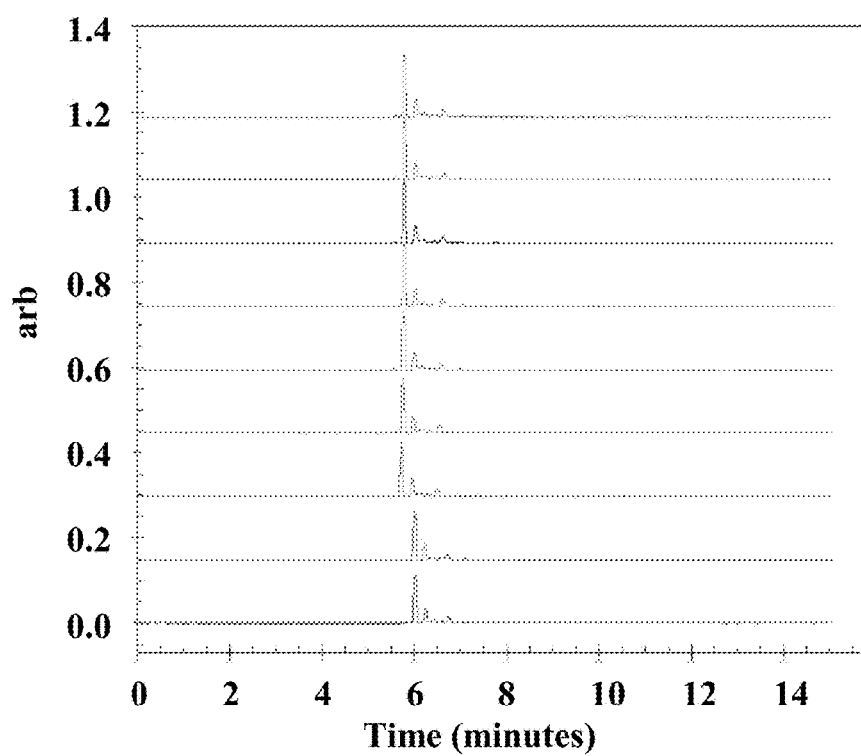
Figure 6C:
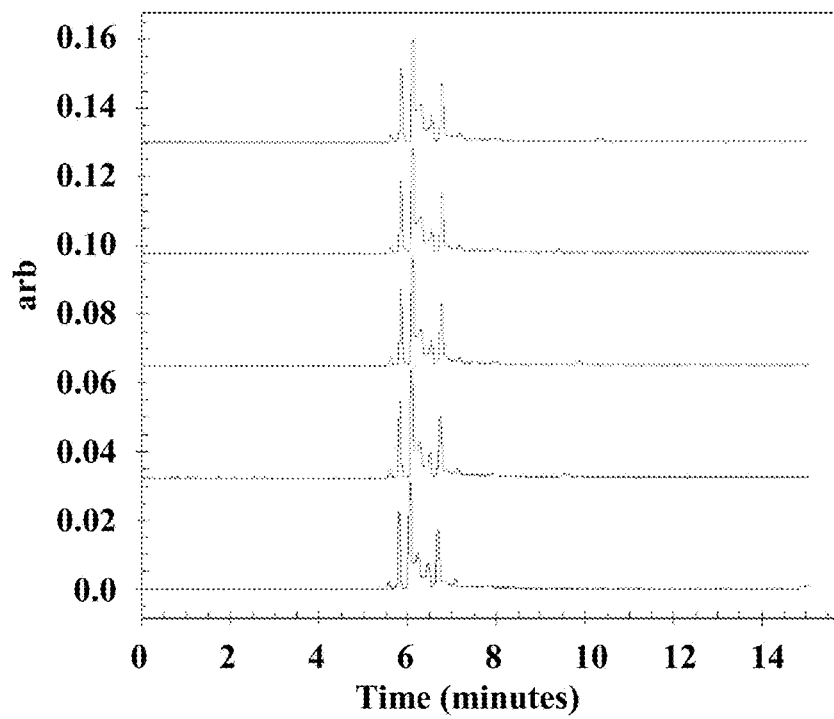

To test the reproducibility of the CE-ITP-LIF system, several replicate biological samples from a single patient were evaluated. As a control experiment, the non-specific lipophilic dye CF was run on the ITP system in the absence of a biological sample. FIG. 6A shows an electropherogram of the control experiment with a peak corresponding to CF (migration time=0.7999), area under peak=2.345). Next, lipoprotein particles in replicate biological samples from patient 8 were labeled with CF and run with a standard CF sample. FIG. 6B is an electropherogram showing the lipoprotein profile of each replicate sample tested. The lipid profile remains constant even after CF has degraded (FIG. 6C).

Figure 7A:
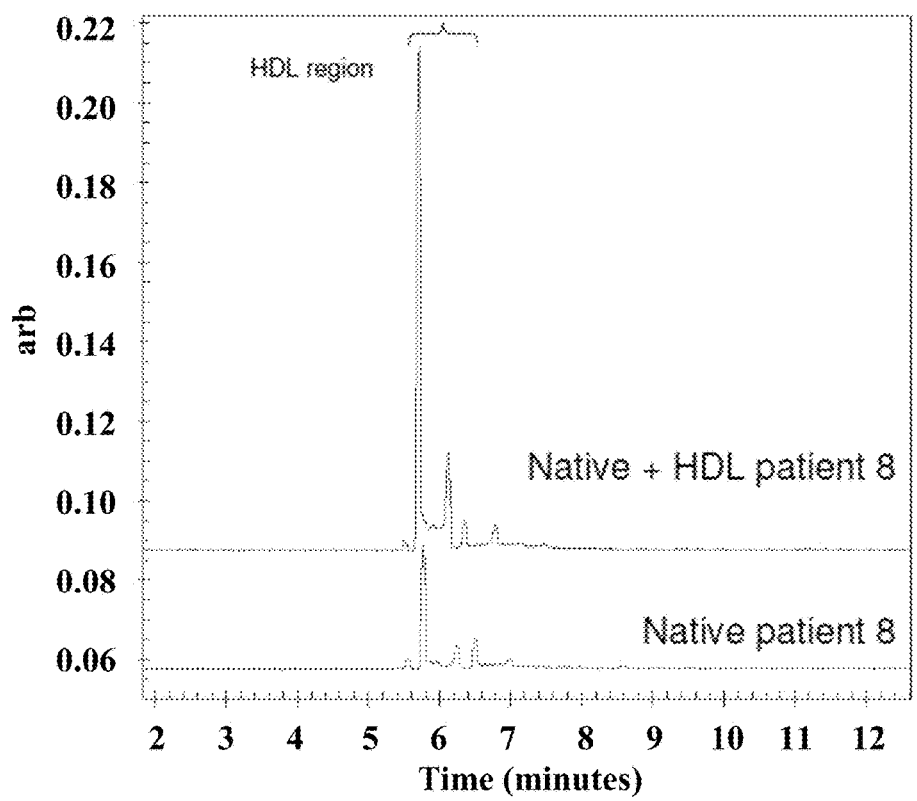
FIGS. 7A-7C are electropherograms of native samples from patient 8 prepared in the presence or absence of a lipoprotein spike.
Figure 7B:
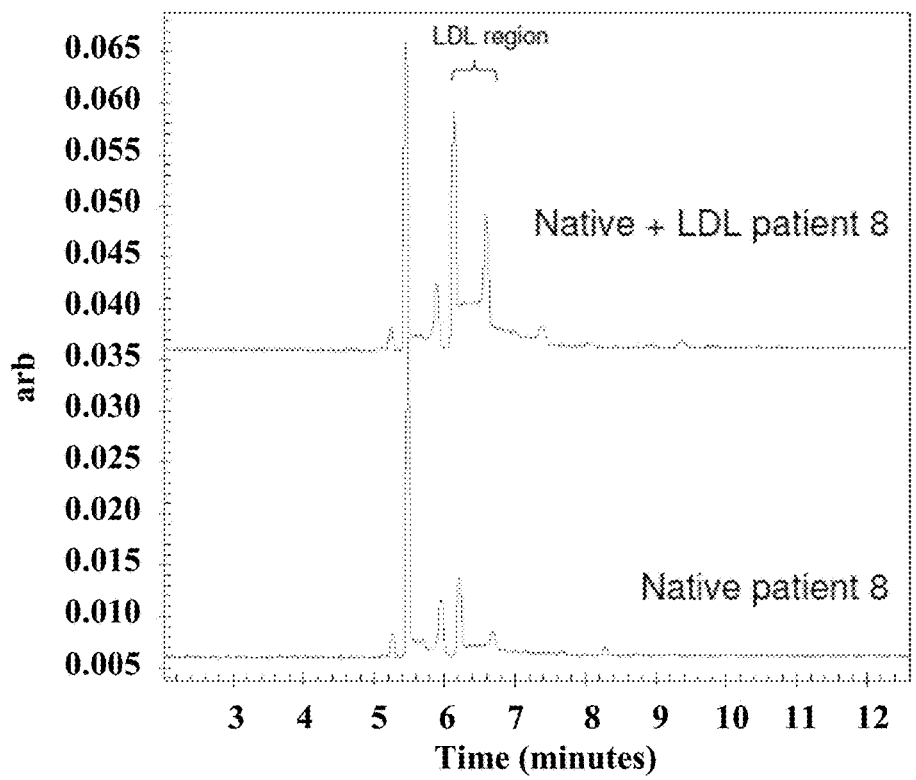
Figure 7C:
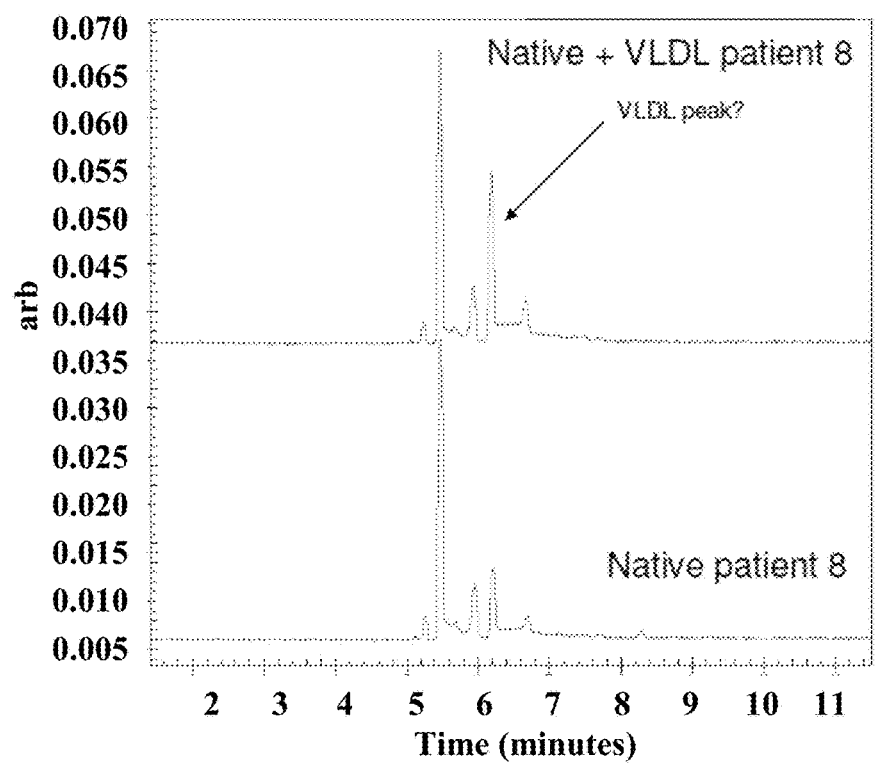

Example 3—Lipoprotein Particle Spiking Results in a Marked Increase in the Corresponding Detected Lipoprotein Peak Height The lipoprotein profile of a biological sample stained with NBD-ceramide generates several peaks corresponding to individual serum lipoproteins (FIGS. 6A-6B). To validate the identity of each individual lipoprotein peak, biological samples were spiked with known amounts of purified lipoprotein. To validate peaks corresponding to HDL and LDL, native samples from patient 8 were spiked with purified HDL and LDL, respectively. The lipid profile of the HDL spiked sample (FIG. 7A, top) and the LDL spiked sample (FIG. 7B, top) were aligned with the lipid profile generated by the native sample (FIG. 7A, bottom; FIG. 7, bottom). As shown in FIG. 7A, there was a marked increase in the peak height and area under the peak in the HDL spiked sample compared to the native sample. FIG. 7B shows the same relationship between the LDL spiked sample compared to the native sample. FIG. 7C shows the lipid profile of a VLDL spiked sample compared to a native sample from patient 8. The VLDL peak (FIG. 7, arrow) seems to fall within the region identified by the LDL spiked sample in FIG. 7B.

Example 4—Evaluation of Multiple Biological Samples

Figure 8A:
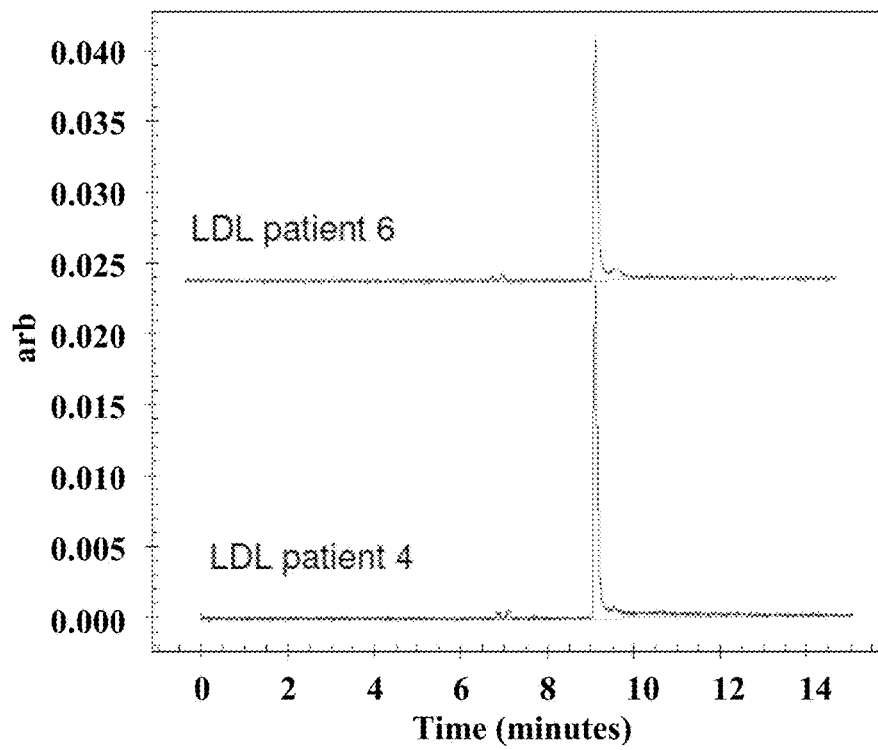
FIGS. 8A-8E are electropherograms showing the lipid profiles of various biological samples.
Figure 8B:
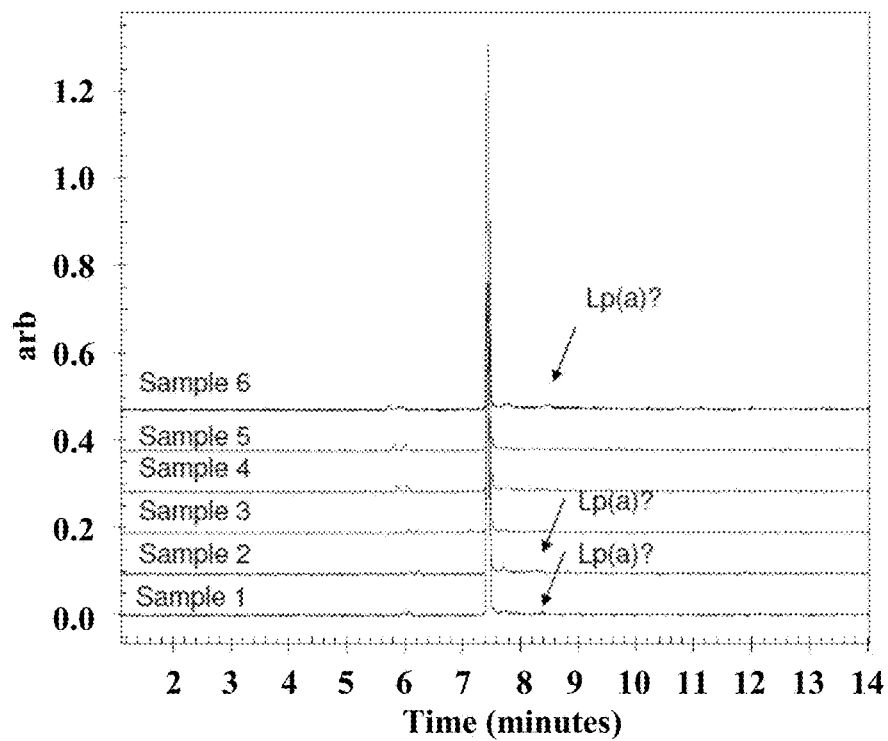
Figure 8C:
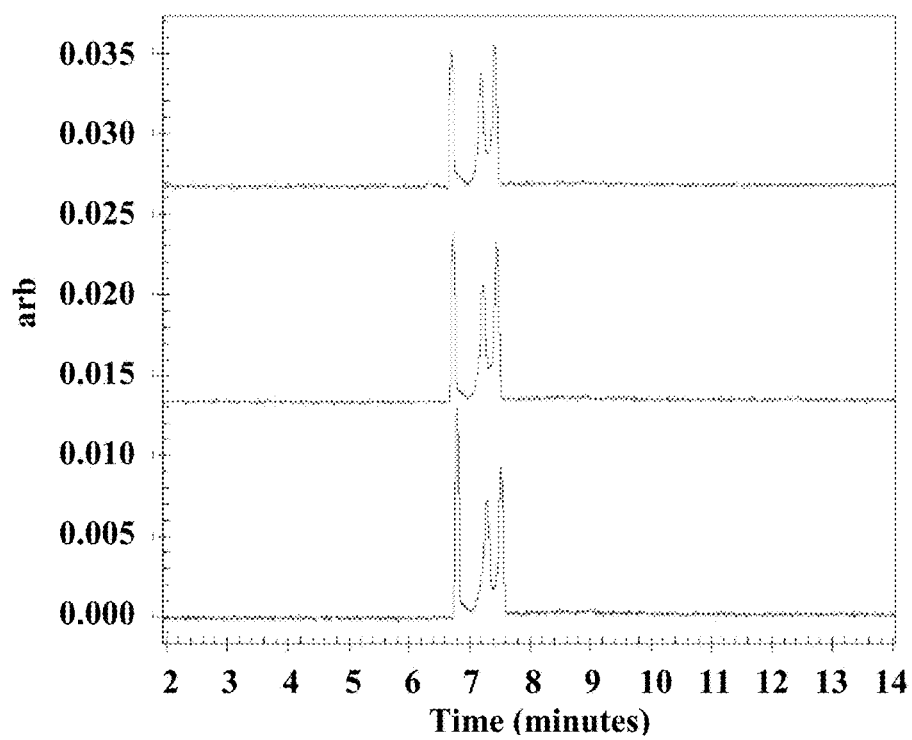
Figure 8D:
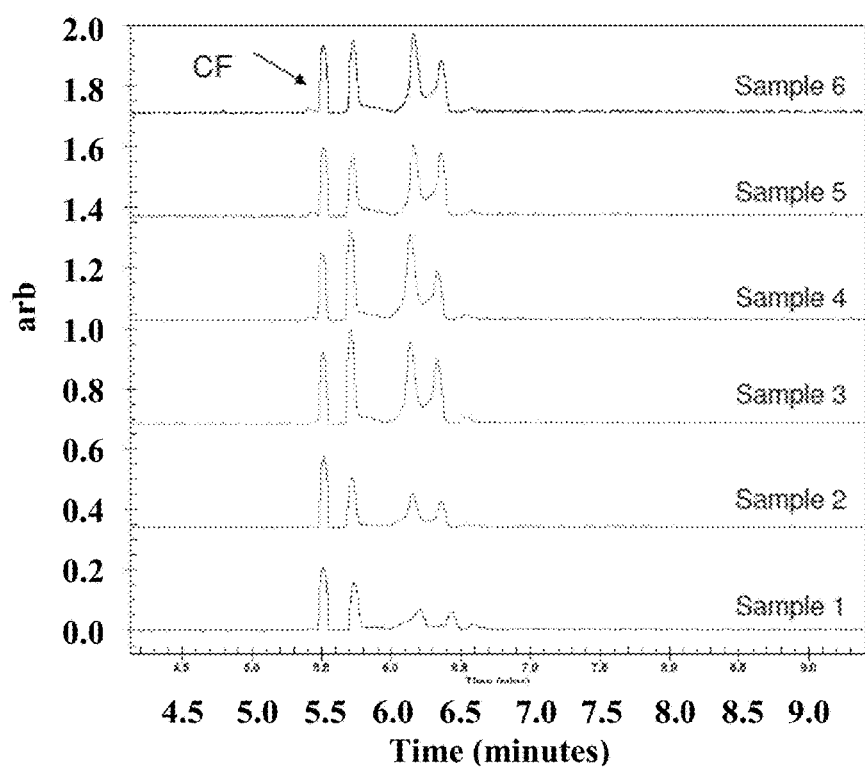
Figure 8E:
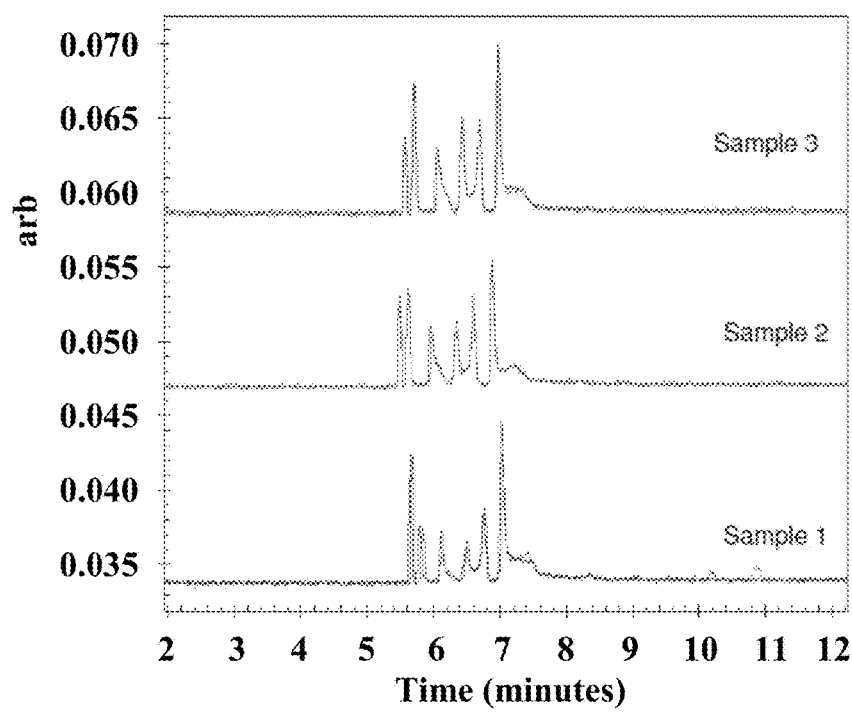

To further evaluate the reproducibility of the system, several samples with known lipoprotein profiles were evaluated. Samples from patients 1, 2, and 6 were previously determined to be Lp(a) positive. Samples from patient 4 were previously determined to be Lp(a) negative. FIG. 8A shows an alignment of the lipid profiles from patient 6 (top) and patient 4 (bottom). The arrows in FIG. 8B indicate the possible location of a Lp(a) peak in samples 1, 2, and 6.

Example 5—Quantification of HDL and LDL

Figure 9A:
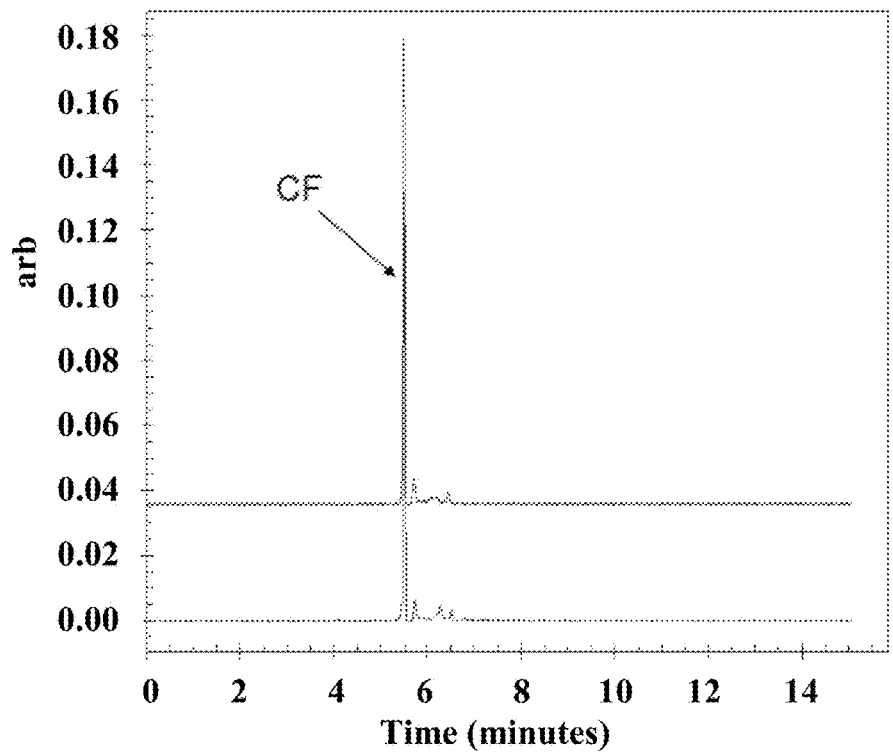
FIGS. 9A-9G show the lipid profiles of 6 biological samples.
Figure 9B:
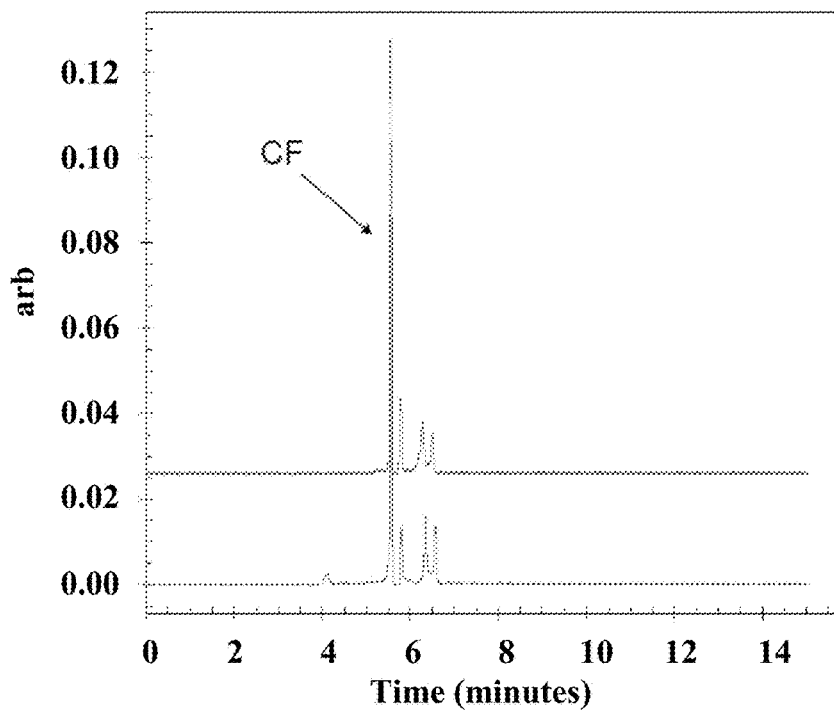
Figure 9C:
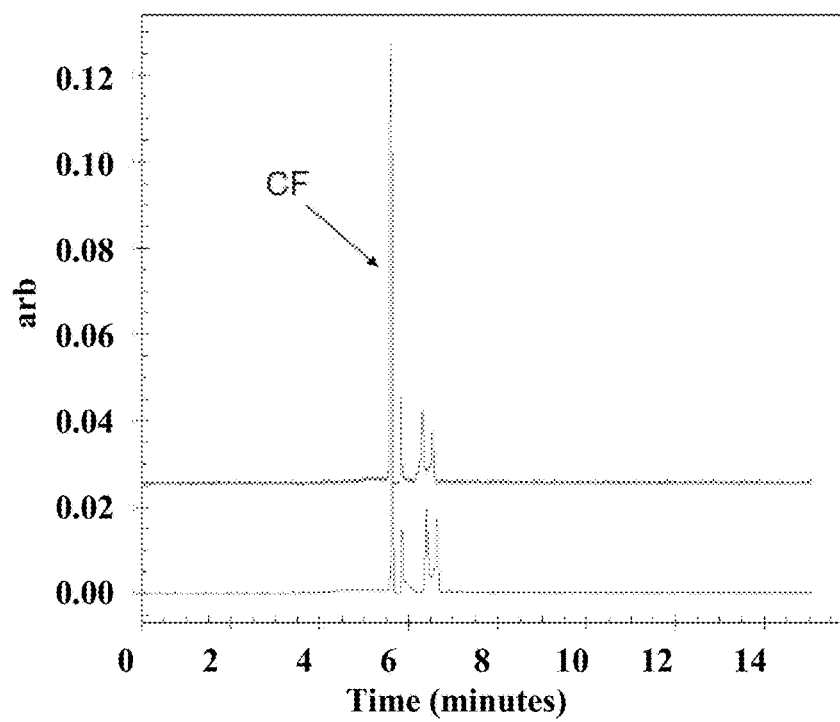
Figure 9D:
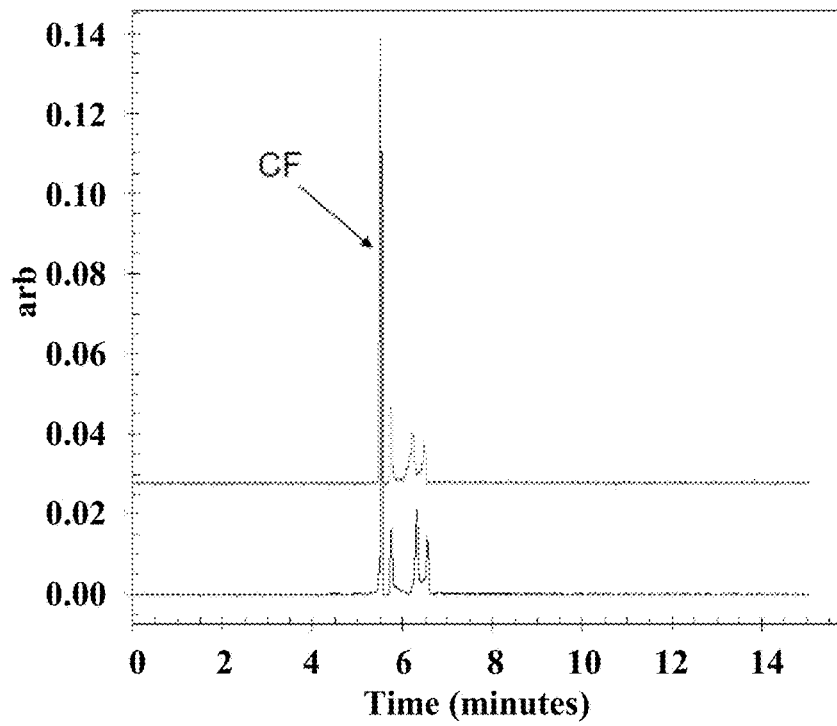
Figure 9E:
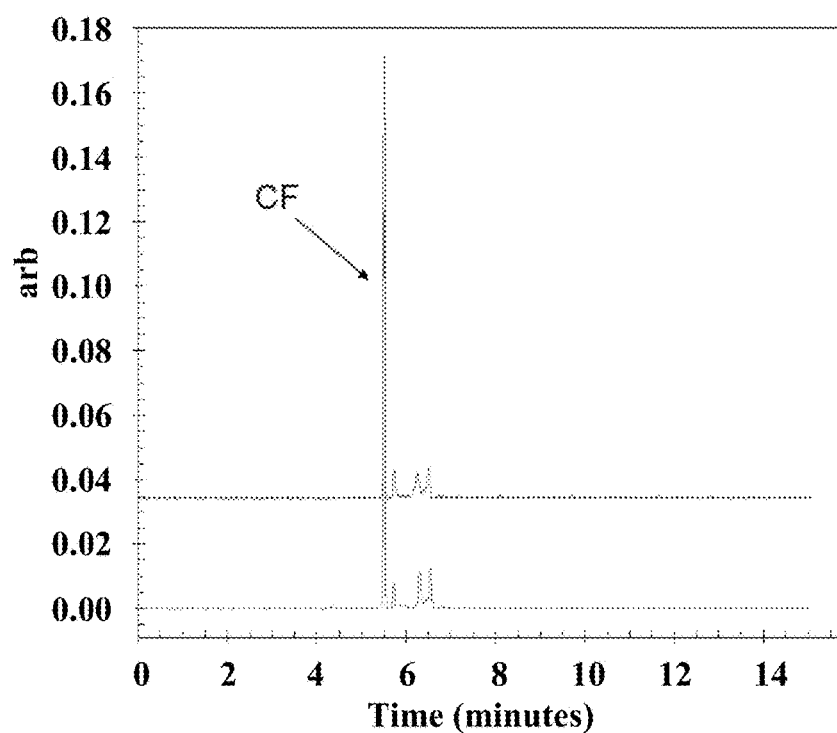
Figure 9F:
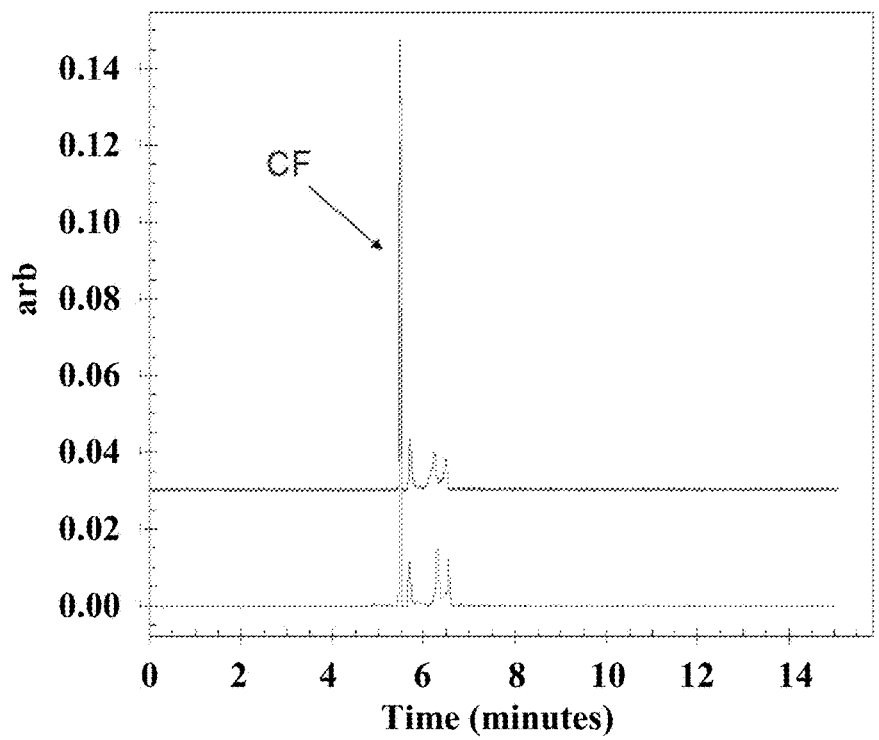
Figure 9G:
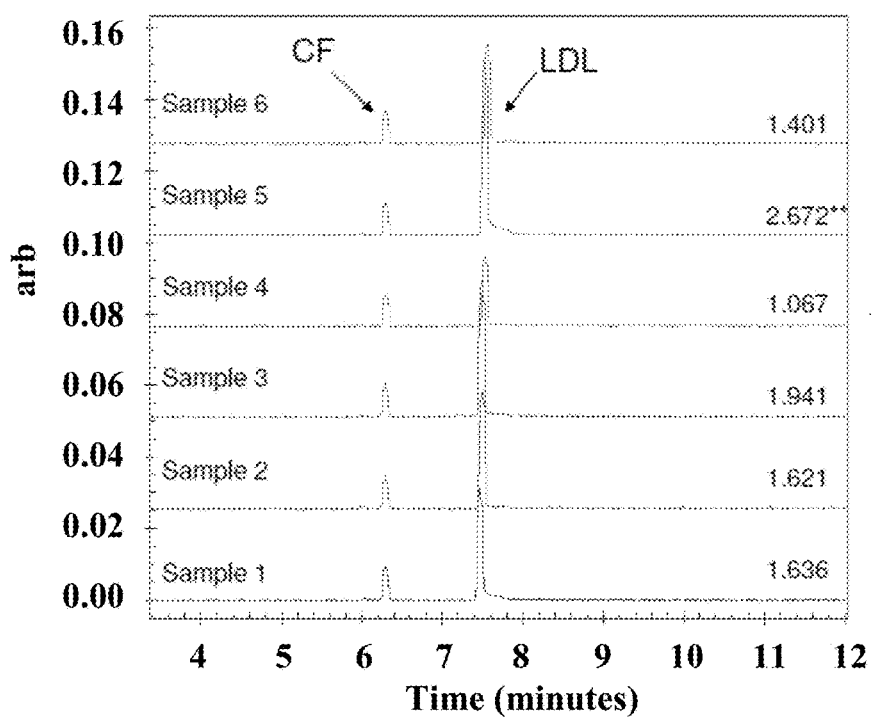

To determine the amounts of HDL and LDL in each of the six patient samples, samples were compared and relative quantities were calculated. Individual electropherograms corresponding to samples 1-6 are shown in FIGS. 9A-9F. The electropherograms were aligned and normalized around the CF peak, which accounts for any fluctuations in the injection (FIG. 9G). The relative amount of HDL in each of the 6 patient samples is shown in Table 1 below. It is possible that sample 4 in FIG. 9G may have had a 2× CF spike. Accordingly, the corrected area would be half of that indicated on the graph for this sample (FIG. 9D).

TABLE 1

| Sample | Peak | Corrected Peak Area | % Area |
|---|---|---|---|
| HDL 1 | CF | 0.764 | 83.15 |
| | HDL A | 0.0638 | 6.95 |
| | HDL B | 0.0593 | 6.46 |
| | HDL C | 0.0224 | 2.44 |
| | HDL D | 0.00926 | 1.01 |
| | Total HDL | 0.16 | |
| HDL 2 | CF | 0.614 | 64.3 |
| | HDL A | 0.112 | 11.69 |
| | HDL B | 0.128 | 13.44 |
| | HDL C | 0.0953 | 9.98 |
| | HDL D | 0.00575 | 0.6 |
| | Total HDL | 0.34 | |
| HDL 3 | CF | 0.546 | 57.91 |
| | HDL A | 0.121 | 12.8 |
| | HDL B | 0.14 | 14.81 |
| | HDL C | 0.131 | 13.85 |
| | HDL D | 0.0059 | 0.63 |
| | Total HDL | 0.4 | |
| HDL 4 | CF | 0.623 | 59.43 |
| | HDL A | 0.136 | 12.99 |
| | HDL B | 0.171 | 16.26 |
| | HDL C | 0.113 | 10.75 |
| | HDL D | 0.0059 | 0.56 |
| | Total HDL | 0.43 | |
| HDL 5 | CF | 0.671 | 72.23 |
| | HDL A | 0.0716 | 7.71 |
| | HDL B | 0.0885 | 9.53 |
| | HDL C | 0.0927 | 9.98 |
| | HDL D | 0.00517 | 0.56 |
| | Total HDL | 0.26 | |
| HDL 6 | CF | 0.645 | 66.16 |
| | HDL A | 0.0989 | 10.14 |

TABLE 1-continued

| Sample | Peak | Corrected Peak Area | % Area |
|---|---|---|---|
| | HDL B | 0.131 | 13.47 |
| | HDL C | 0.0959 | 9.83 |
| | HDL D | 0.00392 | 0.4 |
| | Total HDL | 0.33 | |

Example 6—Lp(a) Subform Size Identification Using Zonal Gel Immuno-Fixation Electrophoresis FIGS. 10-14 shows the distribution of Lp(a) subforms, differentiated by apo(a) size, by zonal electrophoresis. Extensive evidence of Lp(a) subform differentiation is exhibited. Additionally, Lp(a) doublet bands from the Lp(a)-P protocol are shown indicating two subpopulations of apo(a) in a patient.

The experiments and descriptions thereof that follow demonstrate a relationship between migration velocities and Lp(a) subform size. Faster Lp(a) particles correspond to larger apo(a) apolipoprotein moieties and slower particles indicate smaller apo(a). Additional distinction is drawn from known Lp(a) size standards.

Apo(a) molecular weights (MW) have been measured on 130 samples with migration biases as well as doublets. All results confirm the proportionality between MW and Migration Velocity on zonal gels. Also, it shows that subform types can be blended without compromise to either migration velocity or subform size. Such will allow the preparation of a subform reference control which would establish "on gel" Lp(a) subform MW markers. Such a reference would provide quantitative quality control for particle number and a migration velocity reference to categorize Lp(a) particles into large, mid- and small MWs. All individuals express two subform types. Doublets are seen on the gel when there is sufficient kringle/MW difference between the apo(a) of the Lp(a)–Particles to match the resolving ability of the system. This system is adequate to probe and validate clinical significance of Lp(a)-subforms. The gels can be modified to increase resolution if necessary by methods known in the art. The system identifies both bands for particle number and size.

Figure 10:
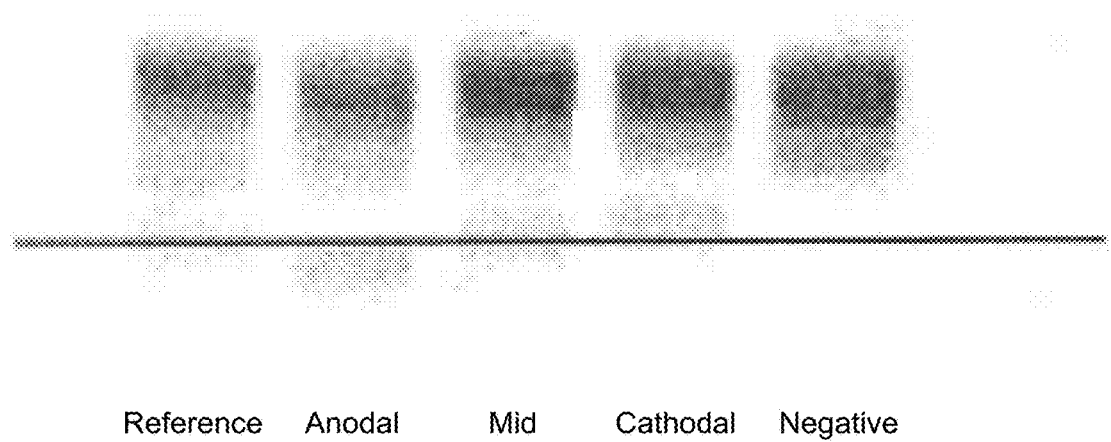
FIG. 10 shows the variable migration rates of various Lp(a) particles. The electrophoretic banding pattern seen in FIG. 10 corresponds to samples comprising three types of lipoprotein particles: LDL (top band), vLDL(intermediate band), and Lp(a) (bottom band). The known reference sample comprises an Lp(a) particle with a 600-650 kD apo(a) protein. An "anodal" sample in lane 2 contains Lp(a) particles with an apo(a) protein of greater than 650 kD, the "mid" sample in lane 3 comprises apo(a) proteins of the same mass as the reference, and the "cathodal" sample in lane 4 comprises apo(a) proteins of less than about 600 kD.

FIG. 10 shows variable Lp(a) particle migration rates via the results of a Lipo-IFE protocol, as described herein. The results of 5 samples evaluated by zonal gel electrophoresis are shown. Samples all contain LDL and VLDL, and all but the negative control further includes Lp(a) particles. The reference (known) Lp(a) content comprises an apo(a) moiety of 600-650 kD. An "anodal" sample in lane 2 contains Lp(a) with an apo(a) moiety of greater than 650 kD, the "mid" sample in lane 3 contains apo(a) moieties of the same mass as the reference, 600-650 kD, and the "cathodal" sample contains apo(a) moieties of less than about 600 kD.

Figure 11A:
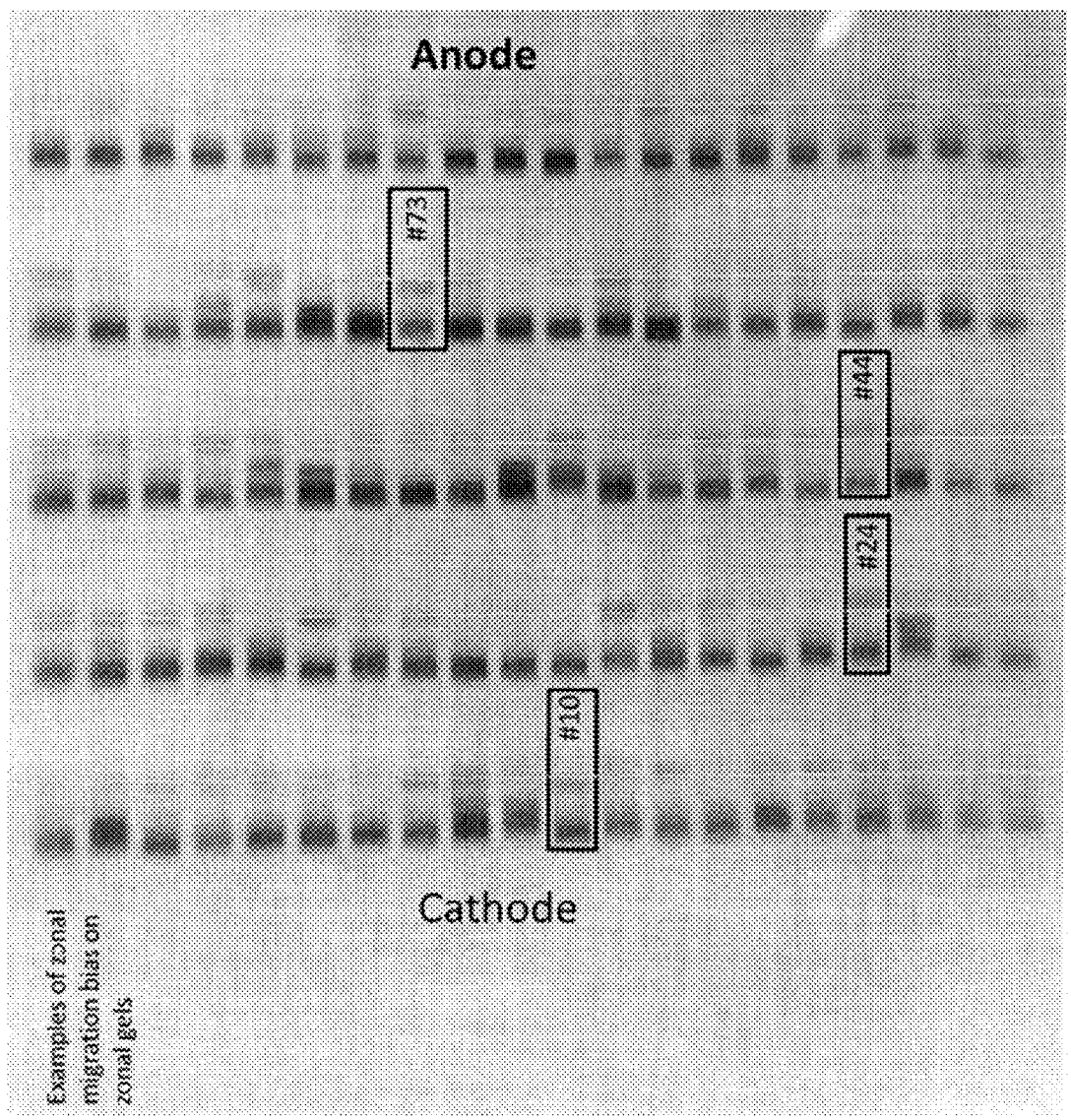
FIGS. 11A-11C shows examples of samples with differential Lp(a) particle migration bias on zonal gels.
Figure 11B:
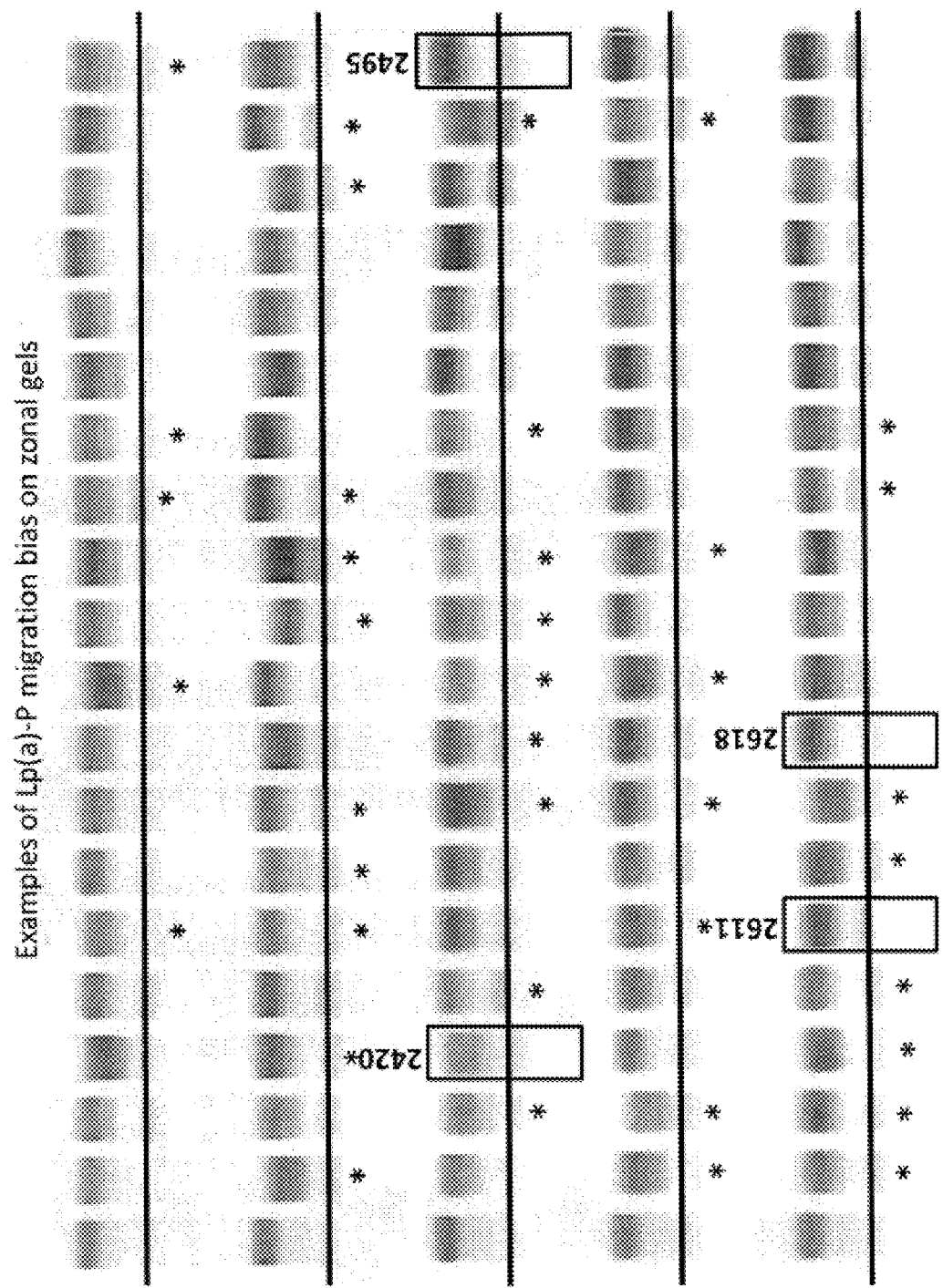
Figure 11C:
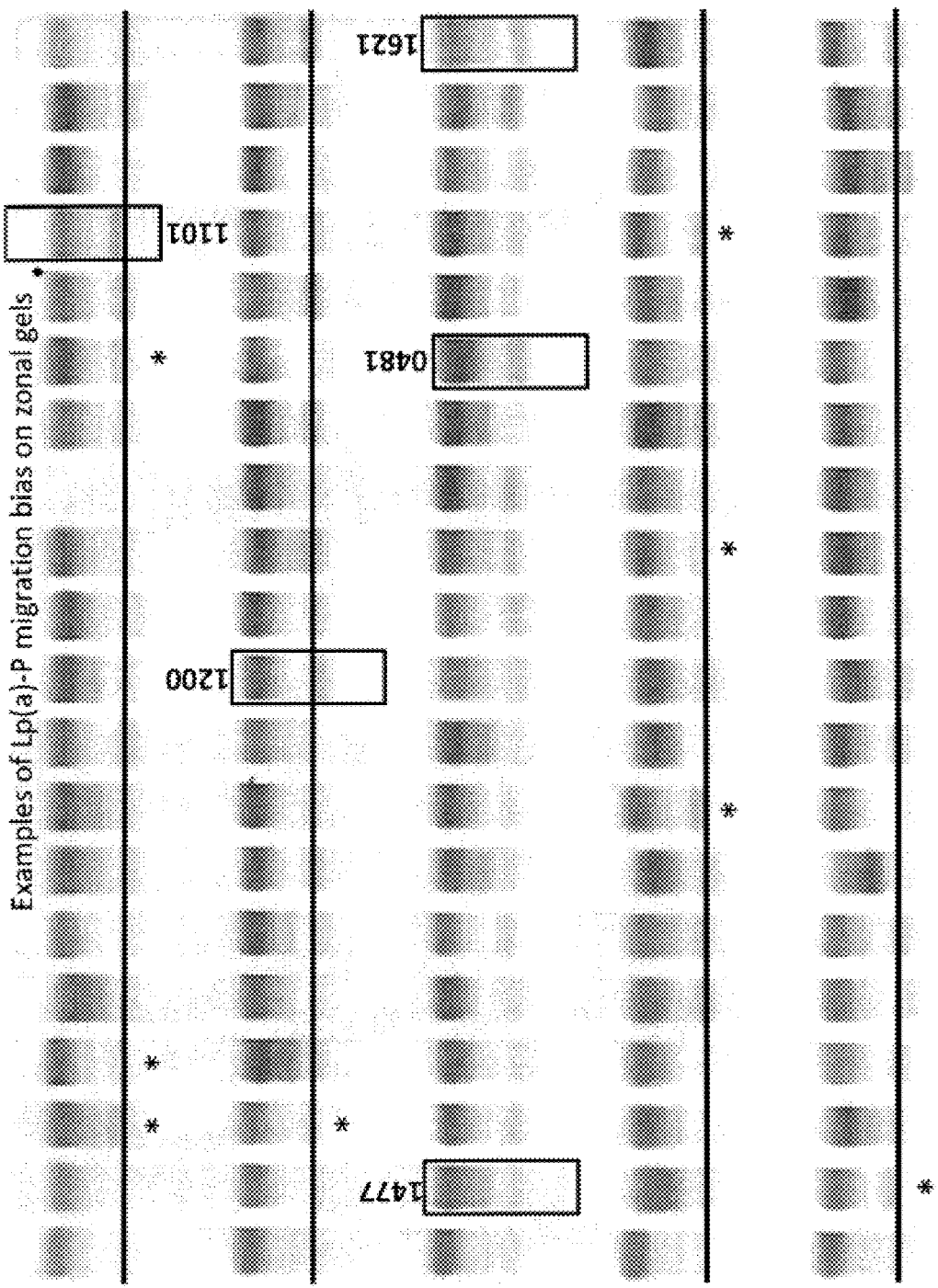

FIGS. 11A-11C show examples of samples with differential Lp(a) particle migration bias on zonal gels. In FIG. 11A, a series of samples have been run on a gel in parallel. The cathode and anode ends of the gel are labeled and solid lines represent the expected position of Lp(a) particles after separation. Four samples have been highlighted (sample numbers 10, 73, 24, and 44). These samples show distinct Lp(a) subform size difference due to the migration rates of smaller subforms (samples 10 and 73, with dashed outline and positioned toward the cathodal end of the substrate) and larger subforms (samples 24 and 44, with a solid outline and positioned toward the anodal end of the substrate). FIGS. 11B and 11C show more examples of the Lp(a) particle migration differentials in a high-throughput run. FIGS. 11B and 11C show variation among patient samples in a high-throughput experiment. Anodal particles of more than about 650 kD and cathodal particles of less than about 600 kD are identified. Anodal samples include sample numbers 1147, 1200, 0481, 1621, 2420, 2495, and 2618. Cathodal samples include sample numbers 1101 and 2611.

Figure 12:
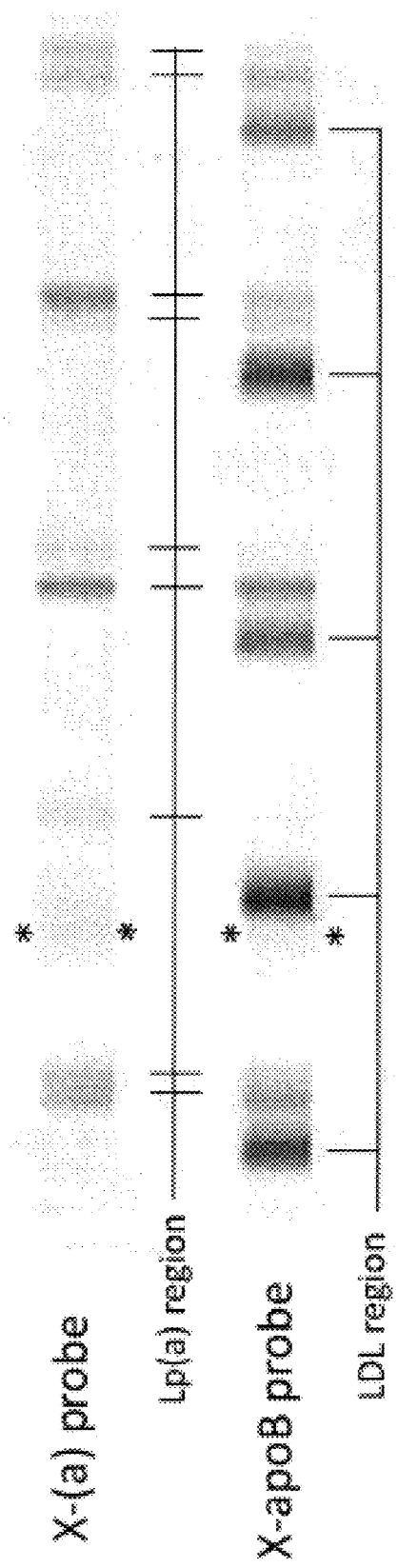
FIG. 12 shows comparison of apo(a) content and apo(b) content in a series of samples on a zonal gel. Five samples were probed by anti-apo(b) sera and anti-apo(a) sera, showing doublet banding, a product of some subjects having two sizes of apo(a) proteins on their Lp(a) particles. Lp(a) doublet banding is seen on samples 1, 3, 4, and 5. These samples contain both apo(b) and apo(a) probe response without non-specific protein residue in saline lane. Lp(a) doublet banding can be equal, primarily cathodal, or anodal with differential resolution. Sample 2 has single Lp(a), but contains both apo(b) and apo(a) response, cathodal to LDL and without non-specific protein residue in the saline lane. The frequency of doublet banding is <1%. Saline probe is used to establish presence of artifactual banding.

FIG. 12 shows comparison of apo(a) content and apoB content in a series of samples on a zonal gel. Five samples were probed by anti-apoB sera and anti-apoA sera, showing doublet banding, a product of some subjects having two sizes of apo(a) moieties on their Lp(a) particles. Lp(a) doublet banding is seen on samples 1, 3, 4 & 5 these samples contain both apoB & apo(a) probe response without non-specific protein residue in saline lane. Doublet banding is not artifactual. Lp(a) doublet banding can be equal, primarily cathodal, or anodal with differential resolution. Sample 2 has single Lp(a), but contains both apoB and apo(a) response, cathodal to LDL and without non-specific protein residue in the saline lane. The frequency of doublet banding <1%. Saline probe is used to establish presence of artifactual banding.

FIG. 13 compares the zonal gel (Lipo-IFE protocol, inset) shown in FIG. 11A to the same samples in a western blot. Samples 24, 73, 44, and 10 are further analyzed in a western blot analysis after apo(a) removal from the Lp(a) particles. Western Blot analysis was carried out using standard protocols with Apolipoprotein(a) Isoform Analysis (AAISO), using the Novex® WesternBreeze™ Chromogenic Western Blot Immunodetection Kit (Invitrogen Life Technologies). AAISO uses electrophoresis and western blot to measure Apo(a) isoforms in serum or EDTA plasma. Serum (or plasma) is first reduced in dithioerythritol and 6-aminocaproic acid then denatured in beta mercaptoethanol. The denatured sample is then loaded onto a 4% Tris Glycine gel and electrophoresed. After the electrophoresis, the proteins are transferred from the gel to a polyvinylidene fluoride transfer membrane. Western detection is then run on the PVDF membrane. All unoccupied binding sites are blocked with a Hammerstein Casein solution. The membrane is then incubated in a goat anti Lp(a) primary antibody followed by an alkaline phosphatase-conjugated anti IgO secondary antibody. A chromogenic substrate is added for the color development and the membrane is analyzed. Multiple reference standards intersperse the various lanes. Sample 24, which is an anodal (or larger) Lp(a) particle, exhibits a larger separated apo(a) in the western blot, appearing at around 700 kD and greater than 700 kD. Sample 73, which is a cathodal, smaller particle in the zonal gel) corresponds to a smaller apo(a) moiety around 600 kD in the western blot. Samples 44 and 10 repeat the pattern with an anodal Lp(a) similarly having larger apo(a) bands at ~700 kD and a cathodal Lp(a) having a smaller apo(a) band at less than 450 kD on the western blot.

Figures FIGS. 14A-14V present data comparing Lp(a)-P zonal migration velocities (inset, from FIGS. 11A-11C) associated with increasing MW of apo(a), measured by western blot. In FIGS. 14A-14V, more than 100 samples with Lp(a) zonal migration biases were compared to apo(a) isoform size analysis by western blot analysis, as described above. The results from the experiments reflecting the same setup and analysis as shown in FIG. 13 are presented. The results show consistent agreement of the new zonal gel method for analyzing Lp(a) particle subform size with the more intensive analysis of separated apo(a) moieties from the same particles.

What is claimed is:

1. A method for determining the concentration of lipoprotein(a) (Lp(a)) subforms in a biological sample, wherein the lipoprotein(a) subforms comprise a apolipoprotein(a) (apo(a)) domain, the method comprising:
    (a) contacting the biological sample with a signal-producing moiety under conditions suitable for the signal-producing moiety to bind to lipoprotein(a) subforms in the biological sample to form moiety-bound Lp(a) subforms,
    wherein the signal-producing moiety is an anti-apo(a) antibody or antibody fragment thereof that specifically binds the kringle 4 type 2 ($KIV_2$) domain;
    (b) depositing a fraction of the moiety-bound Lp(a) in a capillary isotachophoresis system;
    (c) separating components of the fraction via capillary isotachophoresis;
    (d) detecting signals produced by the signal-producing moiety bound Lp(a); and
    (e) determining concentrations of the Lp(a) subforms in the biological sample by the detected signals, wherein the detected signals are proportional to the molar concentrations of the lipoprotein(a) subforms in the fraction.

2. The method of claim 1, wherein the fraction is separated along a common capillary of the capillary isotachophoresis system such that the components of the fraction are separated from one another along the common capillary.

3. The method of claim 1, wherein the signal-producing moiety is selected from the group consisting of a radiolabel, an enzyme, a luminophore and a fluorophore.

4. The method of claim 3, wherein the enzyme is selected from the group consisting of peroxidase, alkaline phosphatase and β galactosidase.

5. The method of claim 1, wherein the capillary isotachophoresis system is a multiplex capillary isotachophoresis laser induced fluorescence (MPCE-ITP-LIF) system.

6. A method for determining the particle number of lipoprotein(a) (Lp(a)) subforms in a biological sample, wherein the lipoprotein(a) subforms comprise a apolipoprotein(a) (apo(a)) domain, the method comprising:
    (a) contacting the biological sample with a signal-producing moiety under conditions suitable for the signal-producing moiety to bind to lipoprotein(a) subforms in the biological sample to form moiety bound Lp(a) subforms,
    wherein the signal-producing moiety is an anti-apo(a) antibody or antibody fragment thereof that specifically binds the kringle 4 type 2 ($KIV_2$) domain;
    (b) depositing a fraction of the moiety-bound Lp(a) in a capillary isotachophoresis system;
    (c) separating components of the fraction via capillary isotachophoresis;
    (d) detecting signals produced by the signal-producing moiety bound Lp(a); and
    (e) determining the particle number of the Lp(a) subforms in the biological sample by the detected signals, wherein the detected signals are proportional to the particle number of the Lp(a) subforms in the fraction.

7. The method of claim 6, wherein the fraction is separated along a common capillary of the capillary isotachophoresis system such that components of the fraction are separated from one another along the common capillary.

8. The method of claim 6, wherein the signal-producing moiety is selected from the group consisting of a radiolabel, an enzyme, a luminophore, and a fluorophore.

9. The method of claim 8, wherein the enzyme is selected from the group consisting of peroxidase, alkaline phosphatase and β galactosidase.

10. The method of claim 6, wherein the capillary isotachophoresis system is a multiplex capillary isotachophoresis laser induced fluorescence (MPCE-ITP-LIF) system.

11. The method of claim 1, wherein the fraction of the sample containing the moiety-bound Lp(a) further comprises a known concentration of a signal-producing calibrator Lp(a) subform, wherein the calibrator Lp(a) subform comprises a known molar mass and/or a known number of kringle $KIV_2$ domain repeats and/or a known concentration of apo(a) and/or a known concentration of apolipoprotein B (apo(B)).

12. The method of claim 11, wherein the signal produced by the signal-producing calibrator Lp(a) is measured and compared with the signals produced from the signal producing moiety bound Lp(a) subforms and the molar mass of the Lp(a) subforms are determined based on the following formula:

$$[LP(a) - P] = [Cal\ LP(a) - P] \times \frac{(LP(a) - P\ \text{signal})}{(Cal\ LP(a) - P\ \text{signal})}$$

wherein:
[Lp(a)–P] is the molar mass of a targeted Lp(a) subform,
[Cal LP(a)–P] is the molar mass of the calibrator Lp(a) subform, (LP(a)–P), and
(Cal LP (a)–P signal) is the signal intensity of the calibrator Lp(a) subform (Cal LP(a)–P).

13. The method of claim 11, wherein the particle numbers of the Lp(a) subforms are determined as molar concentration in nmol/L, wherein the particle numbers of the Lp(a) subforms are quantified based on apo(b) concentration of the Lp(a) subforms.

14. A method of assessing cardiovascular risk in a subject, comprising
(i) determining molar mass of Lp(a) subforms in a biological sample from the subject by performing the method of claim 1; and
(ii) assessing cardiovascular risk of the subject based on the results of step (i); wherein assessing comprises assigning the subject to a low, moderate or high cardiovascular risk category based on the results of step (i),
wherein the subject is assigned to the low risk category when the molar mass of Lp(a) subforms is less than about 600 kD,
wherein the subject is assigned to the moderate risk category when the molar mass of the Lp(a) subforms is between about 600 kD and 700 kD,
and wherein the subject is assigned to the high risk category when the molar mass of the Lp(a) subforms is greater than about 700 kD; and
(iii) treating the subject based on the assignment to the low, moderate or high risk, wherein the treatment is selected from the group consisting of selecting a therapeutic regimen for the subject and modifying or changing an existing therapeutic regimen,
wherein the therapeutic regimen consists of administering to the subject a drug and/or supplement,
wherein the drug and/or supplement is selected from the group consisting of niacin, statin, ezetimibe, fenofibrate, estrogen, raloxifene and any combination thereof.

15. The method of claim 14, wherein the selected therapeutic regimen further comprises giving recommendations on making or maintaining lifestyle choices based on the results of the cardiovascular risk determination.

16. The method of claim 15, wherein the lifestyle choices are selected from the group consisting of changes in diet, changes in exercise, reducing or eliminating smoking, and a combination thereof.

17. The method of claim 1, wherein the biological sample is selected from the group consisting of blood, plasma, urine and saliva.

* * * * *